(12) United States Patent
Isoda et al.

(10) Patent No.: US 10,323,271 B2
(45) Date of Patent: Jun. 18, 2019

(54) PROBE REAGENT AND FISH USING PROBE REAGENT

(71) Applicant: Konica Minolta, Inc., Tokyo (JP)

(72) Inventors: Takeshi Isoda, Sayama (JP); Mitsuru Sekiguchi, Tokyo (JP); Yutaka Hatanaka, Sapporo (JP); Yoshikazu Kurihara, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 20 days.

(21) Appl. No.: 15/125,651

(22) PCT Filed: Mar. 20, 2015

(86) PCT No.: PCT/JP2015/058612
§ 371 (c)(1),
(2) Date: Sep. 13, 2016

(87) PCT Pub. No.: WO2015/141856
PCT Pub. Date: Sep. 24, 2015

(65) Prior Publication Data
US 2017/0029878 A1    Feb. 2, 2017

(30) Foreign Application Priority Data

Mar. 20, 2014  (JP) .................................. 2014-058271

(51) Int. Cl.
*C12Q 1/6841* (2018.01)
(52) U.S. Cl.
CPC .................................. *C12Q 1/6841* (2013.01)
(58) Field of Classification Search
CPC ......... C12Q 1/6841; C12M 1/34; C07H 21/04
See application file for complete search history.

(56) References Cited

U.S. PATENT DOCUMENTS

| 2001/0034034 A1 * | 10/2001 | Bruchez | ................. | B82Y 15/00 506/17 |
| 2014/0220598 A1 * | 8/2014 | Takanashi | .......... | G01N 21/6428 435/7.23 |

FOREIGN PATENT DOCUMENTS

| JP | 2009507492 A | 2/2009 |
| JP | 2009100737 A | 5/2009 |
| JP | 2010259336 A | 11/2010 |
| JP | 2013057037 A | 3/2013 |
| WO | 2012029342 A1 | 3/2012 |
| WO | 2012/133047 A1 | 10/2012 |

OTHER PUBLICATIONS

Tholouli et al, Imaging of multiple mRNA targets using quantum dot based in situ hybridization and spectral deconvolution in clinical biopsies, 2006, Biochemical and Biophysical Research Communications, 2006, 348, 628-636. (Year: 2006).*
Zhao et al, Ultrasensitive DNA Detection Using Highly Fluorescent Bioconjugated Nanoparticles, 2003, JACS, 125, 11474-11475 (Year: 2003).*
Enrichi et al, Investigation of luminescent dye-doped or rare-earth-doped monodisperse silica nanospheres for DNA microarray labelling, 2010, Optical Materials 32,1652-1658. (Year: 2010).*
Extended European Search Report dated Jul. 28, 2017 from corresponding European Application No. 15765414.6.
Dimitris Ioannou et al: "Quantum dots as new-generation fluorochromes for FISH: an appraisal", Chromosome Research, Kluwer Academic Publishers, DO, vol. 17, No. 4, Jul. 31, 2009 (Jul. 31, 2009 ). pp. 519-530.
Laurent A. Bentoli LA et al: "Single-Step Multicolor Fluorescence in Situ Hybridization Using Semiconductor Quantum Dot-DNA Conjugates", Cell Biochemistry and Biophysics, vol. 45, No. 1, Jan. 1, 2006 (Jan. 1, 2006), pp. 59-70.
Sheng-Mei Wu et al: "Quantum-Dot-Labeled DNA Probes for Fluorescence in Situ Hybridization (FISH) in the Microorganism*Escherichia coli*", Chemphyschem—A European Journal of Chemical Physics & Physicalchemistry., vol. 7, No. 5, May 12, 2006 (May 12, 2006 ), pp. 1062-1067.
Andrew Burns et al: "Fluorescent core-shell silica nanoparticles: towards "Lab on a Particle" architectures for nanobiotechnology", Chemical Society Reviews., vol. 35, No. 11 , Jan. 1, 2006 (Jan. 1, 2006), p. 1028.
Wenwan Zhong: "Nanomaterlal s In fluorescence-based biosensing", Analytical and Bioanalytical Chemistry, Springer, Berlin, DE, vol. 394, No. 1, Feb. 17, 2009 (Feb. 17, 2009), pp. 47-59.
Gang Yao et al: "FloDots: luminescent nanoparticles", Analytical and Bioanalytical Chemistry, Springer, Berlin, DE, vol. 385, No. 3, May 6, 2006 (May 6, 2006), pp. 518-524.
Wenwan Zhong: "Nanomaterials in fluorescence-based biosensing", Analytical and Bioanalytical Chemistry, Springer, Berlin, DE, vol. 394, No. 1, Feb. 17, 2009 (Feb. 17, 2009), pp. 47-59.
Z. Jiang, et al; Detecting genomic aberrations by fluorescence in situ . . . ; J. Nanoscience Nanotechnology; vol. 7; No. 12; 2007; pp. 4254-4259.
X. Wang, et al; The emerging use of quantum dots in analysis; Anal Lett; vol. 40; No. 7-9; 2007; pp. 1497-1520.
J. Peng, et al; Detection of epstein-barr virus infection in gastric carcinomas using . . . ; J. Nanoscience Nanotechnology; vol. 11; No. 11; 2011; pp. 9725-9730.
S. Wu, et al; Direct fluorescence in situ hybridization (FISH) in *Escherichia coli* . . . ; Biosensors Bioelectron; vol. 26; No. 2; 2010; pp. 491-492.

(Continued)

*Primary Examiner* — Narayan K Bhat
(74) *Attorney, Agent, or Firm* — Lucas & Mercanti, LLP

(57) ABSTRACT

Provided are: a probe reagent which is capable of stably yielding a fluorescence signal in FISH while inhibiting non-specific adsorption by the use of a nucleic acid molecule having a smaller number of bases than a BAC probe; and FISH using the probe reagent. The probe reagent is for in situ hybridization and comprises: phosphor-integrated nanoparticles containing phosphors integrated therein; and a nucleic acid molecule having a prescribed nucleic acid sequence, which phosphor-integrated nanoparticles and nucleic acid molecule are bound with each other.

18 Claims, 4 Drawing Sheets
Specification includes a Sequence Listing.

(56) References Cited

OTHER PUBLICATIONS

R.W. Algar, et al; Beyond labels: a review of the application of quantum dots as integrated . . . ; Anal Chim Acta; vol. 673; No. 1; 2010; pp. 1-25.
International Search Report dated Jun. 16, 2015 for PCT/JP2015/058612 and English translation.
Written Opinion dated Jun. 16, 2015 for PCT/JP2015/058612 and English translation.
Notice of Reasons for Rejections dated Jul. 3, 2018 from corresponding Japanese Patent Application No. 2016-508844 and Japanese translation.
Sheng-Mei Wu, et al.; Direct fluorescence in situ hybridization (FISH) in *Escherichia coli* . . . ; Biosensors Bioelectron; vol. 26; No. 2; 2010; pp. 491-496.
Office Action dated Feb. 21, 2019 from the corresponding European Patent Application No. 15765414.6.
Notification of Reason for Refusal dated Feb. 19, 2019 from the corresponding Japanese Patent Application No. 2016-508844 and English translation.
"Ultrasensitive DNA Detection Using Highly Fluorescent Bioconjugated Nanoparticles" by Xiaojun Zhao, et al.
"Investigation of luminescent dye-doped or rare-earth-doped monodisperse silica nanospheres for DNA microarray lebelling" by F. Enrichi, et al.
Chromosome Research, 2009, vol. 17, p. 519-530.
Cell Biochem Biophys, 2006, vol. 45, p. 59-70.
ChemPhysChem, 2006, vol. 7, p. 1062-1067.
Chemical Society Reviews, 2006, vol. 35, p. 1028-1042.
Analytical and Bioanalytical Chemistry, 2009, vol. 394, p. 47-59.
Analytical and Bioanalytical Chemistry, 2006, vol. 385, p. 518-524.

\* cited by examiner

[Fig. 1]
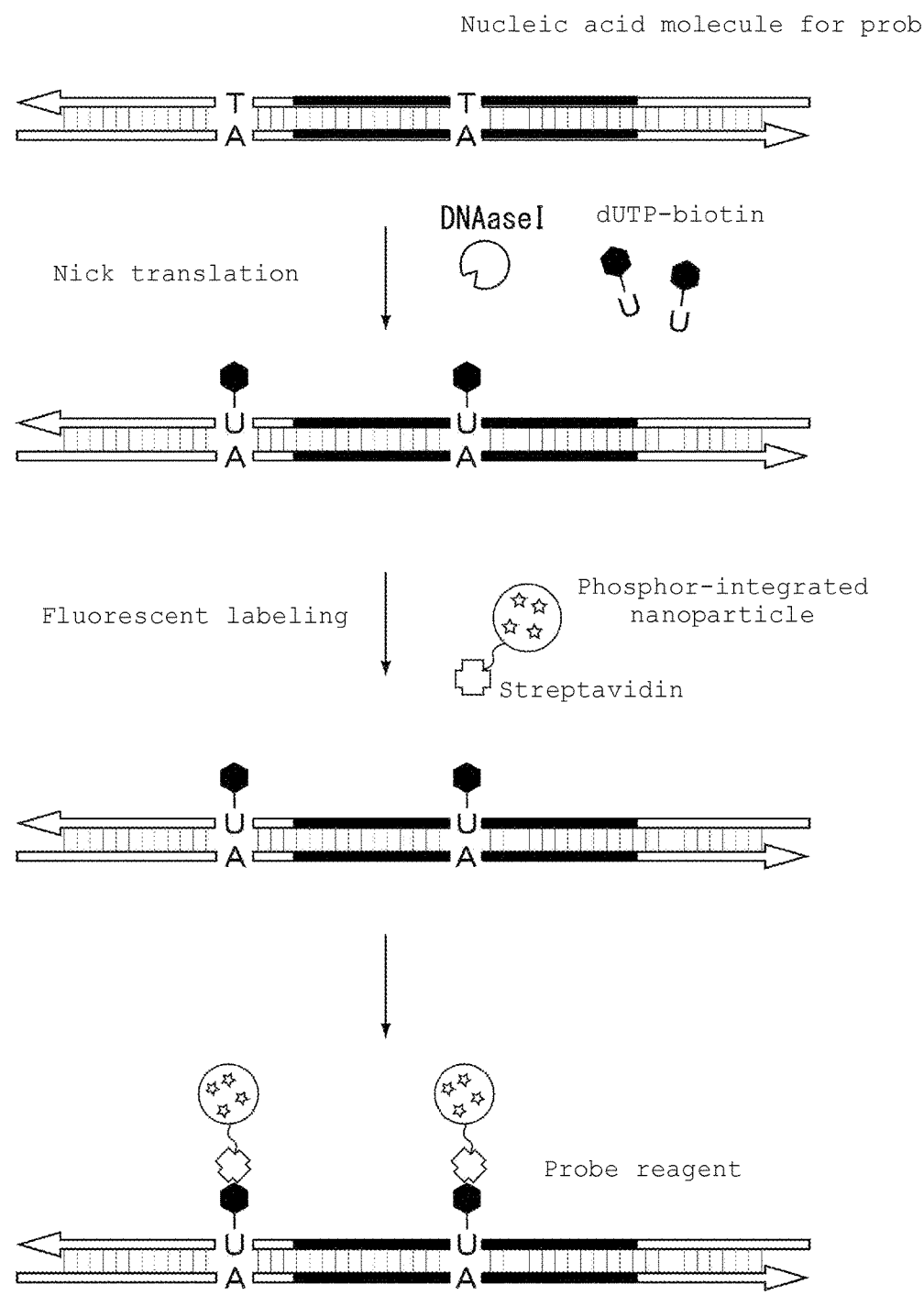

[Fig. 1A]
Nucleic acid molecule for probe
DNAaseI
Nick translation
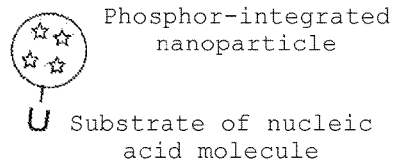
Phosphor-integrated nanoparticle
U Substrate of nucleic acid molecule
Probe reagent

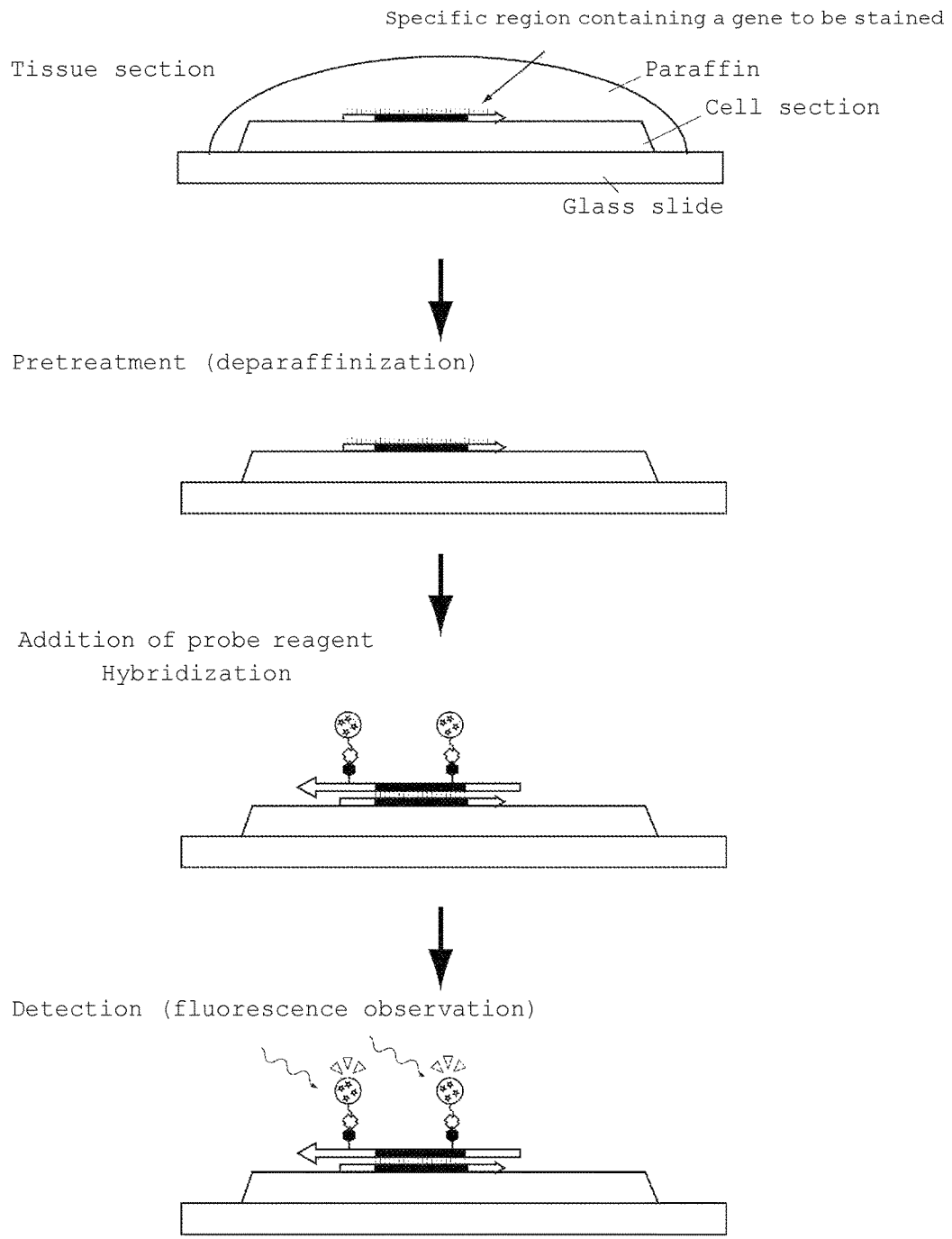
[Fig. 2]

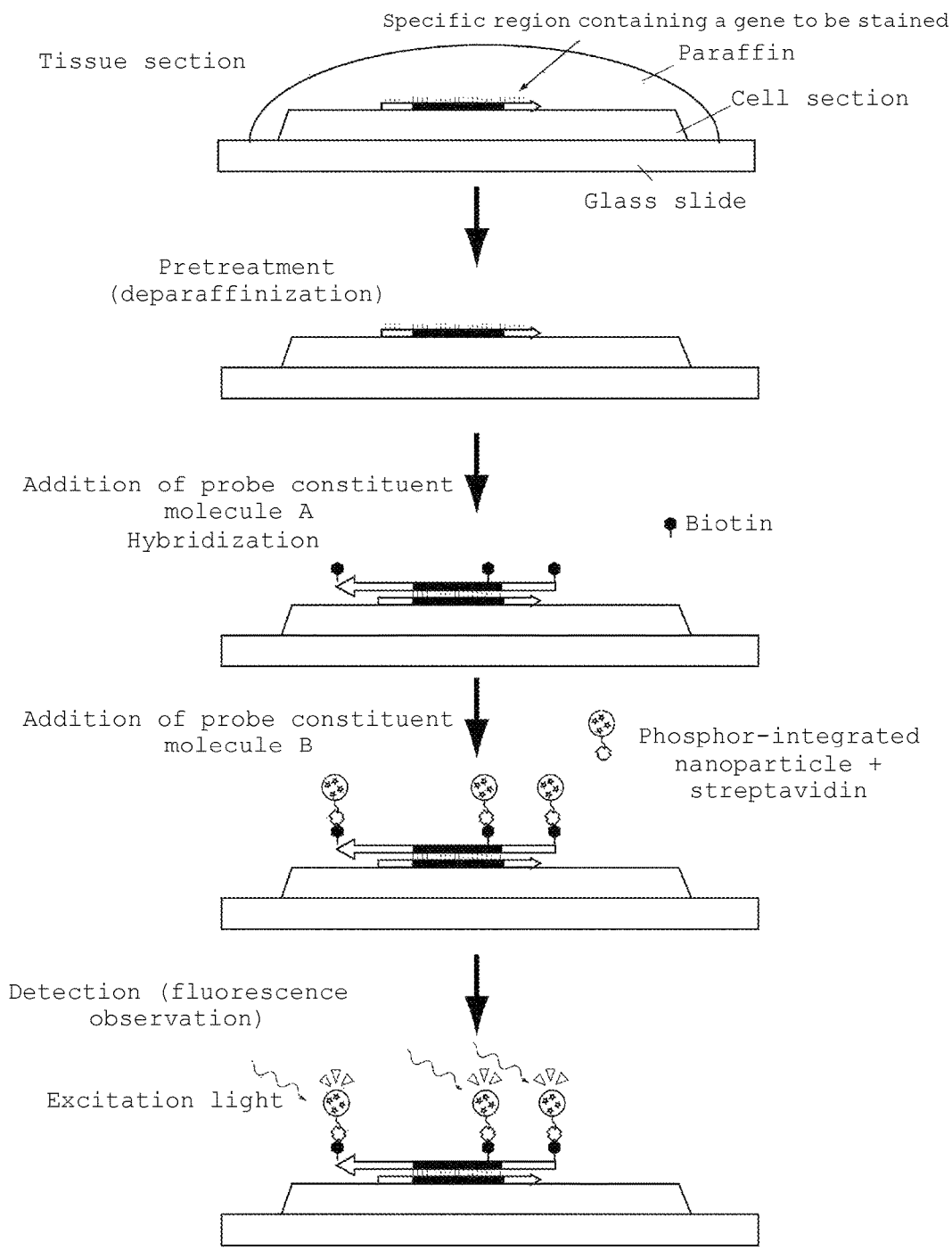
[Fig. 3]

PROBE REAGENT AND FISH USING PROBE REAGENT

CROSS REFERENCE TO RELATED APPLICATION

This Application is a 371 of PCT/JP2015/058612 filed on Mar. 20, 2015 which, in turn, claimed the priority of Japanese Patent Application No. JP 2014-058271 filed on Mar. 20, 2014, both applications are incorporated herein by reference.

TECHNICAL FIELD

The present invention relates to a probe reagent for FISH (Fluorescence in situ Hybridization), which comprises: a nucleic acid molecule having a reactive site that binds (hybridizes) to a gene on a chromosome; and phosphor-integrated nanoparticles. The present invention also relates to FISH using the same.

BACKGROUND ART

Conventionally, "fluorescent dye-integrated nanoparticles" (50 to 300 nm) comprising a biorecognition molecule (e.g., a nucleotide, an antibody or biotin) have been known (for example, the paragraph [0035] of Patent Document 1). However, there has been offered no description with regard to a solution for the problems in genetic testing.

As probe reagents for FISH (Fluorescence in situ Hybridization), BAC probes in which a plurality of low-molecular-weight dyes are bound to a nucleic acid sequence called "BAC (Bacterial Artificial Chromosome) clone" are conventionally used (for example, the paragraph [0064] of Patent Document 2). For the preparation of such a BAC probe, nick-translation reaction is known as a method of binding the low-molecular-weight dyes and, in theory, the low-molecular-weight dyes can be bound to the sites of ¼ of the number of nucleic acid sequences of a BAC clone. However, since the binding of the low-molecular-weight dyes is limited to about ⅛ of the sites in the actual reaction, a further improvement in the sensitivity could not be expected in a genetic testing performed by a FISH method using a conventional BAC probe.

As described above, in order to obtain a strong fluorescence signal, a large number of low-molecular-weight dyes have to be bound; however, a necessary and sufficient number of low-molecular-weight dyes cannot be bound to a BAC clone having a short DNA sequence of, for example, about 5,000 bp and, therefore, probe reagents prepared from a BAC clone having a long DNA sequence of 80,000 to 1,000,000 bp have been used (Patent Document 3). Nevertheless, since such a long BAC clone is replicated in *Escherichia coli* cells and then extracted, there are problems in terms of preciseness, such as susceptibility to errors, lack of consistency in length and contamination with impurities and, when hybridization is performed with a probe reagent prepared from a long BAC clone obtained by such replication and subsequent extraction, there are cases where the probe reagent also non-specifically adsorbs to base sequences other than a specific gene.

PRIOR ART REFERENCES

Patent Documents

[Patent Document 1] WO 2012/029342
[Patent Document 2] JP-A-2009-100737
[Patent Document 3] JP-A-2010-259336

SUMMARY OF THE INVENTION

Problems to be Solved by the Invention

The present inventors focused attention on the above-described problem that, when a nucleic acid molecule used in the above-described conventional BAC probes is applied to FISH performed in chromosome mapping or the like, the binding rate (labeling ratio) of low-molecular-weight fluorescent dyes to the nucleic acid molecule is limited and there are thus cases where a gene of interest cannot be detected due to insufficient brightness in the detection of the label fluorescence.

The present inventors also focused attention to the above-described problem that detection errors occur due to non-specific adsorption in FISH using a BAC probe.

Further, for example, when a short nucleic acid molecule of 5,000 or less bases, particularly 4,000 or less bases, or a FISH probe having a short nucleic acid molecule of 500 or less bases is prepared and hybridized to a 5,000-base sequence region of a specific gene, there are cases where a gene of interest cannot be detected due to insufficient fluorescence brightness.

That is, an object of the present invention is to achieve a brightness that is the same as or higher than the brightness provided by a conventional BAC probe by using a BAC probe having a labeling ratio equivalent to or lower than that of a conventional BAC probe or a probe (e.g., a BAC clone-derived probe) that is shorter and has an equivalent or lower labeling ratio as compared to a BAC probe (Problem 1).

Further, an object of another aspect of the present invention is to obtain a probe (e.g., a BAC clone-derived probe) which not only is shorter and has an equivalent or lower labeling ratio as compared to a conventional BAC probe, but also achieves a brightness that is the same as or higher than the brightness provided by a conventional BAC probe and is unlikely to adversely affect hybridization in FISH (Problem 2).

Such a probe is effective when a BAC clone with which a high labeling ratio is difficult to achieve is used and, depending on the nucleic acid sequence to be detected, such a probe is also effective when only short BAC probes are selectable.

Further, an object of another aspect of the present invention is to provide: a probe reagent which is capable of stably yielding a strong fluorescence signal in a FISH method while inhibiting non-specific adsorption that tends to occur when a BAC probe prepared from a conventional long BAC clone is used; and a FISH method using the probe reagent (Problem 3).

Technical Solution

The present inventors discovered that the above-described Problem 1 can be solved by binding nanoparticles integrated with phosphors (hereinafter, referred to as "phosphor-integrated nanoparticles") to a prescribed BAC probe. The term "binding" used herein encompasses covalent binding as well as binding between biomolecules (e.g., binding between streptavidin and biotin) and the like.

The present inventors also discovered that the above-described Problems 2 and 3 can be solved by binding phosphor-integrated nanoparticles to a terminal(s) and/or 1 to 50 spots of other than the terminals of a probe shorter than a BAC probe (e.g., BAC clone-derived probe) by a prescribed method.

Further, the present inventors discovered that, when obtaining the fluorescence signal, by performing a hybridization process of FISH using a BAC probe having a low labeling ratio or a probe that is shorter and has an equivalent or lower labeling ratio as compared to a BAC probe and then fluorescently staining the thus hybridized nucleic acid molecules with phosphor-integrated nanoparticles in which a plurality of phosphors are integrated, for example, phosphor discoloration can be inhibited and a more preferred embodiment of the present invention is attained, thereby completing the present invention.

In order to realize at least one of the above-described objects, the probe reagent for in situ hybridization that reflects one aspect of the present invention is a probe reagent for in situ hybridization which comprises: phosphor-integrated nanoparticles containing phosphors integrated therein; and a nucleic acid molecule having a prescribed nucleic acid sequence, the phosphor-integrated nanoparticles and the nucleic acid molecule being bound with each other.

Further, in order to realize at least one of the above-described objects, the probe reagent for in situ hybridization that reflects one aspect of the present invention is a probe reagent for in situ hybridization that is obtained by binding phosphor-integrated nanoparticles containing phosphors integrated therein to a nucleic acid molecule having a prescribed nucleic acid sequence of 4,000 or less bases by a nucleic acid terminal labeling method.

In order to realize at least one of the above-described objects, the probe reagent kit for FISH that reflects one aspect of the present invention is a probe reagent kit for FISH that separately comprises: a nucleic acid molecule which has a base sequence complementary to a sequence of a specific region on a chromosome and to which a first biomolecule is linked; and phosphor-integrated nanoparticles to which a second biomolecule capable of specifically binding to the first biomolecule is linked. In this case, the first and second biomolecules can be directly bound with each other, or they can be indirectly bound via a third molecule or substance.

Further, in order to realize at least one of the above-described objects, the probe reagent kit for FISH that reflects one aspect of the present invention is a probe reagent kit for FISH that separately comprises: the above-described nucleic acid molecule which has a sequence of 5,000 or less bases that is complementary to a sequence of a specific region on a chromosome and to which a first biomolecule is linked to a terminal(s) and/or 1 to 50 spots other than the terminals; and phosphor-integrated nanoparticles to which a second biomolecule capable of specifically binding to the first biomolecule is linked. In this case, the first and second biomolecules can be directly bound with each other, or they can be indirectly bound via a third molecule or substance.

In order to realize at least one of the above-described objects, the FISH that reflects one aspect of the present invention is FISH using the above-described probe reagent or kit.

Further, in order to realize at least one of the above-described objects, the FISH that reflects one aspect of the present invention is FISH comprising: performing hybridization of a nucleic acid molecule, which has a nucleic acid sequence of a BAC probe and to which a plurality of first biomolecules are linked, to a sequence of a specific region on a chromosome; and subsequently fluorescently labeling the nucleic acid molecule by adding a plurality of phosphors, to which a second biomolecule capable of specifically binding to the first biomolecules is linked, to a reaction system of the hybridization.

Still further, in order to realize at least one of the above-described objects, the FISH that reflects one aspect of the present invention is FISH comprising: performing hybridization of a nucleic acid molecule of 5,000 or less bases, which has a sequence of a BAC probe and to which a first biomolecule is linked to a terminal(s) or 1 to 50 spots other than the terminals, to a sequence of a specific region on a chromosome; and subsequently fluorescently labeling the nucleic acid molecule by adding a plurality of phosphors, to which a second biomolecule capable of specifically binding to the first biomolecules is linked, to a reaction system of the hybridization.

In order realize at least one of the above-described objects, the compound that reflects one aspect of the present invention is a compound used for the preparation of a probe reagent for in situ hybridization, wherein phosphor-integrated nanoparticles containing phosphors integrated therein and a substrate of a nucleic acid molecule are chemically bound.

In order to realize at least one of the above-described objects, the probe reagent for in situ hybridization that reflects one aspect of the present invention is a probe reagent for in situ hybridization that is characterized in that 20,000 mol or more of fluorescent nanoparticles (e.g., semiconductor nanoparticles) are bound with respect to 1 mol of a nucleic acid molecule having a prescribed nucleic acid sequence.

Advantageous Effects of Invention

The probe reagent of the present invention has a constitution in which phosphor-integrated nanoparticles having an improved luminescence brightness by integration of plural phosphors therein are bound to a prescribed nucleic acid molecule derived from a BAC probe or a probe shorter than a BAC probe (e.g., BAC clone-derived probe). Therefore, even when the probe reagent has a low labeling ratio, in FISH where a specific region of a chromosome is stained, not only the probe reagent can improve the detection accuracy of a specific gene and yields fluorescence signals with sufficient intensity for observation under a confocal microscope, but also the probe reagent enables to detect bright spots located at different depths of a tissue section simultaneously in a single field of view even when the bright spots are observed under a fluorescence microscope. Moreover, the probe reagent enables to maintain a tissue section slide subjected to FISH in a state where bright spots are detectable over a longer period of time.

BRIEF DESCRIPTION OF DRAWINGS

FIG. 1 is a drawing that illustrates the production process of one example of the probe reagent according to the present invention.

FIG. 1A is a drawing that illustrates the production process of another example of the probe reagent according to the present invention.

FIG. 2 is a drawing that illustrates a process of FISH using the probe reagent shown in FIG. 1.

FIG. 3 is a drawing that illustrates another process of FISH according to the present invention where, after hybridization, a nucleic acid molecule bound to a specific region on a chromosome is fluorescently labeled with phosphor-integrated nanoparticles.

MODE FOR CARRYING OUT THE INVENTION

The probe reagent of the present invention and FISH using the same will now be described.

<<Probe Reagent for FISH Comprising Phosphor-Integrated Nanoparticles>>

The probe reagent for FISH according to the present invention is a probe reagent for in situ hybridization which comprises: phosphor-integrated nanoparticles containing phosphors integrated therein; and a nucleic acid molecule having a prescribed nucleic acid sequence, the phosphor-integrated nanoparticles and the nucleic acid molecule being bound with each other.

[Nucleic Acid Molecule]

The nucleic acid molecule is one which has a sequence (probe sequence) containing a part or the entirety of a specific region of a chromosome. Examples of a nucleic acid include naturally-occurring nucleic acids such as DNAs and RNAs (e.g., mRNA, tRNA, miRNA, siRNA and non-cording-RNA), and artificial nucleic acids such as PNAs, LNAs and BNAs (Bridged Nucleic Acids). Accordingly, the nucleic acid molecule is not restricted as long as it is capable of forming a strand complementary to a nucleic acid sequence on a chromosome. The nucleic acid molecule may be a natural nucleic acid, an artificial nucleic acid, or a nucleic acid molecule in which a natural nucleic acid and an artificial nucleic acid are ligated.

As the probe sequence, the entirety or a part of a nucleic acid sequence on a chromosome that is associated with the detection of a biomarker gene such as HER2 is suitably used. Examples of a biomarker include diagnostic biomarkers, biomarkers for determination of disease stage, biomarkers for disease prognosis and monitoring biomarkers for observation of response to a therapeutic treatment. Examples of a gene related to the cancer growth or the efficiency of a molecular target drug include HER2, TOP2A, HER3, EGFR, P53 and MET. Further, the following genes are exemplified as genes that are known as cancer-related genes. Examples of tyrosine kinase-related genes include ALK, FLT3, AXL, FLT4 (VEGFR3), DDR1, FMS (CSF1R), DDR2, EGFR (ERBB1), HER4 (ERBB4), EML4-ALK, IGF1R, EPHA1, INSR, EPHA2, IRR (INSRR), EPHA3, KIT, EPHA4, LTK, EPHA5, MER (MERTK), EPHA6, MET, EPHA7, MUSK, EPHA8, NPM1-ALK, EPHB1, PDGFRα (PDGFRA), EPHB2, PDGFRβ (PDGFRB), PD-L1, BMI1, LGR5, EPHB3, RET, EPHB4, RON (MST1R), FGFR1, ROS (ROS1), FGFR2, TIE2 (TEK), FGFR3, TRKA (NTRK1), FGFR4, TRKB (NTRK2), FLT1 (VEGFR1) and TRKC (NTRK3). Further, examples of breast cancer-related genes include ATM, BRCA1, BRCA2, BRCA3, CCND1, E-Cadherin, ERBB2, ETV6, FGFR1, HRAS, KRAS, NRAS, NTRK3, p53 and PTEN. Examples of carcinoid tumor-related genes include BCL2, BRD4, CCND1, CDKN1A, CDKN2A, CTNNB1, HES1, MAP2, MEN1, NF1, NOTCH1, NUT, RAF, SDHD and VEGFA. Examples of colon cancer-related genes include APC, MSH6, AXIN2, MYH, BMPR1A, p53, DCC, PMS2, KRAS2 (or Ki-ras), PTEN, MLH1, SMAD4, MSH2, STK11 and MSH6. Examples of lung cancer-related genes include ALK, PTEN, CCND1, RASSF1A, CDKN2A, RB1, EGFR, RET, EML4, ROS1, KRAS2, TP53 and MYC. Examples of liver cancer-related genes include Axin1, MALAT1, b-catenin, p16 INK4A, c-ERBB-2, p53, CTNNB1, RB1, Cyclin D1, SMAD2, EGFR, SMAD4, IGFR2, TCF1 and KRAS. Examples of renal cancer-related genes include Alpha, PRCC, ASPSCR1, PSF, CLTC, TFE3, p54nrb/NONO and TFEB. Examples of thyroid cancer-related genes include AKAP10, NTRK1, AKAP9, RET, BRAF, TFG, ELE1, TPM3, H4/D10S170 and TPR. Examples of ovarian cancer-related genes include AKT2, MDM2, BCL2, MYC, BRCA1, NCOA4, CDKN2A, p53, ERBB2, PIK3CA, GATA4, RB, HRAS, RET, KRAS and RNASET2. Examples of prostate cancer-related genes include AR, KLK3, BRCA2, MYC, CDKN1B, NKX3.1, EZH2, p53, GSTP1 and PTEN. Examples of bone tumor-related genes include CDH11, COL12A1, CNBP, OMD, COL1A1, THRAP3, COL4A5 and USP6.

It is preferred that the probe sequence be designed to include a unique sequence contained in a specific region of a chromosome to be detected. Further, in cases where the copy number of a specific gene on a chromosome is detected by FISH, it is required to design the probe sequence taking into consideration the pre-splicing genome sequence containing introns. As for a method of obtaining a genome sequence containing a gene to be detected, the genome sequence can be searched in a public gene database DDBJ (DNA Data Bank of Japan) using an organism name, a gene name, a chromosomal number or, for example, "Cancer cell lines BACS", as a search word. For the detection of the copy number of a cancer (proto)gene by FISH, a sequence in the BAC clone library of "Cancer cell lines BACS" that contains a cancer (proto)gene sequence is preferred.

When a normal structural gene is to be detected, it is preferred that the probe sequence does not contain a part of a gene sequence having copy number polymorphism such as indel, VNTR (Variable Number of Tandem Repeat) or microsatellite. In human cells (2n=46), since the copy number of a normal gene per cell (nucleus) is 1 to 2, when the copy number estimated from the number of phosphor bright spots is 3 or larger, it can be judged that there is a chromosomal abnormality where the gene is amplified. On the other hand, when the copy number is 0, it can be judged that there is a chromosomal abnormality where the gene is deleted. When the probe sequence contains a sequence having such a gene polymorphism as described above, the number of phosphor bright spots does not agree with the copy number of a specific gene of interest, which is problematic in the detection of the copy number.

Further, for example, in cases where, as described below, a specific base (e.g., thymine (T)) in a nucleic acid molecule is substituted with a biotin-labeled nucleotide (e.g., biotin-16-dUTP in the above case) by nick translation and phosphor-integrated nanoparticles having streptavidin are bound to biotin at the sites of the substitution, since the number of the specific base (thymine (T) in the above case) in the nucleic acid molecule affects the number of bright spots and luminescence intensity in FISH, the probe sequence may be designed with determination of the specific base in the nucleic acid molecule while taking into consideration the number of bright spots and luminescence intensity. In cases where phosphor-integrated nanoparticles are bound to a nucleic acid molecule by a mode different from the above (for example, when phosphor-integrated nanoparticles are bound to only the 5'-end of a nucleic acid molecule), it is not necessary to take into consideration the number of a specific base in a probe sequence.

As for a method of obtaining a nucleic acid molecule, if the nucleic acid molecule has several tens of bases, the nucleic acid molecule is preferably obtained by submitting the sequence data thereof including a probe sequence and entrusting the production to a nucleic acid synthesis service offered by Funakoshi Co., Ltd. or the like. Meanwhile, when the nucleic acid molecule has a large number of bases (for example, in excess of 1,000 bases), although it is possible to obtain the nucleic acid molecule by the synthesis as described above, since it is time-consuming, for example, the nucleic acid molecule may be obtained as described below with a premise that proper formation of the nucleic acid molecule will be confirmed by sequencing of its base sequence. Probes that are designed and prepared by various methods in this manner are generally referred to as "DNA probe" when the nucleic acid sequence is DNA or "RNA probe" when the nucleic acid sequence is RNA.

In one method, primers are designed and synthesized in such a manner to sandwich a probe sequence part contained in the genomic DNA of an organism subjected to detection, and PCR is performed using a set of these primers and a pfu DNA polymerase having high replication accuracy for genomic DNA (or a genomic library such as the above-described BAC clone library). Then, the resulting PCR solution is separated by electrophoresis and a band corresponding to the length of a nucleic acid molecule of interest is cut out and eluted using a nucleic acid purification kit (e.g., MonoFas (registered trademark) DNA purification kit I), thereby the nucleic acid molecule of interest can be obtained.

In another method, a nucleic acid molecule of interest can be obtained by transforming a plasmid containing the sequence of the nucleic acid molecule (e.g., BAC plasmid) into *Escherichia coli* cells (e.g., *E. coli* HST08 Premium Electro-Cells (manufactured by Takara Bio Inc.), culturing (amplifying) and recovering the cells, extracting nucleic acids, cutting out a portion corresponding to the nucleic acid molecule using a prescribed restriction enzyme(s), and then performing electrophoresis and nucleic acid purification as described above.

Further, in a method of obtaining a nucleic acid molecule that is different from the above, a nucleic acid molecule can also be acquired by artificially synthesizing a probe (nucleic acid molecule) having a sequence that can be used as a probe with utilization of an artificial nucleic acid such as PNA, LNA or BNA (Bridged Nucleic Acid).

[Phosphor-Integrated Nanoparticles]

The phosphor-integrated nanoparticles are nanoparticles in which phosphors are integrated. By using such phosphor-integrated nanoparticles, the amount of fluorescence emitted per particle, that is, the brightness of a bright spot labeling a prescribed biomolecule, can be improved as compared to a case where the phosphors are used by themselves.

[Phosphor]

The term "phosphor" used herein generally refers to a substance that is excited when irradiated with an X-ray, ultraviolet radiation or visible light from outside and emits light during the transition from the excited state back to the ground state. Accordingly, regardless of the mode of transition from the excited state back to the ground state, the "phosphor" in the present invention may be a substance that emits fluorescence in a narrow sense, which is light emission associated with deactivation from an excited singlet state, or may be a substance that emits phosphorescence, which is light emission associated with deactivation from a triplet state.

Further, the "phosphor" in the present invention is not restricted by the emission lifetime after blocking of the excitation light. Thus, the "phosphor" may be a substance that is known as a light-storing substance, such as zinc sulfide or strontium aluminate. Such phosphors can be generally classified into organic phosphors (fluorescent dyes) and inorganic phosphors.

[Organic Phosphor]

Examples of an organic phosphor that can be used include substances known as organic fluorescent dyes, such as fluorescein-based dye molecules, rhodamine-based dye molecules, Alexa Fluor (registered trademark, manufactured by Invitrogen Corp.)-based dye molecules, BODIPY (registered trademark, manufactured by Invitrogen Corp.)-based dye molecules, Cascade (registered trademark, manufactured by Invitrogen Corp.)-based dye molecules, coumarin-based dye molecules, NBD (registered trademark)-based dye molecules, pyrene-based dye molecules, Texas Red (registered trademark)-based dye molecules, cyanine-based dye molecules, perylene-based dye molecules and oxazine-based dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7, 7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen Corp.), methoxycoumarin, eosin, NBD, pyrene, Cy5, Cy5.5 and Cy7. These organic phosphors may be used individually, or a plurality thereof may be used in combination.

[Inorganic Phosphor]

Examples of an inorganic phosphor that can be used include quantum dots containing a Group II-VI compound, Group III-V compound or Group IV element as a component (hereinafter, such quantum dots are also referred to as "Group II-VI quantum dot", "Group III-V quantum dot" and "Group IV quantum dot", respectively). These quantum dots may be used individually, or a plurality thereof may be used in combination. These quantum dots may also be commercially available ones.

Specific examples thereof include, but not limited to, CdSe, CdS, CdTe, ZnSe, ZnS, ZnTe, InP, InN, InAs, InGaP, GaP, GaAs, Si and Ge.

Quantum dots in which any of the above-described quantum dots is used as a core and a shell is provided thereon can also be used. Hereinafter, as a method of describing quantum dots having a shell, a quantum dot whose core is CdSe and shell is ZnS is indicated as "CdSe/ZnS". For example, CdSe/ZnS, CdS/ZnS, InP/ZnS, InGaP/ZnS, Si/SiO$_2$, Si/ZnS, Ge/GeO$_2$ and Ge/ZnS can be used; however, the quantum dot is not restricted thereto.

If necessary, a quantum dot whose surface has been treated with an organic polymer or the like may be used as well. Examples thereof include CdSe/ZnS having surface carboxy groups (manufactured by Invitrogen Corp.) and CdSe/ZnS having surface amino groups (manufactured by Invitrogen Corp.).

[Method of Producing Phosphor-Integrated Nanoparticles]

The method of producing the phosphor-integrated nanoparticles containing phosphors integrated therein is not particularly restricted, and they can be produced by a known method. Generally, a production method in which phosphors are put together using a resin or silica as a matrix (phosphors are immobilized inside or on the surface of the matrix) can be employed.

The particle size of the phosphor-integrated nanoparticles is not particularly restricted as long as their average particle size is in a range that allows fluorescence observation; however, from the standpoint of performing fluorescence observation in a preferred manner, the average particle size of the phosphor-integrated nanoparticles is preferably not smaller than 40 nm and not larger than 300 nm.

The average particle size of the thus produced phosphor-integrated nanoparticles can be measured by a method known in the art, examples of which include a gas adsorption method, a light scattering method, a small-angle X-ray scattering method (SAXS) and a method of measuring the average particle size by observation under a transmission electron microscope (TEM) or a scanning electron microscope (SEM). When a TEM is used and the particle size distribution is broad, it is necessary to pay attention to whether or not the particles in a field of view represent all of the particles. In an adsorption method, the BET surface area is evaluated by $N_2$ adsorption or the like.

<When Organic Phosphor is Used>

Examples of a method of producing phosphor-integrated nanoparticles using an organic phosphor include a method of forming resin particles having a diameter in the order of nanometers, in which resin particles a fluorescent dye that is a phosphor is immobilized inside or on the surface of a matrix made of a resin. The method of preparing such phosphor-integrated nanoparticles is not particularly restricted, and it is possible to employ, for example, a method in which a phosphor is added while (co)polymerizing (co)monomers for the synthesis of a resin (thermoplastic resin or thermosetting resin) constituting the matrix of phosphor-integrated nanoparticles and the phosphor is thereby incorporated inside or on the surface of the resulting (co)polymer.

As the thermoplastic resin, for example, polystyrene, polyacrylonitrile, polyfuran, or a resin equivalent thereof can be suitably used. As the thermosetting resin, for example, polyxylene, polylactic acid, glycidyl methacrylate, polymelamine, polyurea, polybenzoguanamine, polyamide, phenol resin, polysaccharide, or a resin equivalent thereof can be suitably used. A thermosetting resin, particularly a melamine resin is preferred because elution of the dye embedded in the dye resin can also be inhibited by processes such as dehydration, clearing and mounting where an organic solvent such as xylene is used.

For example, polystyrene nanoparticles in which an organic fluorescent dye (phosphor) is embedded can be prepared by the copolymerization method described in U.S. Pat. No. 4,326,008 (1982) where an organic dye having a polymerizable functional group is used, or by the method described in U.S. Pat. No. 5,326,692 (1992) where a fluorescent organic dye is impregnated into polystyrene nanoparticles.

Meanwhile, silica nanoparticles in which organic phosphors are immobilized inside or on the surface of a matrix made of silica can also be produced. As for a production method of such silica nanoparticles, reference can be made to the method of synthesizing FITC-containing silica nanoparticles described in Langmuir, Vol. 8, p. 2921 (1992). By using a desired fluorescent dye in place of FITC, a variety of fluorescent dye-containing silica nanoparticles can be synthesized.

<When Inorganic Phosphor is Used>

For this production method, reference can be made to the synthesis of CdTe-containing silica nanoparticles described in New Journal of Chemistry, Vol. 33, p. 561 (2009).

Further, examples of a method of producing phosphor-integrated nanoparticles that is different from the above-descried methods include a method of producing phosphor-integrated nanoparticles by treating silica nanoparticles with a silane coupling agent to perform terminal amination and then accumulating semiconductor nanoparticles as terminal carboxyl group-containing phosphors on the surfaces of the silica beads via amide bonds.

Examples of other method of producing phosphor-integrated nanoparticles include a method of forming glassy particles in which semiconductor nanoparticles are dispersed and immobilized by a combination of a reverse micelle method and a sol-gel method using, as a glass precursor, a mixture of an organoalkoxysilane that has an organic functional group showing good adsorption to the semiconductor nanoparticles at a molecular terminal and an alkoxide, and subsequently converting the thus formed glassy particles into phosphor-integrated nanoparticles.

Examples of other method of producing phosphor-integrated nanoparticles also include a method of producing phosphor-integrated nanoparticles by mixing amino group-terminated semiconductor nanoparticles and carboxyl group-terminated semiconductor nanoparticles in the presence of 1-ethyl-3-(3-dimethylaminopropyl)carbodiimide hydrochloride (EDC) and subsequently allowing the semiconductor nanoparticles to bind with each other via amide bonds.

Further, an aggregate in which inorganic phosphors are immobilized inside or on the surface of a matrix made of a resin can also be produced. For example, quantum dot-containing polymer nanoparticles can be prepared by the method described in Nature Biotechnology Vol. 19, p. 631 (2001) where quantum dots are impregnated into polystyrene nanoparticles.

[Binding of Nucleic Acid Molecule and Phosphor-Integrated Nanoparticles]

The binding between the nucleic acid molecule and the phosphor-integrated nanoparticles is not particularly restricted as long as it does not cause a problem in FISH, and the binding can be achieved by various bonds. The nucleic acid molecule and the phosphor-integrated nanoparticles are bound by either a direct binding method where the phosphor-integrated nanoparticles are directly bound to the nucleic acid molecule or an indirect binding method where the nucleic acid molecule and the phosphor-integrated nanoparticles are bound via bonds formed between biomolecules.

<Direct Binding Method>

Examples of the direct binding method include a method of binding a nucleic acid molecule and phosphor-integrated nanoparticles by substituting a hydroxyl group of phosphoric acid bound to the ribose C5 position at the 5'-end of the nucleic acid molecule or a hydroxyl group bound to the ribose C1 position at the 3'-end of the nucleic acid molecule with a thiol group (SH group) using a known thiol group-introducing reagent and subsequently allowing this nucleic acid molecule to react with the phosphor-integrated nanoparticles labeled with maleimide.

Specifically, the binding at the 5'-end in the former case is performed, for example, as follows. First, SH-GTP and terminal transferase are added to the nucleic acid molecule, and the resulting mixture is incubated at 37° C. for 30 minutes to introduce a thiol group to the 5'-end of the nucleic acid molecule. Then, the phosphor-integrated nanoparticles labeled with maleimide are added to a solution of this nucleic acid molecule, and the resultant is incubated at 65° C. for 30 minutes to ligate the nucleic acid molecule and the phosphor-integrated nanoparticles through coupling of the thiol group and maleimide group. This binding can be preferably performed using, for example, a kit "5' EndTag™ Nucleic Acid Labeling System" manufactured by Vector Laboratories, Inc. in accordance with its protocol.

The binding at the 3'-end in the latter case is also performed by the same reaction mechanism as the binding at the 5'-end, preferably using a kit "3' EndTag DNA Labeling System" manufactured by Vector Laboratories, Inc.

Examples of other method include a method of binding an alkynyl group-containing nucleic acid molecule obtained by alkyne modification of DNA through nick translation or terminal modification and azide group ($N_3$)-containing phosphor-integrated nanoparticles in the presence of a copper salt by azide-alkyne cycloaddition reaction (a method utilizing so-called click-chemistry). In this case, azidation of the phosphor-integrated nanoparticles can be performed using a known azidation reagent (diazo group transfer reagent). Such binding of a nucleic acid molecule and phosphor-integrated nanoparticles can be preferably performed using "Alkyne Phosphoramidite 5'-terminal" manufactured by Lumiprobe Corporation in accordance with its protocol (Lumiprobe Corporation, "Protocol: Click-Chemistry Labeling of Oligonucleotides and DNA", [online], [search date: Jan. 13, 2014], internet <URL; www.lumiprobe.com/protocols/click-chemistry-dna-labeling>).

Examples of other method also include a method of directly binding dUTP and phosphor-integrated nanoparticles. In this method, for example, first, "Amino-11-dUTP" manufactured by Lumiprobe Corporation and N-succinimidyl-S-acetylthioglycolate (SATA) are mixed to perform a thiol group addition treatment and, the resultant is then filtered through a gel filtration column to obtain a thiol-11-dUTP solution. Next, the phosphor-integrated nanoparticles having a maleimide group attached to a terminal and the thiol-11-dUTP solution are allowed to react with mixing in EDTA-containing PBS, as a result of which phosphor-integrated nanoparticles bound with dUTP can be obtained. Thereafter, by incorporating the thus obtained phosphor-integrated nanoparticles bound with dUTP into a nucleic acid molecule through nick translation, the phosphor-integrated nanoparticles can be directly bound to the nucleic acid molecule.

<Indirect Binding Method>

The indirect binding method is a method of binding a nucleic acid molecule and phosphor-integrated nanoparticles via bonds formed between biomolecules (first and second biomolecules). For example, when the bonds between biomolecules are bonds formed by streptavidin and biotin as the first and second biomolecules, respectively, the indirect binding is achieved by, for example, preparing a biotin-labeled nucleic acid molecule and phosphor-integrated nanoparticles modified with streptavidin and allowing them to bind with each other as described above.

Examples of a method of preparing a nucleic acid molecule labeled with the first biomolecule (e.g., biotin) include the followings.

(1) Nick Translation Method

For example, a method in which a specific base (e.g., thymine (T)) of a nucleic acid molecule is substituted with a first biomolecule (e.g., biotin)-labeled nucleotide (e.g., biotin-16-dUTP) by nick translation and phosphor-integrated nanoparticles having (strepto)avidin are subsequently bound to biotin of this nucleic acid molecule can be employed.

In this case, the nick translation can be performed using a biotin-labeled nucleotide (e.g., "biotin-16-dUTP" manufactured by Boehringer Ingelheim) in accordance with a conventional method (e.g., "Cell Engineering Supplement—Experimental Protocol Series: FISH Experimental Protocol", II. Chapter 2, supervised by Kenichi Matsubara et al., Gakken Medical Shujunsha Co., Ltd. 1994).

Examples of other method include the below-described methods of (2-1) and (2-2) where the first biomolecule (e.g., biotin) is introduced to a terminal (5'-end or 3'-end) of a nucleic acid molecule.

(2) 5'-End or 3'-End Labeling Method (2-1) Method Utilizing PCR

In the preparation of a probe (nucleic acid molecule) from a template by PCR method, by using primers having biotin-dNTP (wherein, N is any one of adenine (A), guanine (G), cytosine (C), thymine (T) and uracil (U)) at the 5'-end or 3'-end as primers used in the PCR method, a probe (nucleic acid molecule) labeled with the first biomolecule (e.g., biotin) at the 5'-end or 3'-end can be obtained. This probe is then allowed to react with phosphor-integrated nanoparticles having the second biomolecule (e.g., avidin), and the probe (nucleic acid molecule) and the phosphor-integrated nanoparticles can thereby be bound at a ratio of 1:1. As the template, a BAC clone or a genomic DNA of human or the like can be used as well.

(2-2) Method Utilizing Linker

Using a kit or the like, a first binding group (e.g., thiol group) is introduced to the 5'-end or 3'-end of a nucleic acid molecule and this nucleic acid molecule is subsequently allowed to undergo a binding reaction with a molecule which has a second binding group (e.g., maleimide group) capable of binding to the first binding group and contains the first biomolecule (e.g., biotin), as a result of which the 5'-end or 3'-end of the nucleic acid molecule can be labeled with the first biomolecule. By further allowing this nucleic acid molecule to react with phosphor-integrated nanoparticles having the second biomolecule (e.g., avidin), the probe (nucleic acid molecule) and the phosphor-integrated nanoparticles can be bound with each other.

Examples of the above-described molecule include a hydrophilic polymer (e.g. PEG) linker which has a maleimide group on one end and biotin on the other end. After allowing such a linker to bind to a thiol group at the 5'-end of a nucleic acid molecule and then allowing phosphor-integrated nanoparticles having streptavidin to bind to the biotin on the other end, the phosphor-integrated nanoparticles can be indirectly bound to the nucleic acid molecule.

Examples of the Kit Include "5' EndTag™ Nucleic Acid Labeling System".

As the linker, for example, the code PG2-BNML-10k, PG2-BNML-5k, PG2-BNML3k, PG2-BNML-2k or PG2-BNML-1k of "Biotin-PEG-Maleimide" (manufactured by Nanocs, Inc.) can be used.

(3) Non-Terminal Labeling Method

It is also possible to label the probe (nucleic acid molecule), which was prepared using primers having unlabeled terminals in accordance with the above-described method of (2-1) utilizing PCR, with a plurality of biotin molecules through reaction with "Platinum Bright Nucleic Acid Labeling Kit" (product number: GLK-007, manufactured by Funakoshi Co., Ltd.).

Meanwhile, phosphor-integrated nanoparticles modified with the second biomolecule (e.g., streptavidin) can be prepared by, for example, as follows. A functional group is introduced to each of phosphor-integrated nanoparticles and the second biomolecule using a functional group-introducing reagent, and the second biomolecule and the phosphor-integrated nanoparticles are bound via bonds formed between their functional groups. A linker may exist between the functional groups. Examples of the combination of the functional groups include NHS ester group-amino group and thiol group-maleimide group. Examples of the linker include EMCS (N-[ε-maleimidocaproyloxy]succinimide ester) (manufactured by Thermo Fisher Scientific K.K.).

<Binding of Nucleic Acid Molecule and Plural Phosphors>

In cases where plural phosphor-integrated nanoparticles are bound to a nucleic acid molecule to obtain other probe reagent of the present invention, this binding can be achieved by, for example, labeling a plurality of specific bases (e.g., thymine (T)) contained in the nucleic acid molecule with the first biomolecule (e.g., biotin) by nick translation as described above and subsequently allowing the second biomolecule (e.g., streptavidin)-labeled phosphors (e.g., phosphor-integrated nanoparticles modified with streptavidin) to bind to this biotin.

<Phosphor Labeling Ratio of Nucleic Acid Molecule>

The phosphor labeling ratio of a nucleic acid molecule is represented by: (Number of phosphor molecules bound to nucleic acid molecule/Total number of bases per nucleic acid molecule)×100(%).

This labeling ratio is not particularly restricted as long as it is in such a range that does not cause saturation of fluorescence signal and allows observation of bright spots under a fluorescence microscope in FISH. The labeling ratio is preferably 13.33% or lower, more preferably 0.46 to 13.33%. Particularly, as an example of a case where the labeling ratio is 0.46% or lower, there is a case where a single phosphor-integrated nanoparticle is bound to a terminal of a nucleic acid molecule. The lowest labeling ratio is attained in this case, and such a case where a nucleic acid molecule is fluorescently labeled with a single phosphor-integrated nanoparticle is preferable from the standpoints of reducing as much as possible the use of a phosphor-integrated nanoparticle that is not intrinsic to a nucleic acid molecule and thereby improving the reactivity of the nucleic acid molecule.

In cases were a nucleic acid molecule and a phosphor(s) are bound via an extremely specific streptavidin-biotin bond(s), specifically, in cases where, for example, some of the bases of a nucleic acid molecule are labeled with biotin while phosphors are labeled with streptavidin and the nucleic acid molecule is labeled with the phosphors via the biotin-streptavidin bonds, since streptavidin binds to all of the biotin contained in the nucleic acid molecule with high specificity, the below-described "biotin labeling ratio" is the same as the above-described phosphor labeling ratio of the nucleic acid molecule. With regard to the level of the biotin labeling ratio in the present invention, for convenience, a biotin labeling ratio of higher than 8% is said to be "high" and a biotin labeling ratio of less than 8% is said to be "low".

The biotin labeling ratio can be verified by, for example, a HABA-avidin method using "Thermo Scientific Pierce Biotin Quantitation Kit" (manufactured by Thermo Fisher Scientific K. K.) where, with HABA being bound to streptavidin of phosphor(s), HABA is substituted with biotin of the above-described BAC probe.

<Binding Molar Ratio of Phosphor-Integrated Nanoparticle>

The binding molar ratio of the nucleic acid molecule and the phosphor-integrated nanoparticle(s) is not particularly restricted as long as it is in such a range that does not cause saturation of fluorescence signal and allows observation of bright spots under a fluorescence microscope in FISH; however, the molar ratio (nucleic acid molecule:phosphor-integrated nanoparticle) is preferably 1:1 to 1:5,000, more preferably 1:1 to 1:2,000, still more preferably 1:1 to 1:550, yet still more preferably 1:1 to 1:100, yet still more preferably 1:1 to 1:40. At least one phosphor-integrated nanoparticle is required per nucleic acid molecule and, in order to allow observation of the fluorescence signal with adequate brightness, it is sufficient that 100 phosphors or phosphor-integrated nanoparticles be bound per nucleic acid molecule. Even when plural phosphors or phosphor-integrated nanoparticles are bound per nucleic acid molecule, they are observed as a single bright spot and the presence of a single copy of a gene to be detected is thereby determined.

A probe reagent having a molar ratio (the nucleic acid molecule:the phosphor-integrated nanoparticle) of 1:1 can be prepared by, for example, binding the phosphor-integrated nanoparticle to the 5'-end or 3'-end of the nucleic acid molecule as described above.

A probe reagent having a molar ratio (the nucleic acid molecule:the phosphor-integrated nanoparticle) of 1:2 can be prepared by binding the phosphor-integrated nanoparticle to the 5'-end and 3'-end of the nucleic acid molecule as described above.

For the preparation of a probe reagent having a molar ratio (the nucleic acid molecule:the phosphor-integrated nanoparticle) in a range of 1:3 to 1:5,000 (for example, 1:3 to 1:550), when the numbers of guanine (G), cytosine (C), thymine (T) and adenine (A) contained in the base sequence of the nucleic acid molecule are measured and there are 3 to 5,000 (in the above case, 3 to 550) of a certain base (e.g., thymine (T)), the nucleic acid molecule is subjected to nick translation with inclusion of its first biomolecule (e.g., biotin)-bound nucleotide substrate (in the above case, biotin-16-dUTP) so as to form a nucleic acid molecule having 3 to 5,000 (in the above case, 3 to 550) first biomolecules, and phosphor-integrated nanoparticles having the second biomolecule (e.g., streptavidin) can then be bound to the first biomolecules.

Alternatively, a probe reagent having a molar ratio (the nucleic acid molecule:the phosphor-integrated nanoparticle) in a range of 1:3 to 1:5,000 (in the above case, 1:3 to 1:550) can also be prepared in the same manner as described above by performing the nick translation using a nucleotide substrate conjugated with phosphor-integrated nanoparticles in place of the first biomolecule-bound nucleotide substrate.

Here, by changing the substrate concentration in the nick translation, the number of a specific base in the nucleic acid molecule to be labeled with the first biomolecule (e.g., biotin) or the like can be adjusted. Specifically, for example, when 300 thymines (T) are contained in a nucleic acid molecule and it is desired to substitute about 100 of them with biotin-16-dUTP, the ratio of the substitution can be adjusted by appropriately changing the ratio of dUTP and biotin-16-dUTP contained in the nucleotide substrate used in the nick translation.

Examples of a nucleotide substrate used for biotin labeling include the followings.

When biotin labeling is performed by substitution of adenine (ATP) in the nucleic acid molecule, biotin-11-dATP, biotin-14-dATP, Bio-7-dATP (biotin-7-2'-deoxyadenosine-5'-triphosphate), biotin-N6-ATP and the like can be used as the nucleotide substrate.

When biotin labeling is performed by substitution of cytosine (CTP) in the nucleic acid molecule, biotin-14- dCTP, biotin-11-dCTP and the like can be used as the nucleotide substrate. When biotin labeling is performed by substitution of thymine (TTP) in the nucleic acid molecule, biotin-16-dUTP, biotin-11-dUTP, biotin-aha-dUTP and the like can be used as the nucleotide substrate. Further, when biotin labeling is performed by substitution of guanine, biotin-11-dGTP and the like can be used as the nucleotide substrate.

The molar ratio (nucleic acid molecule:phosphor-integrated nanoparticle) of the thus synthesized probe reagent can be verified by, for example, subjecting the synthesized probe reagent to molecular weight fractionation through a gel filtration column to specify fractions that emit fluorescence upon irradiation of each fraction solution with a light having a wavelength that excites the phosphor-integrated nanoparticle (s), that is, fractions containing the phosphor-integrated nanoparticle (s), and measuring the absorbance (OD=260) of each fraction solution to specify fractions containing the nucleic acid molecule and to judge whether or not a fraction containing both the phosphor-integrated nanoparticle (s) and nucleic acid molecule is found at a fraction position of a molecular weight range that the probe reagent having a molar ratio of 1:3 to 1:100 can take theoretically. When a DNA probe that does not have a desired molar ratio is contained in the reagent, for removal of this DNA probe, only the fraction of a desired DNA probe can be recovered by the molecular weight fractionation.

Further, the molar ratio of the synthesized probe reagent (nucleic acid molecule:phosphor-integrated nanoparticle) can also be determined by a method different from the above. Specifically, in cases where the binding of the nucleic acid molecule and phosphor-integrated nanoparticle (s) is performed by utilization of streptavidin-biotin bond, the biotin labeling ratio of the nucleic acid molecule can be determined by a HABA-avidin method as described above and the molar ratio can be calculated by the following formula:

$$1:[\text{Total number of bases in nucleic acid molecule} \times \text{biotin labeling ratio (\%)}/100\%].$$

<<Semiconductor Nanoparticle-Containing FISH Probe Reagent>>

Other probe reagent for in situ hybridization according to the present invention is characterized in that 20,000 mol or more of semiconductor nanoparticles are bound with respect to 1 mol of a nucleic acid molecule having a prescribed nucleic acid sequence.

Semiconductor nanoparticles have a smaller particle size and thus a lower luminescence brightness per particle than the above-described phosphor-integrated nanoparticles; therefore, semiconductor nanoparticles are different from the phosphor-integrated nanoparticles in that, when FISH is performed using a probe reagent in which at least 20,000 mol of such semiconductor nanoparticles are bound with respect to 1 mol of a nucleic acid molecule as a FISH probe, the resulting bright spots can be observed not only by a confocal microscope but also by a fluorescence microscope.

Further, since semiconductor nanoparticles have a smaller particle size than the phosphor-integrated nanoparticles as described above, when FISH is performed using a probe obtained by binding such semiconductor nanoparticles and a nucleic acid molecule at a binding molar ratio in the above-described range, there is an advantage in that adverse effects on the hybridization between a target nucleic acid molecule (e.g., HER2 gene in a tissue section) and the probe can be reduced.

It is noted here, however, that bright spots may still be observable under a fluorescence microscope in the same manner as described above even when the number of moles of the semiconductor nanoparticles bound per 1 mol of the nucleic acid molecule is less than 20,000 (for example, 10,000 mol to less than 20,000 mol).

[Nucleic Acid Molecule]

With regard to this nucleic acid molecule, descriptions thereof are omitted here because the same nucleic acid molecule as described above for the phosphor-integrated nanoparticle-containing probe reagent can be used.

[Semiconductor Nanoparticle]

As the semiconductor nanoparticles, for example, the above-described quantum dots, specifically "Qdot (registered trademark)" (manufactured by Invitrogen Corp.) and the like can be used.

(Average Particle Size)

The particle size of the semiconductor nanoparticles is not particularly restricted as long as the average particle size is in a range that allows fluorescence observation under a fluorescence microscope when FISH is performed using a probe reagent in which the semiconductor nanoparticles and a nucleic acid molecule are bound at a binding molar ratio in the above-described range; however, from the standpoint of preventing the semiconductor nanoparticles from adversely affecting the hybridization between the nucleic acid molecule of the probe and the target gene to be detected (e.g., HER2 gene in a tissue section), the average particle size of the semiconductor nanoparticles is preferably 40 nm or smaller, more preferably 10 to 20 nm, which is smaller than that of the phosphor-integrated nanoparticles.

[Binding of Nucleic Acid Molecule and Semiconductor Nanoparticles]

The binding between the nucleic acid molecule and the semiconductor nanoparticles is not particularly restricted as long as it does not cause a problem in FISH, and the binding can be achieved by various bonds. The nucleic acid molecule and the semiconductor nanoparticles are bound by either a direct binding method where the semiconductor nanoparticles are directly bound to the nucleic acid molecule at a molar ratio in the above-described range or an indirect binding method where the nucleic acid molecule and the semiconductor nanoparticles are bound via bonds formed between biomolecules.

<Direct Binding Method>

Examples of the direct binding method include a binding method where nick translation is performed on a nucleic acid molecule using a nucleic acid substrate having a first binding group (e.g., maleimide) so as to introduce the first binding group to the nucleic acid molecule and this nucleic acid molecule is subsequently allowed to react with quantum dots having a second binding group (e.g., thiol group) capable of binding to the first binding group. As the nucleic acid substrate having a maleimide group (maleimide-dNTPs), for example, one which synthesized on commission and purchased from Nihon Gene Research Laboratories Inc. or the like can be used.

<Indirect Binding Method>

Examples of the direct binding method include a binding method where nick translation is performed on a nucleic acid molecule (particularly, a nucleic acid having 20,000 or more bases) using a nucleic acid substrate (e.g., the above-described dUTP-biotin) having a first biomolecule (e.g., biotin) so as to introduce the first biomolecule to the nucleic acid molecule and this nucleic acid molecule is subsequently allowed to react with quantum dots having a second biomolecule (e.g., streptavidin) capable of binding to the first biomolecule. In this case, the first and second biomolecules can be directly bound with each other, or they can be bound via a third molecule or substance.

<Binding Molar Ratio of Semiconductor Nanoparticles>

As for the binding molar ratio of the nucleic acid molecule and the semiconductor nanoparticles, by binding at least 20,000 mol of the semiconductor nanoparticles per 1 mol of the nucleic acid molecule, when FISH is performed using a FISH probe reagent containing the semiconductor nanoparticles, such brightness that allows observation of sufficient number of bright spots even under a fluorescence microscope can be ensured.

[FISH]
[Staining Method]

FISH will now be described. FISH is not particularly restricted and a known method can be employed. The following descriptions pertain to one embodiment of the present invention.

<Preparation of Specimen Slide>

A specimen slide can be prepared by, for example, a method used for general histopathological diagnosis of a tissue of a test subject (e.g., human, dog or cat) suspected of having a cancer. First, the tissue of the test subject is fixed with formalin or the like and dehydrated with alcohol. The tissue is then treated with xylene and embedded in paraffin by immersion in high-temperature paraffin to prepare a tissue sample. Subsequently, this tissue sample is cut into a 3 to 4-μm section and placed on a glass slide to prepare a specimen slide (see FIGS. 2 and 3).

<Deparaffinization>

The tissue section on the specimen slide is immersed in xylene or other deparaffinization agent contained in a vessel to remove paraffin (see FIGS. 2 and 3). The temperature of this process is not particularly restricted and may be room temperature. The immersion time is preferably 3 minutes or longer but not longer than 30 minutes. As required, xylene may be replaced during the immersion. Subsequently, the section is immersed in ethanol contained in a vessel to remove xylene. The temperature of this process is not particularly restricted and may be room temperature. The immersion time is preferably 3 minutes or longer but not longer than 30 minutes. As required, ethanol may be replaced during the immersion. Then, the section is further immersed in water contained in a vessel to remove ethanol. The temperature of this process is not particularly restricted and may be room temperature. The immersion time is preferably 3 minutes or longer but not longer than 30 minutes. As required, water may be replaced during the immersion.

<Pretreatment of Specimen Slide>

In order to allow a probe reagent to reach nucleic acids on a tissue section in an efficient manner, it is known to subject the tissue section to a pretreatment (s), such as a heating treatment, an acid treatment, an enzyme treatment and/or an activator treatment, prior to hybridization reaction with a BAC probe or a probe shorter than a BAC probe (e.g., a BAC clone-derived probe). As for the conditions and combination of these treatments, since the optimum conditions are variable depending on the type and thickness of the section, the conditions for slide preparation and the like, it is required to determine the procedures of these treatments as appropriate. It is not always necessary to perform all of these treatments and, for example, it may be selected not to perform an enzyme treatment.

First, in accordance with a known method, the cellular tissue on which FISH is to be performed is activated. The activation conditions are not particularly defined here; however, as an activation liquid, for example, a 0.01M citrate buffer (pH 6.0), 1 mM EDTA solution (pH 8.0), 5% urea or 0.1 M Tris-HCl buffer can be used. As a heating equipment, for example, an autoclave, a microwave oven, a pressure cooker or a water bath can be used. The temperature of this process is not particularly restricted and may be room temperature. The activation can be performed at a temperature of 50 to 130° C. for a period of 5 minutes to 30 minutes.

In a treatment with a protein-removing reagent, a reagent containing an enzyme or hydrochloric acid is generally used and, for example, proteins of cell membranes and nuclear membranes are removed by the following procedures.

First, the specimen slide is immersed in hydrochloric acid (about 0.2 mol/L) for a certain time. The specimen slide is further immersed in water and then in a washing buffer (2×SSC: standard saline citrate) for washing. Next, the specimen slide is immersed in a pretreatment liquid (e.g., 1N NaSCN) for a certain time. Thereafter, the specimen slide is immersed in water and then in a washing buffer to be washed, and the same operations are repeated twice.

In cases where an enzyme is used as the protein-removing reagent, in order to degrade the proteins, particularly collagen, of cell membranes and nuclear membranes, for example, a treatment of the following procedures is performed. First, the specimen slide is immersed in a protease solution for a certain time. The specimen slide is then washed by immersion in a washing buffer, and this operation is repeated twice. Thereafter, the specimen slide is dried by air-drying or the like.

As the enzyme, for example, proteinase, pepsin or proteinase K is often used. A typical acid treatment is performed with 0.02 to 0.2N HCl, followed by washing at a high temperature (e.g., 70° C.). As for the efficiency of the deproteinization, taking into consideration the combination of proteinase concentration and degradation time that maximizes hybridization, that is, reaction with a target chromosome, the deproteinization is performed by setting such conditions that do not impair the morphological details. It is noted here that the optimum conditions are variable depending on the tissue type and the fixation method. Further, it is useful to perform additional fixation after the proteinase treatment.

<Fixation>

As required, after each pretreatment step such as the above-described enzyme treatment, in order to fix the specimen slide, for example, a treatment of the following procedures is performed. First, the specimen slide is immersed in a formalin solution for a certain time. Then, the specimen slide is washed by immersion in a washing buffer, and this operation is repeated twice. Thereafter, the specimen slide is dried by air-drying or the like.

<DNA Denaturation>

After the above-described fixation, in order to denature the DNA existing on the section (from double-stranded DNA into single-stranded DNA), for example, a treatment of the following procedures is performed. First, the specimen slide is immersed in a denaturation solution (e.g., a formamide/SSC solution) at about 72° C. for a prescribed time. Then, after taking out the specimen slide, in order to remove formamide, the specimen slide is immersed in gradually increasing concentrations of ethanol in several steps (for example, a 70% aqueous ethanol solution, a 80% aqueous ethanol solution and then 100% ethanol). Thereafter, the specimen slide is dried by air-drying or the like.

<Hybridization Using Probe Reagent>

Using the above-described probe reagent, hybridization can be performed in the same manner as in a known FISH method (e.g., "Agilent FISH General Purpose Reagents Protocol" or "Clinical FISH Protocol—Visualization of Chromosomal/Genetic Diagnosis (Cell Engineering Supplement—Experimental Protocol Series)") (see FIGS. 2 and 3). The term "hybridization" used herein means a process of binding two DNAs or a DNA and an RNA complementary strand for the formation of a double-stranded molecule, or the resulting double-stranded molecule.

Here, after hybridizing a nucleic acid molecule having a first biomolecule (e.g., biotin) to a specific nucleic acid sequence on a chromosome, fluorescent labeling may be performed in the reaction system by adding thereto phosphor-integrated nanoparticles having a second biomolecule capable of specifically binding to the first biomolecule (see FIG. 3).

As for the setting of the hybridization conditions, the accuracy of the binding of a nucleic acid molecule to a sequence on a chromosome varies depending on the GC content of a probe sequence, the concentration (M) of monovalent cations in the hybridization reaction system and the formamide concentration in the reaction system When the monovalent cation concentration (M) is 0.1 to 0.4 M, the Tm value of a probe sequence (≈Tm value of a nucleic acid molecule) is determined by the following formula (1):

$$Tm=16.6 \log M+0.41\times(GC)+81.5-0.72\times(\% \text{ formamide})$$

When the monovalent cation concentration (M) is higher than 0.4 M, the Tm value of a probe sequence (≈Tm value of a nucleic acid molecule) is determined by the following formula (2):

$$Tm=81.5+0.41\times(GC)-0.72(\% \text{ formamide})$$

Further, when setting the conditions, a reference can be made to Leitch at al. In situ Hybridization: a practical guide, Oxford BIOS Scientific Publishers, Microscopy Handbooks Vol. 2 (1994), which describes general conditions of in situ hybridization. Generally speaking, the background signal can be reduced by adopting high stringency conditions; however, the sensitivity is also reduced at the same time.

<Nuclear Staining>

After the hybridization, usually, nuclear staining is further preformed for counting the number of cells. As a nuclear staining reagent, DAPI is commonly used; however, a bisbenzimide derivative such as Hoechst 33258 or Hoechst 33342 or other nuclear staining reagent may be used as well. For example, when DAPI is used as a nuclear staining reagent, nuclear staining can be performed by the following procedures. First, the thus hybridized specimen slide is sequentially washed with deionized water and phosphate-buffered physiological saline (PBS). Then, the specimen slide is immersed in a DAPI staining reagent (2 µg/PBS) for a certain time.

<Mounting Treatment>

After the staining and nuclear staining by FISH, the resulting specimen slide is washed with PBS several times and air-dried or dehydrated. Subsequently, a mounting treatment is performed by dropping a mounting medium onto the tissue section, placing a cover glass thereon and then drying. The mounted specimen slide prepared by the above treatment is used as a preparation for pathological diagnosis and the like.

[Observation]

For the stained section, the number of fluorescent bright spots or the luminescence brightness is measured on a wide-field microscope image taken under a fluorescence microscope. An excitation light source and an optical filter for fluorescence detection, which conform to the maximum absorption wavelength and fluorescence wavelength of the fluorescent substance in use are selected. For the measurement of the number of bright spots or the luminescence brightness, a commercially available image analysis software, such as automatic total bright spot measuring software "G-Count" manufactured by G-Angstrom K.K., can be used. The image analysis using a microscope per se is well-known and, for example, the method disclosed in JP-A-H9-197290 can be employed. The size of the visual field of the microscope image is preferably 3 mm$^2$ or larger, more preferably 30 mm$^2$ or larger, still more preferably 300 mm$^2$ or larger. The copy number of a specific gene of interest is evaluated based on the number of bright spots and/or the luminescence brightness that are determined from the microscope image. Specifically, for example, a copy number of 1 to 2 is normal and occurrence of abnormality (abnormal growth) can be evaluated with a copy number of 3 or larger.

The actions and effects of the probe reagent of the present invention and FISH using the same will now be described.

(1) According to the probe reagent of the present invention, since it has a constitution in which a nucleic acid molecule (e.g., BAC probe) or a probe (e.g., BAC clone-derived probe) that is shorter and has an equivalent or lower labeling ratio as compared to a BAC probe is bound and labeled with phosphor-integrated nanoparticles having an improved luminescence brightness by integration of phosphors therein, even when the probe reagent has a labeling ratio equivalent to or lower than that of a conventional BAC probe, the probe reagent can increase the luminescence brightness to a level that is not lower than the luminescence brightness provided by a conventional BAC probe having a high labeling ratio, and the probe reagent thus enables to simultaneously detect even those bright spots that are located in a deeper layer of a tissue section. Moreover, the probe reagent allows a tissue section slide subjected to FISH to maintain bright spots in a detectable state over a longer period of time.

(2) As long as the phosphor-integrated nanoparticles have an average particle size of 40 nm to 300 nm, bright spots can be preferably observed when FISH is performed. Further, by controlling the average particle size of the phosphor-integrated nanoparticles to be in a range of 40 nm to 300 nm, the luminescence brightness of the bright spots can be preferably adjusted.

(3, 4) As long as the nucleic acid molecule is bound with the phosphor-integrated nanoparticles or phosphors at a molar ratio of 1:1 to 1:5,000 (particularly 1:1 to 1:40), the effects of the phosphor-integrated nanoparticles labeling the nucleic acid molecule on hybridization can be suppressed and bright spots can be preferably observed when FISH is performed. Moreover, the luminescence brightness of bright spots can be largely adjusted based on this molar ratio. Here, adjustments of the molar ratio and the average particle size of the phosphor-integrated nanoparticles make it easier to adjust the bright spots to have a desired luminescence brightness.

(5, 6) Further, in the probe reagent for in situ hybridization that is obtained by binding phosphor-integrated nanoparticles containing phosphors integrated therein to a nucleic acid molecule having a prescribed nucleic acid sequence of 5,000 or less bases, particularly 4,000 or less bases in accordance with a nucleic acid terminal labeling method, the labeling ratio is lower than a case where the entirety of the nucleic acid molecule is labeled by nick translation (the phosphor-integrated nanoparticles are bound only to one or both of the terminals of the nucleic acid molecule); therefore, a probe in which the effects of the phosphor-integrated nanoparticles labeling the nucleic acid molecule having a relatively small number of bases on hybridization are minimized can be prepared, and the luminescence brightness can be improved to an equivalent or higher level than the luminescence brightness provided by a conventional BAC probe.

Here, when labeling the nucleic acid molecule with biotin by nick translation using a biotin-labeled nucleic acid substrate, the labeling ratio can be reduced by adjusting the amount of the biotin-labeled nucleic acid substrate to be used; therefore, the above-described nucleic acid molecule having a low labeling ratio may also be obtained by such a method.

(7) As long as the above-described probe reagent has a phosphor labeling ratio (%) of not higher than 13.33% against a nucleic acid molecule, from the same standpoints of (5,6), FISH can be preferably performed using the probe reagent.

(8, 9) As long as the phosphor-integrated nanoparticles are particles formed from a resin, not only phosphors are easily incorporated and thus integrated therein while polymerizing monomers in the production of the resin particles, but also the average size of the resin particles and the brightness of light emitted from the resin particles can be adjusted by changing the polymerization conditions in the synthesis of the resin particles (e.g., concentrations of the phosphors and monomers contained in a polymerization solution and polymerization temperature). Here, when the resin particles are formed from a thermosetting resin such as a melamine resin, the phosphors are unlikely to elute from the resin particles and fading of the phosphor-integrated nanoparticles can be inhibited. Consequently, fading of bright spots on a specimen slide can be inhibited.

(10, 11) Here, when the first and second biomolecules are molecules that are capable of specifically binding to each other, such as streptavidin and biotin, since the nucleic acid molecule is bound with the phosphor-integrated nanoparticles or the phosphors via extremely specific bonds, the post-hybridization fluorescent staining can be preferably performed.

(12) In the probe reagent in which the phosphor-integrated nanoparticles are directly bound to the bases of the nucleic acid molecule, the first and second biomolecules are not used; therefore, even when a cellular tissue to be stained by a FISH method has the first and second biomolecules that are endogenous to the cellular tissue itself, the probe reagent does not bind to these biomolecules.

(13, 15-17) According to the probe reagent kit for FISH that separately comprises: a nucleic acid molecule which is linked with a first biomolecule and has a sequence of a BAC probe (of 150,000 or less bases, particularly 4,000 or less bases) having a low labeling ratio or a probe (e.g., BAC clone-derived probe) that is shorter and has an equivalent or lower labeling ratio as compared to a BAC probe, which sequence is complementary to the sequence of a specific region on a chromosome; and phosphor-integrated nanoparticles to which a second biomolecule capable of specifically binding to the first biomolecule is linked, at any time point after hybridization by FISH using the nucleic acid molecule linked with the first biomolecule as a probe but before observation, the chromosome can be fluorescently stained by adding the phosphor-integrated nanoparticles linked with the second biomolecule or the phosphors to the hybridization system. This consequently enables to keep the phosphors in an environment where fading thereof is least likely to occur during the hybridization and to add the phosphors immediately before observation; therefore, a reduction in the luminescence brightness of the bright spots can be minimized. Moreover, since the hybridization is performed using a DNA probe in which the phosphor-integrated nanoparticles or phosphors are not bound to the nucleic acid molecule, there is an advantage in that the optimum conditions of the hybridization are unlikely to change.

(14, 18) Here, when the nucleic acid molecule is labeled with the first biomolecule at one or both of its terminals and/or 1 to 50 spots other than the terminals, the above-described effects on hybridization can be reduced as compared to a case where the first biomolecule is bound to the entire nucleic acid molecule.

(19) According to the probe reagent for in situ hybridization in which 20,000 mol or more of fluorescent nanoparticles (e.g., semiconductor nanoparticles or quantum dots (such as Q-dot)) are bound per 1 mol of a nucleic acid molecule having a prescribed nucleic acid sequence, when FISH is performed using this probe reagent, bright spots can be observed even under a fluorescence microscope.

EXAMPLES

Example 1

Preparation of BAC Probe Having Biotin Labeling Ratio of 13.3%

In accordance with the method described in Cell Biochem. Biophys. 2006; 45(1):59, a nucleic acid molecule was prepared as described below. For 1 µg (5 µL) of a HER2-DNA clone (about 150 kbp) purchased from GSP Lab., Inc., dTTP of the HER2-DNA clone (nucleic acid molecule) was substituted with biotin-labeled dUTP by a nick translation method as described below in accordance with the protocol provided with a nick translation kit (product name: "GSP-nick translation kit" K-015; manufactured by GSP Lab., Inc.).

[Standard Biotin Labeling Method by Nick Translation]

First, the following reagents were mixed in a centrifuge tube:

10× Nick Buffer (Tris-HCl [pH 7.2], MgSO$_4$, DTT): 2.5 µL

BSA (nuclease-free BSA): 1.5 µL dNTP mix (dATP, dCTP, dCTP): 5 µL dTTP: 0.5 µL

Biotin-16-dUTP (product number: 1093070, manufactured by Roche, 50 nmol/50 µL): 1.5 µL pure water (nuclease-free water): 3 µL an aqueous solution containing 1 µg of the above-described HER2-DNA clone of about 150-kbp: 5 µL DNA polymerase I (Tris-HCl [pH7.5], EDTA, DTT, glycerol): 1 µL DNAse I: 5 µL Next, the resulting mixture was allowed to react at 15° C. for 4 hours, and the reaction was terminated by heating the mixture at 70° C. for 10 minutes. Then, 25 µL of distilled water was added to the centrifuge tube. The resulting reaction solution of a biotin-labeled BAC probe was purified using a micro-spin column for nucleic acid purification ("MicroSpin S-200HR Column" manufactured by GE Healthcare, product number: "#27-5120-01").

To this solution, about 5.56 µL of 3 M sodium acetate solution (pH 5.2) and 150 µL of 100% ethanol were added, and the resultant was left to stand at −20° C. for at least one hour and subsequently centrifuged at 4° C. and 16,000 rpm for 10 minutes to form precipitates. Further, 500 µL of 70% ethanol was added and the resultant was centrifuged at 4° C. and 16,000 rpm for 1 minute, followed by removal of the resulting supernatant. Then, 5 to 10 µL of distilled water was added to the thus formed precipitates and the precipitates were completely dissolved, thereby obtaining a solution of a biotin-labeled BAC probe having a final concentration of 1 µg/250 µL.

[Preparation of DNA Probe in which Fluorescent Particles (Q-Dot) and BAC Probe Having Biotin Labeling Ratio of 13.3% are Bound]

The biotin-labeled BAC probe obtained above by nick translation in an amount of 25 µL (concentration: 1 µg/250 µL) and a solution containing 1.0 µL (50 nmol/50 µL) of Q-dot (registered trademark, manufactured by Quantum Dot Corporation) having a streptavidin-modified surface and an average particle size of 15 nm were mixed to perform binding reaction at room temperature for 30 minutes, thereby obtaining a DNA probe for HER2 detection (probe reagent A).

As for the verification of the binding molar ratio of the BAC probe and biotin, the binding molar ratio was determined to be 1:20,000 by a HABA-avidin method using "Thermo Scientific Pierce Biotin Quantitation Kit" (manufactured by Thermo Fisher Scientific K.K.) where, with HABA being bound to streptavidin of Q-dot, HABA was substituted with biotin of the BAC probe.

[Verification of DNA Probe]

The thus obtained DNA probe was verified by an electrophoretic shift assay where the DNA probe in a 0.5% modified Tris-borate-EDTA (TBE) buffer was electrophoresed through a 0.5% TBE-containing 2% agarose gel. Single-stranded DNA was counter-stained with SYBR Green II (Molecular Probes, Eugene, Oreg.). Then, the migration patterns of Q-dots and DNA were determined as described below using "MultiImager FX System" (Bio-Rad, Hercules, Calif.).

That is, Q-dots existing in the electrophoresed gel were checked using a green laser light having a wavelength of 532 nm as an excitation light along with a 640-nm bandpass emission filter. The SYBR Green II-stained DNA was checked using a blue laser light having a wavelength of 488 nm along with a 530-nm green bandpass emission filter.

[Storage of DNA Probe]

The DNA probe obtained in the above-described manner was diluted with a hybridization buffer (25% deionized formamide, 2×SSC, 200-ng/µL salmon sperm DNA, 5×Denhardt's solution, 50 mM sodium phosphate, pH 7.0, 1 mM EDTA) to a final concentration of 1 to 5 ng/µL. As required, free ligands (substrates of free streptavidin, biotin and dATP) were removed using a S300-sized spin column (Amersham Biosciences, Piscataway, N.J.). The DNA probe was freeze-stored at −20° C. when it was not used immediately.

[FISH]

The copy number of the HER2 gene was measured by FISH. As described below, FISH was carried out by performing deparaffinization, pretreatment of specimen slide, enzyme treatment, fixation of specimen, probe preparation, denaturation of DNA on specimen slide, hybridization, washing of glass slide and DAPI staining in the order mentioned.

[Deparaffinization]

A slide of HER2-positive staining control specimen ("HER2-FISH Control Slide" manufactured by Pathology Institute Corp., code: PS-09006) was deparaffinized by sequentially performing the following treatments (1) to (4): (1) immersing the specimen slide in Hemo-De at normal temperature for 10 minutes; (2) immersing the specimen slide in fresh Hemo-De at normal temperature for 10 minutes, followed by three repetitions of the same operation; (3) immersing the specimen slide in 100% ethanol at room temperature for 5 minutes and washing the specimen slide twice, followed by dehydration; and (4) drying the specimen slide in the air or on a 45 to 50° C. slide warmer.

[Pretreatment of Specimen Slide]

In order to improve the reachability of the DNA probe, the specimen slide was pretreated by sequentially performing the following operations (1) to (6) to remove the proteins of cell membranes and nuclear membranes: (1) treating the specimen slide with 0.2 mol/L HCl at room temperature for 20 minutes; (2) immersing the specimen slide in purified water for 3 minutes; (3) immersing the specimen slide in a washing buffer (2×SSC: standard saline citrate) for 3 minutes; (4) immersing the specimen slide in a pretreatment solution (1N NaSCN) at 80° C. for 30 minutes; (5) immersing the specimen slide in purified water for 1 minute; and (6) immersing the specimen slide in a washing buffer (2×SSC) for 5 minutes, followed by two repetitions of this immersion operation.

[Enzyme Treatment]

The thus pretreated specimen slide was subjected to an enzyme treatment by sequentially performing the following operations (1) to (4): (1) taking out the thus pretreated specimen slide and removing excess washing buffer by bringing the lower end of the glass slide into contact with a paper towel; (2) immersing the specimen slide in a protease solution heated to 37° C. for 10 to 60 minute, which immersion process is desirably performed with 25 mg protease (in 50 mL of 2,500 to 3,000 units/mg of pepsin/1M NaCl [pH 2.0] at 37° C. for 60 minutes) so as to degrade the proteins, particularly collagen, of cell membranes and nuclear membranes; (3) immersing the specimen slide in a washing buffer for 5 minutes, followed by two repetitions of this operation; and (4) drying the specimen slide in the air or on a 45 to 50° C. slide warmer for 2 to 5 minutes.

[Fixation of Specimen]

For fixation of the specimen, the pretreated specimen slide was subjected to the following treatments (1) to (3): (1) immersing the specimen slide in 10% neutral buffered formalin (4% paraformaldehyde-phosphate buffer" manufactured by Wako Pure Chemical Industries, Ltd., product number: 163-20145) at normal temperature for 10 minutes; (2) immersing the specimen slide in a washing buffer for 5 minutes, followed by two repetitions of the same operation; and (3) drying the specimen slide in the air or on a 45 to 50° C. slide warmer for 2 to 5 minutes.

[Probe Preparation]

A freeze-stored solution of the DNA probe (probe reagent A) was thawed back to room temperature and the viscosity of the solution was sufficiently reduced to such a level at which an exact volume of the solution can be collected by pipette operation, after which the solution was mixed using a vortex mixer or the like.

[Denaturation of DNA on Specimen Slide]

For denaturation of DNA on the specimen slide, the thus specimen-fixed specimen slide was subjected to the following treatments (1) to (8): (1) prior to the preparation of the specimen slide, placing and preheating a moist box having a water-moistened paper towel on the bottom (a hermetic container whose side surfaces are taped with paper towel) in a 37° C. incubator; (2) confirming that a denaturation solution (70% formamide/SSC [150 mM NaCl, 15 mM sodium citrate]) has a pH of 7.0 to 8.0 at normal temperature, placing the denaturation solution in a Coplin jar and heating the Coplin jar in a warm water bath until the solution temperature reaches 72° C.±1° C. (leaving the Coplin jar in a 72±1° C. warm water bath for at least 30 minutes); (3) marking a region on the back side of the specimen with a circle using a diamond pen or the like to clearly indicate a hybridization region; (4) immersing the specimen slide in the 72±1° C. denaturation solution placed in the Coplin jar to denature the DNA on the specimen slide; (5) taking out the specimen slide from the denaturation solution using a forceps, immediately placing the specimen slide in 70% ethanol at room temperature, shaking of the slide for removal of formamide and leaving the specimen slide immersed for 1 minute; (6) taking out the specimen slide from the 70% ethanol, placing the specimen slide in 85% ethanol, shaking the slide for removal of formamide and leaving the specimen immersed for 1 minute, followed by two repetitions of the same operations using 100% ethanol; (7) removing ethanol by bringing the lower end of the specimen glass slide into contact with a paper towel, and then wiping the back side of the glass slide with a paper towel; and (8) air-drying the specimen slide using a dryer or drying the specimen slide on a 45 to 50° C. slide warmer for 2 to 5 minutes.

[Hybridization]

The thus denaturation-treated specimen slide was subjected to hybridization with 10 μL (10 to 50 ng) of the above-prepared DNA probe by sequentially performing the following treatments (1) to (3): (1) adding 10 μL of the above-prepared DNA probe to the hybridization region of the specimen slide and immediately placing a 22 mm×22 mm cover glass over the probe to uniformly spread the probe while preventing air bubbles from entering the hybridization region; (2) sealing the cover glass with paper bond; and (3) placing the specimen slide in the previously heated moist box, placing the lid and then performing hybridization in a 37° C. incubator for 14 to 18 hours.

[Washing of Glass Slide]

The thus hybridized specimen slide was washed by sequentially performing the following treatments (1) to (6): (1) placing a post-hybridization washing buffer (2×SSC/ 0.3% NP-40) in a Coplin jar and preheating the Coplin jar in a warm water bath until the temperature of the post-hybridization washing buffer reaches 72° C.±1° C. (leaving the Coplin jar in a 72±1° C. warm water bath for at least 30 minutes); (2) preparing another Coplin jar containing the post-hybridization washing buffer and maintaining it at normal temperature; (3) removing the paper bond seal using a forceps; (4) immersing the specimen slide in this post-hybridization washing buffer until the cover glass spontaneously comes off in the solution; (5) taking out the specimen slide from the solution, removing excess solution and then immersing the specimen slide in the post-hybridization washing buffer heated to 72±1° C. for 2 minutes, which immersion treatment is desirably performed at a temperature of 73° C. or lower for a period of 2 minutes or less; and (6) taking out the specimen slide from the Coplin jar and air-drying the specimen slide in shade (for example, in a closed drawer or on a shelf of a closed cabinet).

[DAPI Staining]

DAPI staining was performed as follows. First, 10 μL of a DAPI counter-staining liquid was added to the hybridization region of the specimen slide. Next, after subjecting the specimen slide to hybridization, in order to count the number of cells, cell nuclei were stained by performing DAPI staining (2 μg/mL PBS) at 25° C. for 10 minutes, and a cover glass was placed on the specimen slide. The specimen slide was stored in shade until signal measurement. As DAPI (4',6-diamidino-2-phenylindole dihydrochloride), "D1306" manufactured by Molecular Probes Inc. was used.

[Observation]

<Bright-Field Observation>

For the above-prepared specimen slide, a first immunostained image was obtained using a light microscope ("Imager" manufactured by Carl Zeiss AG).

<Confocal Fluorescence Microscope Observation>

For the specimen slide prepared and subjected to FISH as described above, using a confocal microscope Zeiss LSM780 (manufactured by Carl Zeiss Microscopy GmbH), Q-dots of the hybridized DNA probe was excited and the fluorescence emitted from Q-dots was detected at a measurement wavelength of 655 nm to measure the fluorescence, obtain fluorescence images (static fluorescence images) and determine the number of bright spots. It is noted here that the images were each taken by changing the focal depth at 3.6 μm, 3.15 μm and 2.7 μm.

<Fluorescence Microscope Observation>

For fluorescence microscope observation, the section subjected to FISH as described above was observed (at ×600 magnification) under a fluorescence microscope Zeiss Imager (camera: MRm monochrome camera with cooling function, objective lens: ×60 oil immersion lens) to measure the fluorescence, obtain fluorescence images (static fluorescence images) and determine the number of bright spots.

Since Q-dots cause blinking (flickering) which is a phenomenon unique to Q-dots, not all of Q-dots emit fluorescence at the moment (e.g. 1/60 second) of taking an image in the fluorescence microscope observation. A change in the fluorescence intensity depending on the fluorescence measuring method may result in a case where such fluorescence naturally measured only by a non-confocal fluorescence microscope is not measured. One particle of Q-dot has about 4 seconds of off-state (no-fluorescence state) during an irradiation period of 20 seconds. Thus, after irradiating the excitation light as described above, 100 sequence static fluorescence images were taken at a resolution of 200 to 400 milliseconds using a 690-nm to 730-nm bandpass filter to produce a dynamic fluorescence image (200 to 400 ms/frame×100 images). The number of bright spots was measured throughout the time line of the dynamic fluorescence image. This measurement method was carried out in the same manner also in the microscope observation using a confocal unit.

<Results and Discussion>

In the fluorescence microscope observation, by adjusting the focus in the depth direction along a cross-section of the specimen slide, bright spots at deep positions were verified.

Reference Example 1

Preparation of BAC Probe Having Biotin Labeling Ratio of 13.3%

A solution of biotin-labeled 150,000-base BAC probe (nucleic acid molecule) having a final concentration of 1 μg/250 μL was obtained by the same procedures as in Example 1.

<Preparation of DNA Probe in which Fluorescent Dyes and BAC Probe Having Biotin Labeling Ratio of 13.3% are Bound>

The thus obtained biotin-labeled BAC probe in an amount of 25 μL (concentration: 1 μg/250 μL) and a solution containing 1.0 μL (50 nmol/50 μL) of FITC-modified streptavidin (Streptavidin, FITC Conjugate (1 mg, SA-5001, manufactured by Funakoshi Co., Ltd.)) were mixed to perform binding reaction at room temperature for 30 minutes, thereby obtaining a DNA probe for HER2 detection (probe reagent B).
<Verification of DNA Probe>
The thus obtained DNA probe was verified by an electrophoretic shift assay where the DNA probe in a 0.5% modified Tris-borate-EDTA (TBE) buffer was electrophoresed through a 0.5% TBE-containing 2% agarose gel. Single-stranded DNAs were counter-stained with SYBR Green II (Molecular Probes, Eugene, Oreg.). Then, the DNA migration pattern was determined as described below using "MultiImager FX System" (Bio-Rad, Hercules, Calif.).

That is, FITC existing in the electrophoresed gel was checked using a laser light having a wavelength of 488 nm as an excitation light along with a 530-nm bandpass emission filter.

As for the verification of the binding molar ratio of the BAC probe and biotin, the binding molar ratio was determined to be 1:20,000 by a HABA-avidin method using "Thermo Scientific Pierce Biotin Quantitation Kit" (manufactured by Thermo Fisher Scientific K.K.) where, with HABA being bound to streptavidin of FITC, HABA was substituted with biotin of the BAC probe.
[Other Observation, Etc.]
<FISH>
FISH was performed in the same manner as in Example 1.
<Bright-Field Observation>
For the above-prepared specimen slide, a first immunostained image was obtained using a light microscope ("Imager" manufactured by Carl Zeiss AG).
<Confocal Fluorescence Microscope Observation>
For the specimen slide prepared and subjected to FISH as described above, using a confocal microscope Zeiss LSM780 (manufactured by Carl Zeiss Microscopy GmbH), FITC of the hybridized DNA probe was excited at 488 nm and the fluorescence emitted from FITC was detected at a measurement wavelength of 530 nm to measure the fluorescence, obtain fluorescence images (static fluorescence images) and determine the number of bright spots. It is noted here that the images were each taken by changing the focal depth at 5.95 μm, 4.95 μm and 4.5 μm.
<Fluorescence Microscope Observation>
Fluorescence microscope observation was performed in the same manner as in Example 1.
<Results and Discussion>
Bright spots were confirmed in the fluorescence microscope observation.

Comparative Example 1

Preparation of BAC Probe Having Biotin Labeling Ratio of 1.33%

A solution of biotin-labeled 150,000-base BAC probe (nucleic acid molecule) having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.
<Preparation of DNA Probe in which Fluorescent Particles and BAC Probe Having Biotin Labeling Ratio of 1.33% are Bound>
The thus obtained biotin-labeled BAC probe in an amount of 25 μL (concentration: 1 μg/250 μL) and a solution containing 1.0 μL (50 nmol/50 μL) of Qdot (registered trademark, manufactured by Quantum Dot Corporation) having a streptavidin-labeled surface and an average particle size of 15 nm were mixed to perform binding reaction at room temperature for 30 minutes, thereby obtaining a DNA probe for HER2 detection (probe reagent C).
[Other Observation, Etc.]
Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:2,000 by a HABA-avidin method using "Thermo Scientific Pierce Biotin Quantitation Kit" (manufactured by Thermo Fisher Scientific K.K.) where, with HABA being bound to streptavidin of Q-dot, HABA was substituted with biotin of the BAC probe.
<Results and Discussion>
No bright spot was observed in the fluorescence microscope observation.

Comparative Example 2

Preparation of BAC Probe Having Biotin Labeling Ratio of 1.33%

A solution of biotin-labeled 150,000-base BAC probe (nucleic acid molecule) having a final concentration of 1 μg/250 μL was obtained in the same manner as in Example 1, except that the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.
<Preparation of DNA Probe in which Fluorescent Dyes and BAC Probe Having Biotin Labeling Ratio of 1.33% are Bound>
The thus obtained biotin-labeled BAC probe in an amount of 25 μL (concentration: 1 μg/250 μL) and a solution containing 1.0 μL (50 nmol/50 μL) of FITC-modified streptavidin ("Streptavidin, FITC Conjugate (1 mg, SA-5001)" manufactured by Funakoshi Co., Ltd.) were mixed to perform binding reaction at room temperature for 30 minutes, thereby obtaining a DNA probe for HER2 detection (probe reagent D).
[Other Observation, Etc.]
Verification of the DNA probe, storage of the DNA probe, FISH, bright-field observation, confocal fluorescence microscope observation, fluorescence microscope observation and the like were performed in the same manner as in Example 1.

As for verification of the binding molar ratio of the BAC probe and biotin in the DNA probe, the binding molar ratio was determined to be 1:2,000 by a HABA-avidin method using "Thermo Scientific Pierce Biotin Quantitation Kit" (manufactured by Thermo Fisher Scientific K.K.) where, with HABA being bound to streptavidin of FITC, HABA was substituted with biotin of the BAC probe.
<Results and Discussion>
No bright spot was observed in the fluorescence microscope observation.

Example 2

Preparation of BAC Probe Having Biotin Labeling Ratio of 1.33%

A solution of biotin-labeled 150,000-base BAC probe (nucleic acid molecule) having a final concentration of 1

µg/250 µL was obtained in the same manner as in Example 1, except that, in the biotin labeling by nick translation, the amount of dTTP was changed from 0.5 µL to 1.5 µL and the amount of Biotin-16-dUTP (product number: 1093070, manufactured by Roche, 50 nmol/50 µL) was changed from 1.5 µL to 0.2 µL.

<Preparation of Texas Red Dye-Containing Silica Nanoparticles>

An organoalkoxysilane compound was obtained by mixing 3.4 mg of Texas Red dye and 3 µL of 3-aminopropyltrimetoxysilane (KBM903, manufactured by Shin-Etsu Chemical Co., Ltd.) in DMF. Then, 0.6 mL of the thus obtained organoalkoxysilane compound was mixed with 48 mL of ethanol, 0.6 mL of TEOS (tetraethoxysilane), 2 mL of water and 1.4 mL of 28% aqueous ammonia for 3 hours. The thus prepared mixture was centrifuged at 10,000 G for 20 minutes and the resulting supernatant was removed. The precipitates were dispersed by adding thereto ethanol, and the resulting dispersion was centrifuged again. Washing with ethanol and washing with pure water were each performed twice by the same procedure. By these operations, Texas Red dye-silica nanoparticles were obtained. As a result of SEM observation of 1,000 of the thus obtained nanoparticles, their average particle size was found to be 50 nm.

The thus obtained phosphor-integrated nanoparticles were adjusted with PBS (phosphate-buffered physiological saline) containing 2 mM of EDTA (ethylenediamine tetraacetic acid) to a concentration of 3 nM, and the resulting solution was mixed with SM(PEG)$_{12}$ (manufactured by Thermo Fisher Scientific K.K.; succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, the precipitates were dispersed by adding thereto PBS containing 2 mM of EDTA, and the resulting dispersion was centrifuged again. The precipitates were washed three times by the same procedure to obtain phosphor-integrated nanoparticles having a maleimide group attached to a terminal.

Meanwhile, streptavidin (manufactured by Wako Pure Chemical Industries, Ltd.) was subjected to a thiol group addition treatment with N-succinimidyl-S-acetylthioacetate (SATA) and subsequently filtered through a gel-filtration column to obtain a solution of streptavidin capable of binding to the phosphor-integrated nanoparticles.

The above-described phosphor-integrated nanoparticles and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a gel-filtration column for purification, thereby obtaining Texas Red dye-containing phosphor-integrated nanoparticles bound with streptavidin.

<Preparation of DNA Probe in which Phosphor-Integrated Nanoparticles (50 nm, Silica Particles) and BAC Probe Having Biotin Labeling Ratio of 1.33% are Bound>

The above-prepared biotin-labeled BAC probe in an amount of 25 µL (concentration: 1 µg/250 µL) and a solution containing the above-prepared phosphor-integrated nanoparticles bound with streptavidin were mixed to perform binding reaction at room temperature for 30 minutes, thereby obtaining a DNA probe for HER2 detection (probe reagent E).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:2,000 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the BAC probe.

<Results and Discussion>

In the fluorescence microscope observation, bright spots at deep positions were visually observable without adjusting the focus in the depth direction.

Example 3

Preparation of BAC Probe Having Biotin Labeling Ratio of 1.33%

A solution of biotin-labeled 150,000-base BAC probe (nucleic acid molecule) having a final concentration of 1 µg/250 µL was obtained in the same manner as in Example 1, except that, in the biotin labeling by nick translation, the amount of dTTP was changed from 0.5 µL to 1.5 µL and the amount of Biotin-16-dUTP (product number: 1093070, manufactured by Roche, 50 nmol/50 µL) was changed from 1.5 µL to 0.2 µL.

<Preparation of Fluorescent Dye-Containing Polymelamine Particles Labeled with Streptavidin>

SulfoRhodamine 101 (manufactured by Sigma-Aldrich) in an amount of 20.3 mg was added to and dissolved in 22 mL of water. Then, to this solution, 2 mL of a 5% aqueous solution of an emulsifier for emulsion polymerization, EMULGEN (registered trademark) 430 (polyoxyethylene oleyl ether, manufactured by Kao Corporation), was added. The resulting solution was heated to 70° C. with stirring on a hot stirrer, and 0.81 g of a melamine resin material, NIKALAC MX-035 (manufactured by Nippon Carbide Industries Co., Inc.), was subsequently added thereto.

To this solution, as a surfactant, 1,000 µL of a 10% aqueous solution of dodecylbenzenesulfonic acid (manufactured by Kanto Chemical Co., Inc.) was further added, and the resultant was heated with stirring at 70° C. for 50 minutes. Thereafter, the resultant was further heated with stirring at 90° C. for 20 minutes. The resulting dispersion of phosphor-integrated nanoparticles was washed with pure water so as to remove impurities such as excess resin material and fluorescent dye.

Specifically, the dispersion was centrifuged at 20,000 G for 15 minutes using a centrifugal machine (Micro Refrigerated Centrifuge 3740, manufactured by Kubota Corporation) and, after removing the resulting supernatant, the precipitates were re-dispersed in ultrapure water by ultrasonication. The centrifugation, the removal of supernatant and the washing by re-dispersion in ultrapure water were repeated five times. In the thus obtained melamine particles, the melamine resin itself contained a large number of amino groups in its skeleton. As a result of SEM observation of 1,000 of the thus obtained nanoparticles, their average particle size was found to be 280 nm.

Then, 0.1 mg of the thus obtained phosphor-integrated nanoparticles was dispersed in 1.5 mL of ethanol, and 2 µL of aminopropyltrimethoxysilane (LS-3150, manufactured by Shin-Etsu Chemical Co., Ltd.) was added thereto. The resulting mixture was allowed to react for 8 hours so as to perform a surface amination treatment, thereby converting the hydroxyl groups existing on the surface of the resin particles to amino groups.

The resulting phosphor-integrated nanoparticles were adjusted with a phosphate-buffered physiological saline (PBS) containing 2 mM of ethylenediamine tetraacetic acid (EDTA) to a concentration of 3 nM. The resulting dispersion of the phosphor-integrated nanoparticles having the adjusted concentration was mixed with SM(PEG)$_{12}$ (succinimidyl-[(N-maleimidopropionamido)-dodecaethylene glycol]ester, manufactured by Thermo Fisher Scientific K.K.) to a final concentration of 10 mM, and the resultant was allowed to react at 20° C. for 1 hour, thereby obtaining a mixture containing fluorescent dye-containing phosphor-integrated nanoparticles having terminal maleimide.

This mixture was centrifuged at 10,000 G for 20 minutes and the resulting supernatant was removed. Then, the precipitates were dispersed by adding thereto PBS containing 2 mM of EDTA, and the resulting dispersion was centrifuged again. The precipitates were washed three times by the same procedure.

(Preparation of Streptavidin)

Meanwhile, streptavidin (manufactured by Wako Pure Chemical Industries, Ltd.) was subjected to a thiol group addition treatment with N-succinimidyl-S-acetylthioacetate (abbreviated as "SATA"), and the resultant was subjected to gel filtration to separately prepare streptavidin capable of binding to the phosphor-integrated nanoparticles.

(Binding of Resin Particles and Streptavidin)

The above-described phosphor-integrated nanoparticles and streptavidin were mixed in PBS containing 2 mM of EDTA and allowed to react at room temperature for 1 hour, thereby binding the phosphor-integrated nanoparticles with streptavidin. Then, the reaction was terminated with an addition of 10 mM mercaptoethanol. After concentrating the resulting solution using a centrifugation filter (φ=0.65 μm), unreacted streptavidin and the like were removed using a gel-filtration column for purification, thereby obtaining phosphor-integrated nanoparticles bound with streptavidin.

<Preparation of DNA Probe in which Phosphor-Integrated Nanoparticles (280 nm, Melamine Particles) and BAC Probe Having Biotin Labeling Ratio of 1.33% are Bound>

The thus obtained biotin-labeled BAC probe (nucleic acid molecule) in an amount of 25 μL (concentration: 1 μg/250 μL) and a solution containing the phosphor-integrated nanoparticles bound with streptavidin were mixed to perform binding reaction at room temperature for 30 minutes, thereby obtaining a DNA probe for HER2 detection (probe reagent F).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:2,000 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the BAC probe.

<Results and Discussion>

In the fluorescence microscope observation, bright spots at deep positions were visually observable without adjusting the focus in the depth direction.

Example 4

Preparation of BAC Probe Having Biotin Labeling Ratio of 1.33%

A solution of biotin-labeled 150,000-base BAC probe (nucleic acid molecule) having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.

<Preparation of Texas Red Dye-Containing Silica Nanoparticles>

Texas Red dye-silica nanoparticles were obtained in the same manner as in Example 2, except that the amount of 28% aqueous ammonia was changed from 1.4 mL to 2.6 mL. As a result of SEM observation of 1,000 of the thus obtained nanoparticles, their average particle size was found to be 320 nm.

While preparing fluorescent dye-containing particles having a maleimide group from the thus obtained dye-containing nanoparticles in the same manner as in Example 2, a streptavidin solution was also prepared in the same manner as in Example 2. From these, Texas Red dye-containing silica nanoparticles (phosphor-integrated nanoparticles) bound with streptavidin were obtained in the same manner as in Example 2.

<Preparation of DNA Probe in which Phosphor-Integrated Nanoparticles (320 nm, Silica Particles) and BAC Probe Having Biotin Labeling Ratio of 1.33% are Bound>

The above-prepared biotin-labeled BAC probe (nucleic acid molecule) in an amount of 25 μL (concentration: 1 μg/250 μL) and a solution containing the above-prepared phosphor-integrated nanoparticles bound with streptavidin were mixed to perform binding reaction at room temperature for 30 minutes, thereby obtaining a DNA probe for HER2 detection (probe reagent G).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:2,000 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the BAC probe.

<Results and Discussion>

In the fluorescence microscope observation, bright spots at deep positions were visually observable without adjusting the focus in the depth direction.

Reference Example 2

Preparation of BAC Probe Having Biotin Labeling Ratio of 9.62%

For 1 μg (5 μL) of a HER2-DNA clone (CEN17q 11.2/520 kb, number of bases: about 520 kbp) purchased as a BAC probe from GSP Lab., Inc., dTTP of the BAC probe (nucleic acid molecule) was labeled with biotin in the same manner as in Example 1 by a nick translation method in accordance with the protocol provided with a nick translation kit (product name: "GSP-nick translation kit" K-015; manufactured by GSP Lab., Inc.).
<Preparation of DNA Probe in which Fluorescent Dyes and BAC Probe Having Biotin Labeling Ratio of 9.62% are Bound>

The thus obtained biotin-labeled BAC probe in an amount of 25 μL (concentration: 1 μg/250 μL) and a solution containing 1.0 μL (50 nmol/50 μL) of FITC-modified streptavidin (Streptavidin, FITC Conjugate (1 mg, SA-5001, manufactured by Funakoshi Co., Ltd.)) were mixed to perform binding reaction at room temperature for 30 minutes, thereby obtaining a DNA probe for HER2 detection (probe reagent H).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:50,000 by a HABA-avidin method using "Thermo Scientific Pierce Biotin Quantitation Kit" (manufactured by Thermo Fisher Scientific K. K.) where, with HABA being bound to streptavidin of FITC, HABA was substituted with biotin of the BAC probe.

<Results and Discussion>

In the fluorescence microscope observation, bright spots at deep positions were observed by adjusting the focus in the depth direction.

Reference Example 3

Preparation of BAC Probe Having Biotin Labeling Ratio of 0.96%

For 1 μg (5 μL) of a HER2-DNA clone (CEN17q 11.2/520 kb, number of bases: about 520 kbp) purchased as a BAC probe from GSP Lab., Inc., dTTP of the BAC probe (nucleic acid molecule) was labeled with biotin as described below by a nick translation method in accordance with the protocol provided with a nick translation kit (product name: "GSP-nick translation kit" K-015; manufactured by GSP Lab., Inc.).

A solution of biotin-labeled BAC probe having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.

<Preparation of DNA Probe in which Fluorescent Dye and BAC Probe Having Biotin Labeling Ratio of 0.96% are Bound>

The thus obtained biotin-labeled BAC probe in an amount of 25 μL (concentration: 1 μg/250 μL) and a solution containing 1.0 μL (50 nmol/50 μL) of FITC-modified streptavidin (Streptavidin, FITC Conjugate (1 mg, SA-5001, manufactured by Funakoshi Co., Ltd.)) were mixed to perform binding reaction at room temperature for 30 minutes, thereby obtaining a DNA probe for HER2 detection (probe reagent I).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:5,000 by a HABA-avidin method using "Thermo Scientific Pierce Biotin Quantitation Kit" (manufactured by Thermo Fisher Scientific K. K.) where, with HABA being bound to streptavidin of FITC, HABA was substituted with biotin of the BAC probe.

<Results and Discussion>

No bright spot was observable in the fluorescence microscope observation.

Example 5

Preparation of BAC Probe Having Biotin Labeling Ratio of 0.96%

For 1 μg (5 μL) of a HER2-DNA clone (CEN17q 11.2/520 kb, number of bases: about 520 kbp) purchased as a BAC probe from GSP Lab., Inc., dTTP of the BAC probe (nucleic acid molecule) was labeled with biotin as described below by a nick translation method in accordance with the protocol provided with a nick translation kit (product name: "GSP-nick translation kit" K-015; manufactured by GSP Lab., Inc.).

A solution of biotin-labeled BAC probe having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.

<Preparation of Fluorescent Dye-Containing Polymelamine Particles>

Fluorescent dye-containing polymelamine particles were prepared in the same manner as in Example 3, except that the amount of SulfoRhodamine 101 (manufactured by Sigma-Aldrich) was changed from 14.4 mg to 5.25 mg and the amount of the melamine resin material NIKALAC MX-035 (manufactured by Nippon Carbide Industries Co., Inc.) was changed from 0.65 g to 0.21 g. As a result of SEM observation of 1,000 of the thus obtained particles, their average particle size was found to be 40 nm.

Using 0.1 mg of the thus obtained phosphor-integrated nanoparticles, a mixture containing fluorescent dye-containing phosphor-integrated nanoparticles having terminal maleimide was obtained in the same manner as in Example 3. Further, washing and the like were also performed in the same manner as in Example 3.

<Preparation of Streptavidin/Binding of Resin Particles and Streptavidin>

A DNA probe for HER2 detection (probe reagent J) was obtained by performing preparation of streptavidin and binding of resin particles and streptavidin in the same manner as in Example 3.

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:5,000 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the BAC probe.

<Results and Discussion>

In the fluorescence microscope observation, bright spots at deep positions were visually observable without adjusting the focus in the depth direction.

<<Overall Results and Discussion>>

It is noted here that the term "label" used in Tables 1 to 5 means a phosphor molecule capable of binding to a nucleic acid molecule (for example, when the nucleic acid molecule is labeled with biotin, the "label" means a phosphor-integrated nanoparticle having streptavidin).

TABLE 1

| | DNA clone | | Probe reagent | Substrate used in nick translation (μL) | | | DNA clone:label (molar ratio) | Labeling ratio (%) | Phosphor | | Phosphor Particle size (nm) | Confocal microscope | Fluorescence microscope |
|---|---|---|---|---|---|---|---|---|---|---|---|---|---|
| | Number of bases | | | Biotin-d-UTP | dTTP | dNTP | | | | Base material | | | |
| Example 1 | 150,000 | HER2 | A | 1.5 | 0.5 | 5 | 1:20,000 | 13.33 | Q-dot | — | 15 | Bright spots were observed. | Bright spots were observed. |
| Reference Example 1 | 150,000 | HER2 | B | 1.5 | 0.5 | 5 | 1:20,000 | 13.33 | FITC | — | <1 | Bright spots were observed. | Bright spots were observed. |
| Comparative Example 1 | 150,000 | HER2 | C | 0.2 | 1.5 | 5 | 1:2,000 | 1.33 | Q-dot | — | 15 | Bright spots were observed. | No bright spot was observable. |
| Comparative Example 2 | 150,000 | HER2 | D | 0.2 | 1.5 | 5 | 1:2,000 | 1.33 | FITC | — | <1 | Bright spots were observed. | No bright spot was observable. |
| Example 2 | 150,000 | HER2 | E | 0.2 | 1.5 | 5 | 1:2,000 | 1.33 | PID | silica | 50 | Bright spots were observed. | Bright spots were observed. |
| Example 3 | 150,000 | HER2 | F | 0.2 | 1.5 | 5 | 1:2,000 | 1.33 | PID | melamine resin | 280 | Bright spots were observed. | Bright spots were observed. |
| Example 4 | 150,000 | HER2 | G | 0.2 | 1.5 | 5 | 1:2000 | 1.33 | PID | silica | 320 | Bright spots were observed. | Bright spots were observed. |
| Reference Example 2 | 520,000 | CEN17 | H | 1.5 | 0.5 | 5 | 1:50,000 | 9.62 | FITC | — | <1 | Bright spots were observed. | Bright spots were observed. |
| Reference Example 3 | 520,000 | CEN17 | I | 0.2 | 1.5 | 5 | 1:5,000 | 0.96 | FITC | — | <1 | Bright spots were observed. | No bright spot was observable. |
| Example 5 | 520,000 | CEN17 | J | 0.2 | 1.5 | 5 | 1:5,000 | 0.96 | PID | melamine resin | 40 | Bright spots were observed. | Bright spots were observed. |

*PID = phosphor-integrated nanoparticles

As shown in Table 1, in known examples, Example 1 and Reference Example 1, bright spots were observed even under a light microscope because of the use of a probe reagent having a high biotin labeling ratio (13.33%); however, in Comparative Examples 1 and 2 where a probe reagent having a low biotin labeling ratio (1.33%) was used, although bright spots were observed under a confocal microscope, no bright spot was observable under a light microscope.

In contrast, with the probe reagents of Examples 2 and 3, bright spots were observed under not only a confocal microscope but also a light microscope, despite that these probe reagents had a low biotin labeling ratio (1.33%). The reason why bright spots were observed in Examples 2 and 3 is believed to be because the phosphor-integrated nanoparticles each had a high brightness.

Comparative Example 3

Preparation of BAC Probe Having Biotin Labeling Ratio of 1.33%

A solution of biotin-labeled 150,000-base BAC probe (nucleic acid molecule) having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.

<Preparation of DNA Probe in which Fluorescent Particles and BAC Probe Having Biotin Labeling Ratio of 1.33% are Bound>

The thus obtained biotin-labeled BAC probe in an amount of 25 μL (concentration: 1 μg/250 μL) and a solution containing 1.0 μL (50 nmol/50 μL) of Q-dot (registered trademark, manufactured by Quantum Dot Corporation)

having a streptavidin-modified surface and an average particle size of 15 nm were mixed to perform binding reaction at room temperature for 30 minutes, thereby obtaining a DNA probe for HER2 detection (probe reagent K).
[Other Observation, Etc.]
Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:2,000 by a HABA-avidin method using "Thermo Scientific Pierce Biotin Quantitation Kit" (manufactured by Thermo Fisher Scientific K. K.) where, with HABA being bound to streptavidin of Q-dot, HABA was substituted with biotin of the BAC probe.
<Results and Discussion>
No bright spot was observed in the fluorescence microscope observation.

Comparative Example 4

Preparation of DNA Probe Having Biotin Labeling Ratio of 13.33%

Using Applied Biosystems 392 DNA/RNA Synthesizer (Foster City, Calif.), primers (forward: 5'-CGGGAGATC-CCTGACCTGCTGGAA-3' (SEQ ID NO: 1), reverse: 5'-CTGCTGGGGTACCAGATACTCCTC-3' (SEQ ID NO: 2)) were prepared.

Next, a 300-base cDNA (nucleic acid molecule) having a HER2 gene-related sequence was prepared by performing a reverse transcription reaction using total RNA extracted from TRG cells as a template along with a set of the above primers, "SuperScript (registered trademark) II Reverse Transcriptase" manufactured by Invitrogen Corp. and a common commercially available PCR reagent in accordance with the protocol described in the product manual of this reverse transcriptase. It is noted here that the total RNA was extracted from TRG cells using TRIzol Reagent (Invitrogen Corp., Carlsbad, Calif.) as described in the method IV of "Journal of Yokohama Medical Association, 56, 111-119 (2005)".

Using 1 μg of the thus obtained cDNA, nick translation was performed in the same manner as in Example 1, thereby obtaining a solution of a biotin-labeled cDNA having a final concentration of 1 μg/250 μL.
<Preparation of DNA Probe in which Fluorescent Particles and cDNA Having Biotin Labeling Ratio of 13.33% are Bound>

The thus obtained biotin-labeled cDNA in an amount of 25 μL (concentration: 1 μg/250 μL) and a solution containing 1.0 μL (50 nmol/50 μL) of Q-dot (registered trademark, manufactured by Quantum Dot Corporation) having a streptavidin-modified surface and an average particle size of 15 nm were mixed to perform binding reaction at room temperature for 30 minutes, thereby obtaining a 300-bp DNA probe for HER2 detection (probe reagent L).
<Verification of DNA Probe>

The thus obtained DNA probe was verified in the same manner as in Example 1, except that a 0.5% TBE-containing 10% polyacrylamide gel was used in place of the 0.5% TBE-containing 2% agarose gel.
[Other Observation, Etc.]

FISH, bright-field observation, confocal fluorescence microscope observation, fluorescence microscope observation and the like were performed in the same manner as in Example 1. Here, in each of the confocal fluorescence microscope observation and the fluorescence microscope observation, the number of bright spots was measured for a stained image of cultured MCF7 cells. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K.K.) where, with HABA being bound to streptavidin of Q-dot, HABA was substituted with biotin of the cDNA.

Further, in this case, bright spots were measured for those cells that were included in the image itself (1,600 pixels× 1,200 pixels) taken under a confocal microscope Zeiss LSM780 (manufactured by Carl Zeiss Microscopy GmbH) using a ×60 objective lens (oil immersion). Since the cultured MCF7 cells are known as cells with low HER2 expression and are substantially the same as normal cells, it is normal to find two bright spots per nucleus.
<Results and Discussion>

As a result of measuring bright spots in the confocal fluorescence microscope observation, it was found that there were 20 cells showing one bright spot, 29 cells showing two bright spots and 1 cell showing three bright spots, with no cell showing four bright spots. Further, no bright spot was observable in the fluorescence microscope observation.

Example 6

Preparation of DNA Probe Having Biotin Labeling Ratio of 13.33%

Using Applied Biosystems 392 DNA/RNA Synthesizer (Foster City, Calif.), primers (forward: 5'-CGGGAGATC-CCTGACCTGCTGGAA-3' (SEQ ID NO: 3) and reverse: 5'-CTGCTGGGGTACCAGATACTCCTC-3' (SEQ ID NO: 4)) were prepared.

Next, a 300-base cDNA (nucleic acid molecule) having a HER2 gene-related sequence was prepared by performing a reverse transcription reaction using total RNA extracted from TRG cells as a template along with a set of the above primers, "SuperScript (registered trademark) II Reverse Transcriptase" manufactured by Invitrogen Corp. and a common commercially available PCR reagent in accordance with the protocol described in the product manual of this reverse transcriptase. It is noted here that extraction of the total RNA was performed in the same manner as in Comparative Example 4.

Using 1 μg of the thus obtained cDNA, nick translation was performed in the same manner as in Example 1, thereby obtaining a solution of a biotin-labeled cDNA having a final concentration of 1 μg/250 μL.
<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 5.25 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 40 nm. Further, a mixture containing fluorescent dye-containing phosphor-integrated nanoparticles having terminal maleimide was obtained in the same manner as in Example 3. Washing and the like were also performed in the same manner as in Example 3.

<Preparation of Streptavidin/Binding of Particles and Streptavidin>

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.

<Preparation of DNA Probe in which Phosphor-Integrated Nanoparticles (40 nm, Melamine Particles) and cDNA Having Biotin Labeling Ratio of 13.33% are Bound>

The biotin-labeled cDNA obtained above in an amount of 25 μL (concentration: 1 μg/250 μL) and a solution containing the phosphor-integrated nanoparticles modified with streptavidin were mixed to perform binding reaction at room temperature for 30 minutes, thereby obtaining a DNA probe for HER2 detection (probe reagent M).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 21 cells showing one bright spot and 29 cells showing two bright spots, with no cell showing three or four bright spots. Further, as a result of measuring bright spots in the fluorescence microscope observation, it was found that there were 21 cells showing one bright spot and 29 cells showing two bright spots, with no cell showing three or four bright spots.

In other words, even in fluorescence microscope observation where the detection sensitivity of bright spots is low, the probe reagent of Example 6 enables to detect bright spots with almost the same accuracy as that in confocal fluorescence microscope observation where the detection sensitivity of bright spots is high.

Example 7

Preparation of DNA Probe Having Biotin Labeling Ratio of 13.33%

A 300-base cDNA (nucleic acid molecule) having a HER2 gene-related sequence was prepared in the same manner as in Example 6. Using 1 μg of the thus obtained cDNA, nick translation was performed in the same manner as in Example 1, thereby obtaining a solution of a biotin-labeled cDNA having a final concentration of 1 μg/250 μL.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.

<Preparation of Streptavidin/Binding of Particles and Streptavidin>

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.

<Preparation of DNA Probe in which Phosphor-Integrated Nanoparticles (158 nm, Melamine Particles) and cDNA Having Biotin Labeling Ratio of 13.33% are Bound>

The biotin-labeled cDNA obtained above in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent N).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 19 cells showing one bright spot, 29 cells showing two bright spots and 2 cells showing three bright spots, with no cell showing four bright spots. Further, as a result of measuring bright spots in the fluorescence microscope observation, it was found that there were 21 cells showing one bright spot, 29 cells showing two bright spots and 1 cell showing three bright spots, with no cell showing four bright spots.

In other words, even in fluorescence microscope observation where the detection sensitivity of bright spots is low, the probe reagent of Example 7, although having a slightly larger average particle size of 158 nm than the probe reagent of Example 2, enables to detect bright spots with almost the same accuracy as that in confocal fluorescence microscope observation where the detection sensitivity of bright spots is high.

Example 8

Preparation of DNA Probe Having Biotin Labeling Ratio of 13.33%

A 300-base cDNA (nucleic acid molecule) having a HER2 gene-related sequence was prepared in the same manner as in Example 6. Using 1 μg of the thus obtained cDNA, nick translation was performed in the same manner as in Example 1, thereby obtaining a solution of a biotin-labeled cDNA having a final concentration of 1 µg/250 µL.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed to 20.3 mg and the amount of the melamine resin material NIKALAC MX-035 (manufactured by Nippon Carbide Industries Co., Inc.) was changed to 0.81 g. As a result of SEM observation of 1,000 of the thus obtained nanoparticles, their average particle size was found to be 280 nm.

Further, a mixture containing fluorescent dye-containing phosphor-integrated nanoparticles having terminal maleimide was obtained in the same manner as in Example 3. Washing and the like were also performed in the same manner as in Example 3.

<Preparation of Streptavidin/Binding of Particles and Streptavidin>

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.

<Preparation of DNA Probe in which Phosphor-Integrated Nanoparticles (280 nm, Melamine Particles) and cDNA Having Biotin Labeling Ratio of 13.3% are Bound>

The biotin-labeled cDNA obtained above in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent O).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3.

As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 21 cells showing one bright spot and 29 cells showing two bright spots, with no cell showing three or four bright spots. Further, as a result of measuring bright spots in the fluorescence microscope observation, it was found that there were 21 cells showing one bright spot and 29 cells showing two bright spots, with no cell showing three or four bright spots.

In other words, even in fluorescence microscope observation where the detection sensitivity of bright spots is low, the probe reagent of Example 8, although having a larger average particle size of 280 nm than the probe reagents of Examples 6 and 7, enables to detect bright spots with almost the same accuracy as that in confocal fluorescence microscope observation where the detection sensitivity of bright spots is high.

Example 9

Preparation of Probe Having Biotin Labeling Ratio of 13.33%

A 300-base cDNA (nucleic acid molecule) having a HER2 gene-related sequence was prepared in the same manner as in Example 6. Using 1 µg of the thus obtained cDNA, nick translation was performed in the same manner as in Example 1, thereby obtaining a solution of a biotin-labeled cDNA having a final concentration of 1 µg/250 µL.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 21.4 mg and the amount of the melamine resin material NIKALAC MX-035 (manufactured by Nippon Carbide Industries Co., Inc.) was changed from 0.81 g to 0.86 g. As a result of SEM observation of 1,000 of the thus obtained nanoparticles, their average particle size was found to be 320 nm.

Further, a mixture containing fluorescent dye-containing phosphor-integrated nanoparticles having terminal maleimide was obtained in the same manner as in Example 3. Washing and the like were also performed in the same manner as in Example 3.

<Preparation of Streptavidin/Binding of Particles and Streptavidin>

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.

<Preparation of DNA Probe in which Phosphor-Integrated Nanoparticles (320 nm, Melamine Particles) and cDNA Having Biotin Labeling Ratio of 13.33% are Bound>

The biotin-labeled cDNA obtained above in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent P).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 43 cells showing one bright spot and 7 cells showing two bright spots, with no cell showing three or four bright spots. Further, as a result of measuring bright spots in the fluorescence microscope observation, it was found that there were 44 cells showing one bright spot and 6 cells showing two bright spots, with no cell showing three or four bright spots.

In other words, even in fluorescence microscope observation where the detection sensitivity of bright spots is low, the probe reagent of Example 9, although having a larger average particle size of 320 nm than the probe reagents of Examples 6 and 7, enables to detect bright spots with almost the same accuracy as that in confocal fluorescence microscope observation where the detection sensitivity of bright spots is high.

Example 10

Preparation of Probe Having Biotin Labeling Ratio of 1.67%

A 300-base cDNA (nucleic acid molecule) having a HER2 gene-related sequence was prepared in the same manner as in Example 6.

Using 1 µg of the thus obtained cDNA, a biotin-labeled cDNA having a final concentration of 1 µg/250 µL was obtained by performing nick translation in the same manner as in Example 1, except that the amount of dTTP was changed from 0.5 µL to 1.5 µL and the amount of Biotin-16-dUTP (product number: 1093070, manufactured by Roche, 50 nmol/50 µL) was changed from 1.5 µL to 0.2 µL.
<Preparation of Texas Red Dye-Containing Silica Nanoparticles Labeled with Streptavidin>

Texas Red dye-containing silica nanoparticles were prepared in the same manner as in Example 2, except that the amount of 28% aqueous ammonia was changed from 1.4 mL to 2.0 mL. As a result of SEM observation of 1,000 of the thus obtained particles, their average particle size was found to be 160 nm.

While preparing fluorescent dye-containing particles having a maleimide group from the thus obtained dye-containing nanoparticles in the same manner as in Example 2, a streptavidin solution was also prepared in the same manner as in Example 2. From these, Texas Red dye-containing silica nanoparticles (phosphor-integrated nanoparticles) bound with streptavidin were obtained in the same manner as in Example 2.
<Preparation of DNA Probe in which Phosphor-Integrated Nanoparticles (160 nm, Silica Particles) and cDNA Having Biotin Labeling Ratio of 1.67% are Bound>

The biotin-labeled cDNA obtained above in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent Q).
[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:5 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 19 cells showing one bright spot, 29 cells showing two bright spots and 2 cells showing three bright spots, with no cell showing four bright spots. Further, as a result of measuring bright spots in the fluorescence microscope observation, it was found that there were 20 cells showing one bright spot, 29 cells showing two bright spots and 1 cell showing three bright spots, with no cell showing four bright spots.

In other words, even in fluorescence microscope observation where the detection sensitivity of bright spots was low, the probe reagent of Example 10, although having a very small binding molar ratio of cDNA:biotin (cDNA:phosphor-integrated nanoparticle) at 1:5, enabled to detect bright spots with almost the same accuracy as that in confocal fluorescence microscope observation where the detection sensitivity of bright spots was high.

Example 11

Preparation of Probe Having Biotin Labeling Ratio of 1.67%

A 300-base cDNA (nucleic acid molecule) having a HER2 gene-related sequence was prepared in the same manner as in Example 6.

Using 1 µg of the thus obtained cDNA, a biotin-labeled cDNA having a final concentration of 1 µg/250 µL was obtained by performing nick translation in the same manner as in Example 1, except that the amount of dTTP was changed from 0.5 µL to 1.5 µL and the amount of Biotin-16-dUTP (product number: 1093070, manufactured by Roche, 50 nmol/50 µL) was changed from 1.5 µL to 0.2 µL.
<Preparation of Texas Red Dye-Containing Silica Nanoparticles Labeled with Streptavidin>

Texas Red dye-containing silica nanoparticles were prepared in the same manner as in Example 2, except that the amount of 28% aqueous ammonia was changed from 1.4 mL to 2.6 mL. As a result of SEM observation of 1,000 of the thus obtained particles, their average particle size was found to be 320 nm.

While preparing fluorescent dye-containing particles having a maleimide group from the thus obtained dye-containing nanoparticles in the same manner as in Example 2, a streptavidin solution was also prepared in the same manner as in Example 2. From these, Texas Red dye-containing silica nanoparticles (phosphor-integrated nanoparticles) bound with streptavidin were obtained in the same manner as in Example 2.
<Preparation of DNA Probe in which Phosphor-Integrated Nanoparticles (320 nm, Silica Particles) and cDNA Having Biotin Labeling Ratio of 1.67% are Bound>

The biotin-labeled cDNA obtained above in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent R).
[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:5 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Results and Discussion>

As a result of measuring bright spots in the confocal fluorescence microscope observation, it was found that there were 40 cells showing one bright spot and 10 cells showing two bright spots, with no cell showing three or four bright spots. Further, as a result of measuring bright spots in the fluorescence microscope observation, it was found that there were 44 cells showing one bright spot and 6 cells showing two bright spots, with no cell showing three or four bright spots.

In other words, even in fluorescence microscope observation where the detection sensitivity of bright spots is low, the probe reagent of Example 11 enables to detect bright spots with almost the same accuracy as that in confocal fluorescence microscope observation where the detection sensitivity of bright spots is high.

Example 12

Preparation of BAC Probe Having Biotin Labeling Ratio of 0.33%

A BAC probe was prepared by performing a nick translation reaction using a BAC probe having a HER2 gene-related sequence in the same manner as in Comparative Example 3. However, the preparation of the BAC probe was performed without adding Biotin-d-UTP, which is different from Comparative Example 3. The thus obtained BAC clone-derived DNA (nucleic acid molecule) was labeled with biotin as described below.

<Biotin Labeling of 5'-End>

Using a kit "5' EndTag™ Nucleic Acid Labeling System (catalog No. MB-9001)" manufactured by Vector Laboratories, Inc. in accordance with its protocol, 2 µg of the thus prepared BAC clone-derived DNA was labeled with biotin at the 5'-end as described below.

The following materials were mixed in a centrifuge tube and incubated at 37° C. for 30 minutes.
  the above-described DNA: 2 µg (/8 µL of ultrapure water)
  Universal reaction buffer: 1 µL
  alkaline phosphatase: 1 µL In addition, the resulting mixture was further mixed with the following materials and incubated at 37° C. for 30 minutes.
  Universal reaction buffer: 2 µL
  ATPγS: 1 µL
  T4 polynucleotide kinase: 2 µL Next, 312 µL of DMSO in which "Biotin Maleimide" (catalog No. SP-1501, manufactured by Vector Laboratories, Inc.) was dissolved was added to the thus incubated reaction solution, followed by mixing. The resulting mixture was incubated at 65° C. for 30 minutes (or room temperature for 2 hours).

Then, 70 µL of nuclease-free water and 100 µL of equilibrated phenol were added to the thus incubated mixture, and the resultant was vortex-mixed for several seconds. The resulting supernatant aqueous layer was transferred to a new centrifuge tube. To 5 µL of 3M sodium acetate of this aqueous layer, 270 µL of 95% ethanol was added, and the resultant was mixed. This mixture was centrifuged at 13,000×g for 30 minutes, and the resulting precipitates were rinsed with 70% ethanol and further centrifuged at 13,000×g for 3 minutes. The precipitates were dried and dissolved in a TE buffer (10 mM Tris, 1 mM EDTA, pH 8) to obtain a DNA labeled with biotin at the 5'-end.

<Preparation of Texas Red Dye-Containing Silica Nanoparticles Labeled with Streptavidin>

Texas Red dye-containing silica nanoparticles were prepared in the same manner as in Example 2, except that the amount of 28% aqueous ammonia was changed from 1.4 mL to 2.0 mL. As a result of SEM observation of 1,000 of the thus obtained particles, their average particle size was found to be 160 nm.

While preparing fluorescent dye-containing particles having a maleimide group from the thus obtained dye-containing nanoparticles in the same manner as in Example 2, a streptavidin solution was also prepared in the same manner as in Example 2. From these, Texas Red dye-containing silica nanoparticles (phosphor-integrated nanoparticles) bound with streptavidin were obtained in the same manner as in Example 2.

<Preparation of DNA Probe in which Phosphor-Integrated Nanoparticles (160 nm, Silica Particles) are Bound to 5'-End of DNA>

The above-prepared BAC clone-derived DNA labeled with biotin at the 5'-end in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent S).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the DNA and biotin, the binding molar ratio was determined to be 1:50 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.

<Results and Discussion>

As a result of measuring bright spots in the confocal fluorescence microscope observation, it was found that there were 19 cells showing one bright spot, 29 cells showing two bright spots and 2 cells showing three bright spots, with no cell showing four bright spots. Further, as a result of measuring bright spots in the fluorescence microscope observation, it was found that there were 25 cells showing one bright spot, 24 cells showing two bright spots and 1 cell showing three bright spots, with no cell showing four bright spots.

In other words, even in fluorescence microscope observation where the detection sensitivity of bright spots was low, the probe reagent of Example 12, although having a binding molar ratio of 1:50 between the BAC clone-derived DNA and biotin (DNA:phosphor-integrated nanoparticle), enabled to detect bright spots with almost the same accuracy as that in confocal fluorescence microscope observation where the detection sensitivity of bright spots was high.

Comparative Example 5

Preparation of BAC Probe Having Biotin Labeling Ratio of 6.67E-3%

The same HER2-DNA clone (about 150 kbp) as used in Example 1 which was purchased from GSP Lab., Inc. was labeled with biotin at the 5'-end in the same manner as in Example 12.

<Preparation of DNA Probe in which Fluorescent Particles and BAC Probe are Bound>

The thus obtained BAC probe labeled with biotin at the 5'-end in an amount of 25 µL (concentration: 1 µg/250 µL) and a solution containing 1.0 µL (50 nmol/50 µL) of Q-dot (registered trademark, manufactured by Quantum Dot Corporation) having a streptavidin-modified surface and an average particle size of 15 nm were mixed to perform binding reaction at room temperature for 30 minutes, thereby obtaining a DNA probe for HER2 detection (probe reagent Ad1).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:1 by a HABA-avidin method using "Thermo Scientific Pierce Biotin Quantitation Kit" (manufactured by Thermo Fisher Scientific K.K.) where, with HABA being bound to streptavidin of Q-dot, HABA was substituted with biotin of the BAC probe.

<Results and Discussion>

As a result of measuring bright spots in the confocal fluorescence microscope observation, it was found that there were 12 cells showing one bright spot, 13 cells showing two bright spots, 15 cells showing three bright spots and 10 cells showing four bright spots. Meanwhile, no bright spot was observed in the fluorescence microscope observation.

Comparative Example 6

Preparation of Probe Having Biotin Labeling Ratio of 0.33%

A 300-base cDNA (nucleic acid molecule) having a HER2 gene-related sequence was prepared in the same manner as in Comparative Example 4, and the 5'-end of the cDNA was subsequently labeled with biotin in the same manner as in Example 12.

<Preparation of DNA Probe in which Fluorescent Particles and BAC Probe are Bound>

The thus obtained cDNA probe labeled with biotin at the 5'-end in an amount of 25 µL (concentration: 1 µg/250 µL) and a solution containing 1.0 µL (50 nmol/50 µL) of Q-dot (registered trademark, manufactured by Quantum Dot Corporation) having a streptavidin-modified surface and an average particle size of 15 nm were mixed to perform binding reaction at room temperature for 30 minutes, thereby obtaining a DNA probe for HER2 detection (probe reagent Ad2).

[Other Observation, Etc.]

Verification of the DNA probe, storage of the DNA probe, FISH, bright-field observation, confocal fluorescence microscope observation, fluorescence microscope observation and the like were performed in the same manner as in Example 1. As for the verification of the binding molar ratio of the BAC probe and biotin, the binding molar ratio was determined to be 1:1 by a HABA-avidin method using "Thermo Scientific Pierce Biotin Quantitation Kit" (manufactured by Thermo Fisher Scientific K.K.) where, with HABA being bound to streptavidin of Q-dot, HABA was substituted with biotin of the BAC probe.

<Results and Discussion>

As a result of measuring bright spots in the confocal fluorescence microscope observation, it was found that there were 21 cells showing one bright spot, 27 cells showing two bright spots and 2 cells showing three bright spots, with no cell showing four bright spots. Meanwhile, no bright spot was observed in the fluorescence microscope observation.

Example 13

Preparation of BAC Probe Having Biotin Labeling Ratio of 6.67E-3%

The same HER2-DNA clone (about 150 kbp) as used in Example 1 which was purchased from GSP Lab., Inc. was labeled with biotin at the 5'-end in the same manner as in Example 12.

<Preparation of Fluorescent Dye-Containing Polymelamine Particles Labeled with Streptavidin>

Fluorescent dye-containing polymelamine particles (phosphor-integrated nanoparticles) labeled with streptavidin were prepared in the same manner as in Example 3, except that the amount of SulfoRhodamine 101 (manufactured by Sigma-Aldrich) was changed to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.

<Direct Binding of Phosphor-Integrated Nanoparticles and HER2-DNA Clone (5'-End Labeling)>

For 2 µg of the above-prepared DNA, using a kit "5' EndTag™ Nucleic Acid Labeling System (catalog No. MB-9001)" manufactured by Vector Laboratories, Inc. in accordance with its protocol, the 5'-end of the nucleic acid molecule was converted from phosphoric acid to thiophosphoric acid as described below.

The following materials were mixed in a centrifuge tube and incubated at 37° C. for 30 minutes.
 the above-described nucleic acid molecule: 2 µg (/8 µL of ultrapure water)
 Universal reaction buffer: 1 µL
 alkaline phosphatase: 1 µL In addition, the resulting mixture was further mixed with the following materials and incubated at 37° C. for 30 minutes.
 Universal reaction buffer: 2 µL
 ATPγS: 1 µL
 T4 polynucleotide kinase: 2 µL Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-labeled DNA (probe reagent Ad3) (final concentration: 1 μg/250 μL).
[Other Observation, Etc.]
Verification of the DNA probe, storage of the DNA probe, FISH, bright-field observation, confocal fluorescence microscope observation, fluorescence microscope observation and the like were performed in the same manner.

In the verification of the DNA probe, since only the 5'-end was labeled, the binding molar ratio was found to be 1:1. Further, as a specimen slide, a slide of HER2-positive staining control specimen ("HER2-FISH Control Slide" manufactured by Pathology Institute Corp., code: PS-09006) was used. This specimen slide was subjected to confocal fluorescence microscope observation, fluorescence microscope observation and the like.
<Results and Discussion>
As a result of measuring bright spots in the confocal fluorescence microscope observation, it was found that there were 21 cells showing one bright spot, 26 cells showing two bright spots, 9 cells showing three bright spots and 4 cells showing four bright spots. The bright spots were also observable in the fluorescence microscope observation.

Example 14

Preparation of Probe Having Biotin Labeling Ratio of 0.33%

A solution of a phosphor-integrated nanoparticle-labeled DNA (probe reagent Ad4) (final concentration: 1 μg/250 μL) was obtained in the same manner as in Example 13, except that the biotin-labeled 300-base nucleic acid molecule prepared in Comparative Example 6 was used.
[Other Observation, Etc.]
Verification of the DNA probe, storage of the DNA probe, FISH, bright-field observation, confocal fluorescence microscope observation, fluorescence microscope observation and the like were performed in the same manner.

In the verification of the DNA probe, since only the 5'-end was labeled, the binding molar ratio was found to be 1:1. Further, as a specimen slide, a slide of HER2-positive staining control specimen ("HER2-FISH Control Slide" manufactured by Pathology Institute Corp., code: PS-09006) was used. This specimen slide was subjected to confocal fluorescence microscope observation, fluorescence microscope observation and the like.
<Results and Discussion>
As a result of measuring bright spots in the confocal fluorescence microscope observation, it was found that there were 19 cells showing one bright spot, 28 cells showing two bright spots, 2 cells showing three bright spots and 1 cell showing four bright spots. The bright spots were also observable in the fluorescence microscope observation.

TABLE 2

| | DNA clone | | Probe reagent | Substrate used in nick translation (uL) | | | DNA clone:label (molar ratio) | Phosphor | | Particle size (nm) |
| | Number of bases | | | Biotin-d-UTP | dTTP | dNTP | | | Base material | |
|---|---|---|---|---|---|---|---|---|---|---|
| Comparative Example 3 | 150,000 | HER2 | K | 0.2 | 1.5 | 5 | 1:2,000 | Q-dot | — | 15 |
| Comparative Example 4 | 300 | HER2 | L | 1.5 | 0.5 | 5 | 1:40 | Q-dot | — | 15 |
| Example 6 | 300 | HER2 | M | 1.5 | 0.5 | 5 | 1:40 | PID | melamine resin | 40 |
| Example 7 | 300 | HER2 | N | 1.5 | 0.5 | 5 | 1:40 | PID | melamine resin | 158 |
| Example 8 | 300 | HER2 | O | 1.5 | 0.5 | 5 | 1:40 | PID | melamine resin | 280 |
| Example 9 | 300 | HER2 | P | 1.5 | 0.5 | 5 | 1:40 | PID | melamine resin | 320 |
| Example 10 | 300 | HER2 | Q | 0.2 | 1.5 | 5 | 1:5 | PID | melamine resin | 160 |
| Example 11 | 300 | HER2 | R | 0.2 | 1.5 | 5 | 1:5 | PID | melamine resin | 320 |
| Example 12 | 150,000 | HER2 | S | 0 | 1.5 | 5 | 1:50 | PID | melamine resin | 160 |
| Comparative Example 5 | 150,000 | HER2 | Ad1 | | | | 1:1 | Q-dot | — | 15 |
| Comparative Example 6 | 300 | HER2 | Ad2 | | | | 1:1 | Q-dot | — | 15 |
| Example 13 | 150,000 | HER2 | Ad3 | | | | 1:1 | PID | melamine resin | 158 |
| Example 14 | 300 | HER2 | Ad4 | | | | 1:1 | PID | melamine resin | 158 |

TABLE 2-continued

|  | Labeling ratio (%) | Confocal microscope | | | | Fluorescence microscope | | | |
|---|---|---|---|---|---|---|---|---|---|
|  |  | 1 bright spot | 2 bright spots | 3 bright spots | 4 bright spots | 1 bright spot | 2 bright spots | 3 bright spots | 4 bright spots |
| Comparative Example 3 | 1.33 | 20 | 22 | 5 | 3 | No bright spot was observable. | | | |
| Comparative Example 4 | 13.33 | 20 | 29 | 1 | 0 | No bright spot was observable. | | | |
| Example 6 | 13.33 | 21 | 29 | 0 | 0 | 21 | 29 | 0 | 0 |
| Example 7 | 13.33 | 19 | 29 | 2 | 0 | 20 | 29 | 1 | 0 |
| Example 8 | 13.33 | 21 | 29 | 0 | 0 | 21 | 29 | 0 | 0 |
| Example 9 | 13.33 | 43 | 7 | 0 | 0 | 44 | 6 | 0 | 0 |
| Example 10 | 1.67 | 19 | 29 | 2 | 0 | 20 | 29 | 1 | 0 |
| Example 11 | 1.67 | 40 | 10 | 0 | 0 | 44 | 6 | 0 | 0 |
| Example 12 | 3.33E−4 | 19 | 29 | 2 | 0 | 25 | 24 | 1 | 0 |
| Comparative Example 5 | 6.67E−3 | 12 | 13 | 15 | 10 | No bright spot was observable. | | | |
| Comparative Example 6 | 0.33 | 21 | 27 | 2 | 0 | No bright spot was observable. | | | |
| Example 13 | 6.67E−3 | 21 | 26 | 9 | 4 | Bright spots were observed. | | | |
| Example 14 | 0.33 | 19 | 28 | 2 | 1 | Bright spots were observed. | | | |

*PID = phosphor-integrated nanoparticle

Example 15

Preparation of Short DNA Probe Having Biotin Labeling Ratio of 0.33%

A 300-base cDNA (nucleic acid molecule) having a HER2 gene-related sequence was prepared in the same manner as in Example 10.
<Biotin Labeling of 5'-End>
Using 2 μg of the thus prepared cDNA, a cDNA labeled with biotin at the 5'-end was obtained in the same manner as in Example 12.
<Preparation of Texas Red Dye-Containing Silica Nanoparticles Labeled with Streptavidin>
Texas Red dye-containing silica nanoparticles were prepared in the same manner as in Example 2, except that the amount of 28% aqueous ammonia was changed from 1.4 mL to 2.6 mL. As a result of SEM observation of 1,000 of the thus obtained particles, their average particle size was found to be 320 nm.
While preparing phosphor-integrated nanoparticles having a maleimide group from the thus obtained dye-containing nanoparticles in the same manner as in Example 2, a streptavidin solution was also prepared in the same manner as in Example 2. From these, Texas Red dye-containing silica nanoparticles (phosphor-integrated nanoparticles) bound with streptavidin were obtained in the same manner as in Example 2.
<Preparation of DNA Probe in which Phosphor-Integrated Nanoparticles (320 nm, Silica Particles) are Bound to 5'-End of Nucleic Acid Molecule>
The thus obtained cDNA labeled with biotin at the 5'-end in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent T).
<Other Observation, Etc.>
Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.
(Results)
As a result of measuring bright spots in the confocal fluorescence microscope observation, it was found that there were 40 cells showing one bright spot and 10 cells showing two bright spots, with no cell showing three or four bright spots. Further, as a result of measuring bright spots in the fluorescence microscope observation, it was found that there were 44 cells showing one bright spot and 6 cells showing two bright spots, with no cell showing three or four bright spots.
In other words, even in fluorescence microscope observation where the detection sensitivity of bright spots was low, the probe reagent of Example 15, although having a binding molar ratio of 1:1 between the DNA and the phosphor-integrated nanoparticles and a larger average particle size of 320 nm than the probe reagent of Example 12, enabled to detect bright spots with almost the same accuracy as that in confocal fluorescence microscope observation where the detection sensitivity of bright spots was high. However, non-specific detection was made in a large amount.

Example 16

Preparation of Short DNA Probe Having Biotin Labeling Ratio of 5%

On the probe search engine "HD-FISH" (URL: www.h-dfish.eu/Find#probes.php), a unique sequence was searched by designating a specific region (from the 37,844,400th base to the 37,885,107th base) of human 17th chromosome, and a unique sequence following the sequence of the 37,844,479th to the 37,844,696th bases that exists in the specific region was searched and obtained. By requesting the synthesis of a nucleic acid based on the thus obtained sequence data, a 20-base DNA (nucleic acid molecule) having a HER2 gene-related sequence (5'-ACGCCTGATGGGTTAAT-GAG-3' (SEQ ID NO: 5)) was prepared.
<Biotin Labeling of 5'-End>
Using 4 µg of the thus prepared DNA, a DNA labeled with biotin at the 5'-end was obtained in the same manner as in Example 12.
<Preparation of Fluorescent Dye-Containing Polymelamine Particles Labeled with Streptavidin>
Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 5.25 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 40 nm. Further, a mixture containing fluorescent dye-containing phosphor-integrated nanoparticles having terminal maleimide was obtained in the same manner as in Example 3. Washing and the like were also performed in the same manner as in Example 3.
<Preparation of Streptavidin/Binding of Particles and Streptavidin>
Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.
<Preparation of DNA Probe in which Phosphor-Integrated Nanoparticles (40 nm, Melamine Particles) and DNA Having Biotin Labeling Ratio of 5% are Bound>
The above-prepared DNA labeled with biotin at the 5'-end in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent U).
<Other Observation, Etc.>
Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.
(Results)
As a result of measuring bright spots in the confocal fluorescence microscope observation, it was found that there were 18 cells showing one bright spot, 31 cells showing two bright spots and 1 cell showing three bright spots, with no cell showing four bright spots. Further, as a result of measuring bright spots in the fluorescence microscope observation, it was found that there were 20 cells showing one bright spot and 30 cells showing two bright spots, with no cell showing three or four bright spots.
In other words, according to the probe reagent of Example 16, since this probe reagent had a very short nucleic acid molecule of 20 bases and a binding molar ratio (DNA: biotin=DNA:phosphor-integrated nanoparticles) of 1:1, it was expected that bright spots would not be detectable; however, surprisingly, even in the fluorescence microscope observation where the detection sensitivity of bright spots was low, bright spots were detected with almost the same accuracy as in the confocal fluorescence microscope observation where the detection sensitivity of bright spots was high.

Example 17

Preparation of DNA Probe Having Biotin Labeling Ratio of 5%

A 20-base DNA (nucleic acid molecule) was prepared in the same manner as in Example 16.
<Biotin Labeling of 5'-End>
Using 2 µg of the thus prepared DNA, a DNA labeled with biotin at the 5'-end was obtained in the same manner as in Example 12.
<Preparation of Fluorescent Dye-Containing Polymelamine Particles Labeled with Streptavidin>
Fluorescent dye-containing polymelamine particles (phosphor-integrated nanoparticles) labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.65 g. As a result of SEM observation of 1,000 of the thus obtained nanoparticles, their average particle size was found to be 158 nm. Further, a mixture containing fluorescent dye-containing phosphor-integrated nanoparticles having terminal maleimide was obtained in the same manner as in Example 3. Washing and the like were also performed in the same manner as in Example 3.
<Preparation of Streptavidin/Binding of Particles and Streptavidin>
Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.
<Preparation of DNA Probe in which Phosphor-Integrated Nanoparticles (158 nm, Melamine Particles) and DNA Having Biotin Labeling Ratio of 5% are Bound>
The above-prepared DNA labeled with biotin at the 5'-end in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent V).
<Other Observation, Etc.>
Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.

(Results)

As a result of measuring bright spots in the confocal fluorescence microscope observation, it was found that there were 20 cells showing one bright spot, 29 cells showing two bright spots and 1 cell showing three bright spots, with no cell showing four bright spots. Further, as a result of measuring bright spots in the fluorescence microscope observation, it was found that there were 29 cells showing one bright spot and 21 cells showing two bright spots, with no cell showing three or four bright spots.

In other words, even in fluorescence microscope observation where the detection sensitivity of bright spots was low, as in Example 16, the probe reagent of Example 17, although having a larger average particle size than the probe reagent of Example 16, enabled to detect bright spots with almost the same accuracy as that in confocal fluorescence microscope observation where the detection sensitivity of bright spots was high.

Example 18

Preparation of DNA Probe Having Biotin Labeling Ratio of 5%

A 20-base DNA (nucleic acid molecule) was prepared in the same manner as in Example 16.
<<Biotin Labeling of 5'-End>>

Using 2 μg of the thus prepared DNA, a DNA labeled with biotin at the 5'-end was obtained in the same manner as in Example 12.
<<Preparation of Fluorescent Dye-Containing Polymelamine Particles Labeled with Streptavidin>>

Fluorescent dye-containing polymelamine particles labeled with streptavidin were prepared in the same manner as in Example 7. As a result of SEM observation of 1,000 of the thus obtained nanoparticles, their average particle size was found to be 280 nm. Further, a mixture containing fluorescent dye-containing phosphor-integrated nanoparticles having terminal maleimide was obtained in the same manner as in Example 7. Washing and the like were also performed in the same manner as in Example 7.
(Preparation of Streptavidin/Binding of Particles and Streptavidin)

Meanwhile, streptavidin capable of binding to the phosphor-integrated nanoparticles was prepared and binding of the phosphor-integrated nanoparticles and the thus prepared streptavidin was performed in the same manner as in Example 7, thereby obtaining phosphor-integrated nanoparticles bound with streptavidin.
<<Preparation of DNA Probe in which Phosphor-Integrated Nanoparticles (280 nm, Melamine Particles) and DNA Having Biotin Labeling Ratio of 5% are Bound>>

The above-prepared DNA labeled with biotin at the 5'-end in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent W).
<Other Observation, Etc.>

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.
(Results)

As a result of measuring bright spots in the confocal fluorescence microscope observation, it was found that there were 21 cells showing one bright spot and 29 cells showing two bright spots, with no cell showing three or four bright spots. Further, as a result of measuring bright spots in the fluorescence microscope observation, it was found that there were 20 cells showing one bright spot and 30 cells showing two bright spots, with no cell showing three or four bright spots.

In other words, even in fluorescence microscope observation where the detection sensitivity of bright spots was low, as in Example 16 and the like, the probe reagent of Example 18, although having a larger average particle size than the probe reagents of Examples 16 and 17, enabled to detect bright spots with almost the same accuracy as that in confocal fluorescence microscope observation where the detection sensitivity of bright spots was high.

TABLE 3

| | DNA clone | | Substrate used in nick translation (uL) | | | DNA | Phosphor | |
| --- | --- | --- | --- | --- | --- | --- | --- | --- |
| | Number of bases | Probe reagent | Biotin-d-UTP | dTTP | dNTP | clone:label (molar ratio) | Base material | Particle size (nm) |
| Example 15 | 300 | HER2 | T | | | 1:1 | PID silica | 320 |
| Example 16 | 20 | HER2 | U | | | 1:1 | PID melamine resin | 40 |
| Example 17 | 20 | HER2 | V | | | 1:1 | PID melamine resin | 158 |
| Example 18 | 20 | HER2 | W | | | 1:1 | PID melamine resin | 280 |

| | | Confocal microscope | | | | Fluorescence microscope | | | |
| --- | --- | --- | --- | --- | --- | --- | --- | --- | --- |
| | Labeling ratio (%) | 1 bright spot | 2 bright spots | 3 bright spots | 4 bright spots | 1 bright spot | 2 bright spots | 3 bright spots | 4 bright spots |
| Example 15 | 0.33 | 40 | 10 | 0 | 0 | 44 | 6 | 0 | 0 |
| Example 16 | 5.00 | 18 | 31 | 0 | 0 | 20 | 30 | 0 | 0 |

TABLE 3-continued

| | | | | | | | | | |
|---|---|---|---|---|---|---|---|---|---|
| Example 17 | 5.00 | 20 | 29 | 1 | 0 | 39 | 21 | 0 | 0 |
| Example 18 | 5.00 | 21 | 29 | 0 | 0 | 20 | 30 | 0 | 0 |

*PID = phosphor-integrated nanoparticle

Reference Example 4

Using the probe reagent obtained in Reference Example 1, bright spots were observed under a fluorescence microscope immediately after the staining as well as one week, one month and two months after the staining, and the average number of bright spots in cells (cultured SKBR3 cells) of a specimen slide was examined for each time point. The average number of bright spots was determined by measuring the number of bright spots contained in 50 nuclei of the cells and calculating the average number of bright spots per nucleus.
<Results and Discussion>
The average number of bright spots after the staining was: 18 immediately after the staining; 15 after one week from the staining; 8 after one month from the staining; and 2 after two months from the staining. In other words, according to the probe reagent of Reference Example 1, the number of bright spots measurable immediately after the staining decreased with time and the resistance to dye-fading was thus poor (see Table 4).

Reference Example 5

Preparation of BAC Probe Having Biotin Labeling Ratio of 13.33%

A solution of biotin-labeled 150,000-base BAC probe (nucleic acid molecule) having a final concentration of 1 µg/250 µL was obtained by the same procedures as in Example 1. This solution was mixed with a solution containing 1.0 µL (50 nmol/50 µL) of purchased streptavidin-modified TXR ("Streptavidin, Texas Red Conjugate" manufactured by Funakoshi Co., Ltd. (product number: SA-5006)) to perform binding reaction at room temperature for 30 minutes, thereby obtaining a DNA probe for HER2 detection (probe reagent X).
<Verification of DNA Probe>
The thus obtained DNA probe was verified by an electrophoretic shift assay where the DNA probe in a 0.5% modified Tris-borate-EDTA (TBE) buffer was electrophoresed through a 0.5% TBE-containing 2% agarose gel. Single-stranded DNA was counter-stained with SYBR Green II (Molecular Probes, Eugene, Oreg.). Then, the migration pattern of DNA was determined as described below using "MultiImager FX System." (Bio-Rad, Hercules, Calif.).
That is, TXR existing in the electrophoresed gel was checked using a laser light having a wavelength of 590 nm as an excitation light along with a 615-nm bandpass emission filter. As for the verification of the binding molar ratio of the BAC probe and biotin, the binding molar ratio was determined to be 1:20,000 by a HABA-avidin method using "Thermo Scientific Pierce Biotin Quantitation Kit" (manufactured by Thermo Fisher Scientific K. K.) where, with HABA being bound to streptavidin of the TXR, HABA was substituted with biotin of the DNA.
[Other Observation, Etc.]
Storage of the DNA probe, FISH, bright-field observation, confocal fluorescence microscope observation, fluorescence microscope observation and the like were performed in the same manner as in Comparative Example 3. Bright spots were observed in both the confocal fluorescence microscope observation and the fluorescence microscope observation.
<Evaluation of Dye-Fading>
Evaluation of dye-fading was performed in the above-described fluorescence microscope observation in the same manner as in Reference Example 4.
<Results and Discussion>
Bright spots were observed in both the confocal fluorescence microscope observation and the fluorescence microscope observation. The average number of bright spots after the staining was: 20 immediately after the staining; 15 after one week from the staining; 9 after one month from the staining; and 3 after two months from the staining.
In other words, according to the probe reagent of Reference Example 5, the number of bright spots measurable immediately after the staining decreased with time and the dye-fading resistance was thus poor (see Table 4).

Example 19

Preparation of DNA Probe Having Biotin Labeling Ratio of 1.67%

A 300-base cDNA (nucleic acid molecule) having a HER2 gene-related sequence was prepared in the same manner as in Example 6. Phosphor-integrated nanoparticles were prepared by the below-described method and then directly bound to the thus obtained cDNA.
<Preparation of Fluorescent Dye-Containing Polymelamine Particles Labeled with Streptavidin>
Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 5.25 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 40 nm.
<Direct Binding of Phosphor-Integrated Nanoparticles and cDNA>
After mixing 1 µL of "Amino-11-dUTP" manufactured by Lumiprobe Corporation with N-succinimidyl-S-acetylthioglycolate (SATA) and incubating the resulting mixture at 5° C. for 1 hour to perform a thiol group addition treatment, the resultant was filtered through a gel filtration column to obtain a solution of thiol-11-dUTP capable of binding to the phosphor-integrated nanoparticle.
The above-obtained phosphor-integrated nanoparticles having a terminal maleimide group and thiol-11-dUTP solution were mixed in PBS containing 2 mM of EDTA and allowed to react at 5° C. for 1 hour. Then, the reaction was terminated with an addition of 10 mM mercaptoethanol. After concentrating the resulting solution using a centrifugation filter, unreacted materials were removed using a gel-filtration column for purification, thereby obtaining 1.0

μL of Texas Red dye-containing melamine resin particles bound with dUTP as phosphor-integrated nanoparticles.
<Labeling Method by Nick Translation>
First, the following reagents were mixed in a centrifuge tube.
10× Nick Buffer (Tris-HCl [pH 7.2], MgSO$_4$, DTT): 2.5 μL
BSA (nuclease-free BSA): 1.5 μL
dNTP mix (dATP, dCTP, dCTP): 5 μL
dTTP: 1.5 μL
dUTP-bound Texas Red dye-containing melamine resin particles: 0.2 μL
pure water (nuclease-free water): 3 μL
an aqueous solution containing 1 μg of the above-described cDNA: 5 μL
DNA polymerase I (Tris-HCl [pH 7.5], EDTA, DTT, glycerol): 1 μL
DNAse I: 5 μL Next, the resulting mixture was allowed to react at 15° C. for 4 hours, and the reaction was terminated by heating the mixture at 70° C. for 10 minutes. Then, 25 μL of distilled water was added to the centrifuge tube. The resulting reaction solution of a biotin-labeled BAC probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-bound cDNA (probe reagent Y) (final concentration: 1 μg/250 μL).

[Other Observation, Etc.]
Verification of the DNA probe, storage of the DNA probe, FISH, bright-field observation, confocal fluorescence microscope observation, fluorescence microscope observation and the like were performed in the same manner as in Comparative Example 3.

In the verification of the DNA probe, the binding molar ratio of the cDNA and the phosphor-integrated nanoparticles could not be verified by a HABA-avidin method and there is no other evaluation system; however, since the preparation of the DNA probe was performed using the same materials under the same conditions as in Example 10, the binding molar ratio is estimated to be 1:5.

<Evaluation of Dye-Fading>
Evaluation of dye-fading was performed in the above-described fluorescence microscope observation in the same manner as in Reference Example 4.
<Results and Discussion>
Bright spots were observed in both the confocal fluorescence microscope observation and the fluorescence microscope observation. The average number of bright spots after the staining was: 26 immediately after the staining; 27 after one week from the staining; 24 after one month from the staining; and 24 after two months from the staining. In other words, according to the probe reagent of Example 19, the number of bright spots measurable immediately after the staining did not decrease with time and the resistance to dye-fading was thus high (see Table 4).

Example 20

Using the probe reagent obtained in Example 8, evaluation of dye-fading was performed in the fluorescence microscope observation in the same manner as in Reference Example 4.
<Results and Discussion>
The average number of bright spots after the staining was: 25 immediately after the staining; 25 after one week from the staining; 26 after one month from the staining; and 24 after two months from the staining. In other words, according to the probe reagent of Example 20, the number of bright spots measurable immediately after the staining did not decrease with time and the resistance to dye-fading was thus high (see Table 4).

Example 21

Using the probe reagent obtained in Example 9, evaluation of dye-fading was performed in the fluorescence microscope observation in the same manner as in Reference Example 4.
<Results and Discussion>
The average number of bright spots after the staining was: 11 immediately after the staining; 11 after one week from the staining; 11 after one month from the staining; and 10 after two months from the staining. In other words, according to the probe reagent of Example 21, the number of bright spots measurable immediately after the staining did not decrease with time and the resistance to dye-fading was thus high (see Table 4).

Example 22

Preparation of DNA Probe Having Biotin Labeling Ratio of 13.33%

A 300-base cDNA (nucleic acid molecule) having a HER2 gene-related sequence was prepared in the same manner as in Example 6.
<Biotin Labeling by Nick Translation>
Using 1 μg of the thus obtained cDNA, nick translation was performed in the same manner as in Example 1, thereby obtaining a solution of a biotin-labeled cDNA having a final concentration of 1 μg/250 μL.
<Preparation of Fluorescent Dye-Containing Polymelamine Particles Labeled with Streptavidin>
FITC (code P76012, manufactured by Takara Bio Inc.) in an amount of 4.1 mg was added to and dissolved in 22 mL of water. Then, to this solution, 2 mL of a 5% aqueous solution of an emulsifier for emulsion polymerization, EMULGEN (registered trademark) 430 (polyoxyethylene oleyl ether, manufactured by Kao Corporation), was added. The resulting solution was heated to 70° C. with stirring on a hot stirrer, and 0.15 g of a melamine resin material, NIKALAC MX-035 (manufactured by Nippon Carbide Industries Co., Inc.), was subsequently added thereto.

To this solution, as a surfactant, 1,000 μL of a 10% aqueous solution of dodecylbenzenesulfonic acid (manufactured by Kanto Chemical Co., Inc.) was further added, and the resultant was heated with stirring at 70° C. for 50 minutes. Thereafter, the resultant was further heated with stirring at 90° C. for 20 minutes. The resulting dispersion of phosphor-integrated nanoparticles was washed with pure water so as to remove impurities such as excess resin material and fluorescent dye.

Specifically, the dispersion was centrifuged at 20,000 G for 15 minutes using a centrifugal machine (Micro Refrigerated Centrifuge 3740, manufactured by Kubota Corporation) and, after removing the resulting supernatant, the precipitates were re-dispersed in ultrapure water by ultrasonication. The centrifugation, the removal of supernatant and the washing by re-dispersion in ultrapure water were repeated five times. In the thus obtained melamine particles, the melamine resin itself contained a large number of amino groups in its skeleton. As a result of SEM observation of 1,000 of the thus obtained nanoparticles, their average particle size was found to be 35 nm.

Then, 0.1 mg of the thus obtained phosphor-integrated nanoparticles was dispersed in 1.5 mL of ethanol, and 2 µL of aminopropyltrimethoxysilane (LS-3150, manufactured by Shin-Etsu Chemical Co., Ltd.) was added thereto. The resulting mixture was allowed to react for 8 hours so as to perform a surface amination treatment, thereby converting the hydroxyl groups existing on the surface of the phosphor-integrated resin nanoparticles to amino groups.

The resulting phosphor-integrated nanoparticles were adjusted with a phosphate-buffered physiological saline (PBS) containing 2 mM of ethylenediamine tetraacetic acid (EDTA) to a concentration of 3 nM. The resulting dispersion of the phosphor-integrated nanoparticles having the adjusted concentration was mixed with $SM(PEG)_{12}$ (succinimidyl-[(N-maleimidopropionamido)-dodecaethylene glycol]ester, manufactured by Thermo Fisher Scientific K.K.) to a final concentration of 10 mM, and the resultant was allowed to react at 20° C. for 1 hour, thereby obtaining a mixture containing fluorescent dye-containing phosphor-integrated nanoparticles having terminal maleimide.

This mixture was centrifuged at 10,000 G for 20 minutes and the resulting supernatant was removed. Then, the precipitates were dispersed by adding thereto PBS containing 2 mM of EDTA, and the resulting dispersion was centrifuged again. The precipitates were washed three times by the same procedure.

<Preparation of Streptavidin>

Meanwhile, streptavidin (manufactured by Wako Pure Chemical Industries, Ltd.) was subjected to a thiol group addition treatment with N-succinimidyl-S-acetylthioacetate (abbreviated as "SATA"), and the resultant was subjected to gel filtration to separately prepare streptavidin capable of binding to the phosphor-integrated nanoparticles.

<Binding of Phosphor-Integrated Nanoparticles and Streptavidin>

The above-described phosphor-integrated nanoparticles and streptavidin were mixed in PBS containing 2 mM of EDTA and allowed to react at room temperature for 1 hour, thereby binding the phosphor-integrated nanoparticles with streptavidin. Then, the reaction was terminated with an addition of 10 mM mercaptoethanol. After concentrating the resulting solution using a centrifugation filter ($\varphi=0.65$ µm), unreacted streptavidin and the like were removed using a gel-filtration column for purification, thereby obtaining phosphor-integrated nanoparticles bound with streptavidin.

<Preparation of DNA Probe in which Phosphor-Integrated Nanoparticles (35 nm, Melamine Particles) and cDNA Having Biotin Labeling Ratio of 13.33% are Bound>

The biotin-labeled cDNA obtained above in an amount of 25 µL (concentration: 1 µg/250 µL) and a solution containing the phosphor-integrated nanoparticles having streptavidin were mixed to perform binding reaction at room temperature for 30 minutes, thereby obtaining a DNA probe for HER2 detection (probe reagent Z).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Evaluation of Dye-Fading>

In the above-described fluorescence microscope observation, bright spots were observed immediately after the staining as well as one week, one month and two months after the staining, and the average number of bright spots in cells (cultured SKBR3 cells) of a specimen slide was examined for each time point. The average number of bright spots was determined by measuring the number of bright spots contained in 50 nuclei of the cells and calculating the average number of bright spots per nucleus.

<Results and Discussion>

Bright spots were observed in both the confocal fluorescence microscope observation and the fluorescence microscope observation. The average number of bright spots after the staining was: 15 immediately after the staining; 16 after one week from the staining; 15 after one month from the staining; and 13 after two months from the staining. In other words, according to the probe reagent of Example 22, the number of bright spots measurable immediately after the staining did not decrease with time and the resistance to dye-fading was thus high (see Table 4).

Example 23

Preparation of DNA Probe Having Biotin Labeling Ratio of 13.33%

A 300-base cDNA (nucleic acid molecule) having a HER2 gene-related sequence was prepared in the same manner as in Example 6.

<Biotin Labeling by Nick Translation>

The thus obtained cDNA in an amount of 1 µg was labeled with biotin by nick translation in the same manner as in Example 1.

<Preparation of Fluorescent Dye-Containing Polymelamine Particles Labeled with Streptavidin>

Fluorescent dye-containing polymelamine particles were prepared in the same manner as in Example 22, except that the amount of FITC (code P76012, manufactured by Takara Bio Inc.) was changed to 5.25 mg and the amount of the melamine resin material NIKALAC MX-035 (manufactured by Nippon Carbide Industries Co., Inc.) was changed to 0.21 g. In the thus obtained melamine particles, the melamine resin itself contained a large number of amino groups in its skeleton. As a result of SEM observation of 1,000 of the thus obtained nanoparticles, their average particle size was found to be 40 nm.

While preparing fluorescent dye-containing particles having a maleimide group from the thus obtained dye-containing nanoparticles in the same manner as in Example 22, a streptavidin solution was also prepared in the same manner as in Example 22. From these, FITC dye-containing melamine particles (phosphor-integrated nanoparticles) bound with streptavidin were obtained in the same manner as in Example 22.

<Preparation of DNA Probe in which Phosphor-Integrated Nanoparticles (Average Particle Size: 40 nm, Melamine Particles) and cDNA Having Biotin Labeling Ratio of 13.33% are Bound>

The biotin-labeled cDNA obtained above in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent A1).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3.

As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Evaluation of Dye-Fading>

Evaluation of dye-fading was performed in the above-described fluorescence microscope observation in the same manner as in Reference Example 4.

<Results and Discussion>

Bright spots were observed in both the confocal fluorescence microscope observation and the fluorescence microscope observation. The average number of bright spots after the staining was: 26 immediately after the staining; 25 after one week from the staining; 26 after one month from the staining; and 25 after two months from the staining.

In other words, according to the probe reagent of Example 23, the number of bright spots measurable immediately after the staining did not decrease with time and the resistance to dye-fading was thus high (see Table 3).

Example 24

Preparation of DNA Probe Having Biotin Labeling Ratio of 1.67%

A 300-base cDNA (nucleic acid molecule) having a HER2 gene-related sequence was prepared in the same manner as in Example 6.

A solution of biotin-labeled cDNA probe having a final concentration of 1 μg/250 μL was obtained in the same manner as in Example 1, except that, in the biotin labeling by nick translation, the amount of dTTP was changed from 0.5 μL to 1.5 μL and the amount of Biotin-16-dUTP (product number: 1093070, manufactured by Roche, 50 nmol/50 μL) was changed from 1.5 μL to 0.2 μL.

<Preparation of Fluorescent Dye-Containing Polymelamine Particles Labeled with Streptavidin>

Fluorescent dye-containing polymelamine particles were prepared in the same manner as in Example 22, except that the amount of FITC (code P76012, manufactured by Takara Bio Inc.) was changed to 14.4 mg and the amount of the melamine resin material NIKALAC MX-035 (manufactured by Nippon Carbide Industries Co., Inc.) was changed to 0.65 g. In the thus obtained melamine particles, the melamine resin itself contained a large number of amino groups in its skeleton. As a result of SEM observation of 1,000 of the thus obtained nanoparticles, their average particle size was found to be 158 nm.

While preparing fluorescent dye-containing particles having a maleimide group from the thus obtained dye-containing nanoparticles in the same manner as in Example 22, a streptavidin solution was also prepared in the same manner as in Example 22. From these, FITC dye-containing melamine particles (phosphor-integrated nanoparticles) bound with streptavidin were obtained in the same manner as in Example 22.

<Preparation of DNA Probe in which Phosphor-Integrated Nanoparticles (Average Particle Size: 158 nm, Melamine Particles) and cDNA Having Biotin Labeling Ratio of 1.67% are Bound>

The biotin-labeled cDNA obtained above in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent A2).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:5 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Evaluation of Dye-Fading>

Evaluation of dye-fading was performed in the above-described fluorescence microscope observation in the same manner as in Reference Example 4.

(Results and Discussion)

Bright spots were observed in both the confocal fluorescence microscope observation and the fluorescence microscope observation. The average number of bright spots after the staining was: 27 immediately after the staining; 24 after one week from the staining; 25 after one month from the staining; and 25 after two months from the staining.

In other words, according to the probe reagent of Example 24, the number of bright spots measurable immediately after the staining did not decrease with time and the resistance to dye-fading was thus high (see Table 3).

Example 25

Preparation of Short DNA Probe Having Biotin Labeling Ratio of 13.33%

A 300-base cDNA (nucleic acid molecule) having a HER2 gene-related sequence was prepared in the same manner as in Example 6.

The thus obtained cDNA in an amount of 1 μg was labeled with biotin by nick translation in the same manner as in Example 1, thereby obtaining a solution of a biotin-labeled cDNA having a final concentration of 1 μg/250 μL.

<Preparation of Fluorescent Dye-Containing Polymelamine Particles Labeled with Streptavidin>

Fluorescent dye-containing polymelamine particles were prepared in the same manner as in Example 22, except that the amount of FITC (code P76012, manufactured by Takara Bio Inc.) was changed to 20.3 mg and the amount of the melamine resin material NIKALAC MX-035 (manufactured by Nippon Carbide Industries Co., Inc.) was changed to 0.81 g. In the thus obtained melamine particles, the melamine resin itself contained a large number of amino groups in its skeleton. As a result of SEM observation of 1,000 of the thus obtained nanoparticles, their average particle size was found to be 280 nm.

While preparing fluorescent dye-containing particles having a maleimide group from the thus obtained dye-containing nanoparticles in the same manner as in Example 22, a streptavidin solution was also prepared in the same manner as in Example 22. From these, FITC dye-containing melamine particles (phosphor-integrated nanoparticles) bound with streptavidin were obtained in the same manner as in Example 22.

<Preparation of DNA Probe in which Phosphor-Integrated Nanoparticles (280 nm, Melamine Particles) and cDNA Having Biotin Labeling Ratio of 13.33% are Bound>

The biotin-labeled cDNA obtained above in an amount of 25 μL (concentration: 1 μg/250 μL) and a solution containing the phosphor-integrated nanoparticles modified with streptavidin were mixed to perform binding reaction at room temperature for 30 minutes, thereby obtaining a DNA probe for HER2 detection (probe reagent A3).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Evaluation of Dye-Fading>

Evaluation of dye-fading was performed in the above-described fluorescence microscope observation in the same manner as in Reference Example 4.

<Results and Discussion>

Bright spots were observed in both the confocal fluorescence microscope observation and the fluorescence microscope observation. The average number of bright spots after the staining was: 24 immediately after the staining; 24 after one week from the staining; 22 after one month from the staining; and 21 after two months from the staining. In other words, according to the probe reagent of Example 25, the number of bright spots measurable immediately after the staining did not decrease with time and the resistance to dye-fading was thus high (see Table 3).

Example 26

Preparation of DNA Probe Having Biotin Labeling Ratio of 0.5%

A 200-base HER2-DNA clone was prepared in accordance with the method described in Bienko M. Nat Methods (2013). That is, HER2-selective sequences were found by database search and a 200-base cDNA (nucleic acid molecule) was prepared using a forward primer (5'-ACGCCTGATGGGTTAATGAG-3' (SEQ ID NO: 6)) and a reverse primer (5'-aagtagaggcagggagagcc-3' (SEQ ID NO: 7)).

<Biotin Labeling of 5'-End>

Using 2 μg of the thus prepared cDNA, a cDNA labeled with biotin at the 5'-end was obtained in the same manner as in Example 12.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.

(Preparation of Streptavidin/Binding of Particles and Streptavidin)

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.

<Preparation of DNA Probe in which Phosphor-Integrated Nanoparticles (158 nm, Melamine Particles) and cDNA Having Biotin Labeling Ratio of 0.5% are Bound>

The thus obtained cDNA labeled with biotin at the 5'-end in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent A4).

<Other Observation, Etc.>

Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the cDNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

<Evaluation of Dye-Fading>

Evaluation of dye-fading was performed in the above-described fluorescence microscope observation in the same manner as in Reference Example 4.

(Results and Discussion)

Bright spots were observed in both the confocal fluorescence microscope observation and the fluorescence microscope observation. The average number of bright spots after the staining was: 27 immediately after the staining; 27 after one week from the staining; 25 after one month from the staining; and 25 after two months from the staining. In other words, according to the probe reagent of Example 26, the number of bright spots measurable immediately after the staining did not decrease with time and the resistance to dye-fading was thus high (see Table 4).

Example 27

Preparation of DNA Probe Having Biotin Labeling Ratio of 5%

A 20-base DNA (nucleic acid molecule) was prepared in the same manner as in Example 16.
<Biotin Labeling of 5'-End>
Using 2 μg of the thus prepared DNA, a DNA labeled with biotin at the 5'-end was obtained in the same manner as in Example 12.
<Preparation of Fluorescent Dye-Containing Polymelamine Particles Labeled with Streptavidin>
Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.
(Preparation of Streptavidin/Binding of Particles and Streptavidin)
Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.
<Preparation of DNA Probe in which Phosphor-Integrated Nanoparticles (158 nm, Melamine Particles) and DNA Having Biotin Labeling Ratio of 5% are Bound>
The thus obtained DNA labeled with biotin at the 5'-end in an amount of 25 μL (concentration: 1 μg/250 μL) and a solution containing the phosphor-integrated nanoparticles having streptavidin were mixed to perform binding reaction at room temperature for 30 minutes, thereby obtaining a DNA probe for HER2 detection (probe reagent A5).
<Other Observation, Etc.>
Verification of the DNA probe, storage of the DNA probe, FISH, bright-field observation, confocal fluorescence microscope observation, fluorescence microscope observation and the like were performed in the same manner as in Comparative Example 3. As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.
<Evaluation of Dye-Fading>
Evaluation of dye-fading was performed in the above-described fluorescence microscope observation in the same manner as in Reference Example 4.

(Results)
Bright spots were observed in both the confocal fluorescence microscope observation and the fluorescence microscope observation. The average number of bright spots after the staining was: 26 immediately after the staining; 25 after one week from the staining; 26 after one month from the staining; and 26 after two months from the staining. In other words, according to the probe reagent of Example 27, the number of bright spots measurable immediately after the staining did not decrease with time and the resistance to dye-fading was thus high (see Table 4).

Example 28

Preparation of DNA Probe Having Biotin Labeling Ratio of 0.5%

A 200-base cDNA (nucleic acid molecule) was prepared in the same manner as in Example 26.
<Preparation of Fluorescent Dye-Containing Polymelamine Particles Labeled with Streptavidin>
(Preparation of Particles)
Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.
<Direct Binding of Phosphor-Integrated Nanoparticles and cDNA (5'-End Labeling)>
For 2 μg of the above-prepared cDNA, using a kit "5' EndTag™ Nucleic Acid Labeling System (catalog No. MB-9001)" manufactured by Vector Laboratories, Inc. in accordance with its protocol, the 5'-end of the nucleic acid molecule was converted from phosphoric acid to thiophosphoric acid as described below.

The following materials were mixed in a centrifuge tube and incubated at 37° C. for 30 minutes.
  nucleic acid molecule of the cDNA: 2 μg (/8 μL of ultrapure water)
  Universal reaction buffer: 1 μL
  alkaline phosphatase: 1 μL
In addition, the resulting mixture was further mixed with the following materials and incubated at 37° C. for 30 minutes.
  Universal reaction buffer: 2 μL
  ATPγS: 1 μL
  T4 polynucleotide kinase: 2 μL
Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-labeled cDNA (probe reagent A6) (final concentration: 1 μg/250 μL).

<Evaluation of Dye-Fading>

Evaluation of dye-fading was performed in the above-described fluorescence microscope observation in the same manner as in Reference Example 4.

(Results)

Bright spots were observed in both the confocal fluorescence microscope observation and the fluorescence microscope observation. The average number of bright spots after the staining was: 24 immediately after the staining; 24 after one week from the staining; 24 after one month from the staining; and 22 after two months from the staining. In other words, according to the probe reagent of Example 28, the number of bright spots measurable immediately after the staining did not decrease with time and the resistance to dye-fading was thus high.

Example 29

FISH, bright-field observation, confocal fluorescence microscope observation, fluorescence microscope observation and the like were performed in the same manner as in Example 12, except that, in FISH, hybridization was performed using the cDNA labeled with biotin at the 5'-end that was prepared in Example 28 (the cDNA before being bound with streptavidin of phosphor-integrated nanoparticles) in the same manner as in Example 1 and that 50 μg of the phosphor-integrated nanoparticles bound with streptavidin that was prepared in Example 12 was added to the reaction system to fluorescently label the cDNA.

<Evaluation of Dye-Fading>

Evaluation of dye-fading was performed in the above-described fluorescence microscope observation in the same manner as in Reference Example 4.

(Results)

Bright spots were observed in both the confocal fluorescence microscope observation and the fluorescence microscope observation. The average number of bright spots after the staining was: 26 immediately after the staining; 25 after one week from the staining; 24 after one month from the staining; and 25 after two months from the staining. In other words, even when a method where phosphor-integrated nanoparticles are added to the reaction system after hybridization and fluorescent labeling is performed in the post-hybridization reaction system was employed, the cells could be stained and the dye fading-inhibiting effect was attained in the same manner (see Table 4).

TABLE 4

| | DNA clone | | | Substrate used for nick translation (uL) | | | DNA | Labeling | Phosphor | |
|---|---|---|---|---|---|---|---|---|---|---|
| | Number of bases | | Probe reagent | Biotin-d-UTP | dTTP | dNTP | clone:label (molar ratio) | ratio (%) | | Base material |
| Reference Example 4 | 150,000 | HER2 | B | 1.5 | 0.5 | 5 | 1:20,000 | 13.33 | FITC | — |
| Reference Example 5 | 150,000 | HER2 | X | 1.5 | 0.5 | 5 | 1:20,000 | 13.33 | TXR | — |
| Example 19 | 300 | HER2 | Y | 0.2 | 1.5 | 5 | 1:5 | 1.67 | PID | melamine resin |
| Example 20 | 300 | HER2 | O | 1.5 | 0.5 | 5 | 1:40 | 13.33 | PID | melamine resin |
| Example 21 | 300 | HER2 | P | 1.5 | 0.5 | 5 | 1:40 | 13.33 | PID | melamine resin |
| Example 22 | 300 | HER2 | Z | 1.5 | 0.5 | 5 | 1:40 | 13.33 | PID | melamine resin |
| Example 23 | 300 | HER2 | A1 | 1.5 | 0.5 | 5 | 1:40 | 13.33 | PID | melamine resin |
| Example 24 | 300 | HER2 | A2 | 0.2 | 1.5 | 5 | 1:5 | 1.67 | PID | melamine resin |
| Example 25 | 300 | HER2 | A3 | 1.5 | 0.5 | 5 | 1:40 | 13.33 | PID | melamine resin |
| Example 26 | 200 | HER2 | A4 | | | | 1:1 | 0.5 | PID | melamine resin |
| Example 27 | 40 | HER2 | A5 | | | | 1:1 | 2.5 | PID | melamine resin |
| Example 28 | 200 | HER2 | A6 | | | | 1:1 | 0.5 | PID | melamine resin |
| Example 29 | 200 | HER2 | A7 | | | | 1:1 | 0.5 | PID | melamine resin |

| | Phosphor Particle size (nm) | Number of bright spots per nucleus of cultured SKBR3 cells observed under fluorescence microscope | | | | Fluorescence microscope |
|---|---|---|---|---|---|---|
| | | Immediately after staining | After 1 week | After 1 month | After 2 months | |
| Reference Example 4 | <1 | 18 | 15 | 8 | 2 | |

TABLE 4-continued

|  | *PID | | | | |
|---|---|---|---|---|---|
| Reference Example 5 | <1 | 20 | 15 | 9 | 3 |
| Example 19 | 40 | 26 | 27 | 24 | 24 |
| Example 20 | 280 | 25 | 25 | 26 | 24 |
| Example 21 | 320 | 11 | 11 | 11 | 10 |
| Example 22 | 35 | 15 | 16 | 15 | 13 |
| Example 23 | 40 | 26 | 25 | 26 | 25 |
| Example 24 | 158 | 27 | 24 | 25 | 25 |
| Example 25 | 280 | 24 | 24 | 22 | 21 |
| Example 26 | 158 | 27 | 27 | 25 | 25 |
| Example 27 | 158 | 26 | 25 | 26 | 26 |
| Example 28 | 158 | 24 | 24 | 24 | 22 |
| Example 29 | 158 | 26 | 25 | 24 | 25 |

*PID = phosphor-integrated nanoparticle

Example 30

FISH, bright-field observation, confocal fluorescence microscope observation, fluorescence microscope observation and the like were performed in the same manner as in Example 24 using the probe reagent obtained in Example 24, except that a tissue array of healthy individuals ("FDA normal organ tissue microarray of human" manufactured by US Biomax, Inc., product number: FDA999b) was used as a specimen slide in place of the slide of HER2-positive staining control specimen ("HER2-FISH Control Slide" manufactured by Pathology Institute Corp., code: PS-09006).

<Results and Discussion>

In the confocal microscope observation and fluorescence microscope observation, only those cells showing 2 bright spots were observed, and the HER2 gene was properly detected even in the fluorescence microscope observation where the detection sensitivity is lower than that of the confocal microscope observation.

Example 31

Preparation of DNA Probe Having Biotin Labeling Ratio of 8.46%

Using Applied Biosystems 392 DNA/RNA Synthesizer (Foster City, Calif.), a primer A (5'-TCTCAGCAACAT-GTCGATGG-3' (SEQ ID NO: 8)) and a primer B (5'-TCGCACTTCTTACACTTGCG-3' (SEQ ID NO: 9)) were prepared (see Clin. Cancer Res. 2000; 6:1439-1444).

Next, a 473-base cDNA (nucleic acid molecule) having an EGFR gene-related sequence was prepared by performing a reverse transcription reaction using total RNA extracted from HT-29 cells as a template along with a set of the above primers, "SuperScript (registered trademark) II Reverse Transcriptase" manufactured by Invitrogen Corp. and a common commercially available PCR reagent in accordance with the protocol described in the product manual of this reverse transcriptase.

Using 1 μg of the thus obtained cDNA, nick translation was performed in the same manner as in Example 1, thereby obtaining a solution of a biotin-labeled DNA having a final concentration of 1 μg/250 μL.

<Preparation of Fluorescent Dye-Containing Polymelamine Particles Labeled with Streptavidin>

Fluorescent dye FITC-containing polymelamine particles were prepared in the same manner as in Example 22, except that the amount of FITC (code P76012, manufactured by Takara Bio Inc.) was changed to 5.25 mg and the amount of the melamine resin material NIKALAC MX-035 (manufactured by Nippon Carbide Industries Co., Inc.) was changed to 0.21 g. In the thus obtained polymelamine particles, the melamine resin itself contained a large number of amino groups in its skeleton. As a result of SEM observation of 1,000 of the thus obtained polymelamine particles, their average particle size was found to be 40 nm.

While preparing polymelamine particles having a maleimide group from the thus obtained polymelamine particles in the same manner as in Example 2, a streptavidin solution was also prepared in the same manner as in Example 2. From these, FITC dye-containing melamine particles (phosphor-integrated nanoparticles) bound with streptavidin were obtained in the same manner as in Example 2.

<Preparation of DNA Probe in which Phosphor-Integrated Nanoparticles (40 nm, Melamine Particles) and DNA Having Biotin Labeling Ratio of 8.46% are Bound>

The biotin-labeled DNA obtained above in an amount of 25 μL (concentration: 1 μg/250 μL) and a solution containing the phosphor-integrated nanoparticles modified with streptavidin were mixed to perform binding reaction at room temperature for 30 minutes, thereby obtaining a DNA probe for EGFR detection (probe reagent A7).

[Other Observation, Etc.]

Verification of the DNA probe, storage of the DNA probe, FISH, bright-field observation, confocal fluorescence microscope observation, fluorescence microscope observation and the like were performed in the same manner as in Comparative Example 3.

As for the verification of the binding molar ratio of the DNA and biotin, the binding molar ratio was determined to be 1:40 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.

Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.

<Results and Discussion>

In the confocal microscope observation and fluorescence microscope observation, only those cells showing 2 bright spots were observed, and the EGFR gene was properly detected even in the fluorescence microscope observation where the detection sensitivity is lower than that of the confocal microscope observation.

Example 32

Preparation of DNA Probe Having Biotin Labeling Ratio of 0.21%

A 473-base cDNA (nucleic acid molecule) having an EGFR gene-related sequence was prepared and nick translation was performed in the same manner as in Example 31, except that the nick translation was performed without adding Biotin-d-UTP and the thus obtained DNA was biotinylated at the 5'-end in the same manner as in Example 12.

<<Preparation of Fluorescent Dye-Containing Polymelamine Particles Labeled with Streptavidin>>
(Preparation of Particles)

Fluorescent dye-containing polymelamine particles (phosphor-integrated nanoparticles) labeled with streptavidin were prepared in the same manner as in Example 1, except that the amount of SulfoRhodamine 101 (manufactured by Sigma-Aldrich) was changed from 20.3 mg to 14.4 mg and the amount of the melamine resin material NIKA-LAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 1. Washing and the like were also performed in the same manner as in Example 1.

<<Direct Binding of Phosphor-Integrated Nanoparticles and DNA (5'-End Labeling)>>

For 2 μg of the above-prepared DNA, using a kit "5' EndTag™ Nucleic Acid Labeling System (catalog No. MB-9001)" manufactured by Vector Laboratories, Inc. in accordance with its protocol, the 5'-end of the nucleic acid molecule was converted from phosphoric acid to thiophosphoric acid as described below.

The following materials were mixed in a centrifuge tube and incubated at 37° C. for 30 minutes.
nucleic acid molecule of the cDNA: 2 μg (/8 μL of ultrapure water)
Universal reaction buffer: 1 μL
alkaline phosphatase: 1 μL In addition, the resulting mixture was further mixed with the following materials and incubated at 37° C. for 30 minutes.
Universal reaction buffer: 2 μL
ATPγS: 1 μL
T4 polynucleotide kinase: 2 μL Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-labeled DNA (probe reagent A8) (final concentration: 1 μg/250 μL).

<Other Observation, Etc.>

Verification of the DNA probe, storage of the DNA probe, FISH, bright-field observation, confocal fluorescence microscope observation, fluorescence microscope observation and the like were performed in the same manner as in Example 20.

In the verification of the DNA probe, since only the 5'-end was labeled, the binding molar ratio was found to be 1:1. Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 31.

(Results and Discussion)

In the confocal microscope observation and fluorescence microscope observation, only those cells showing 2 bright spots were observed, and the EGFR gene was properly detected even in the fluorescence microscope observation where the detection sensitivity is lower than that of the confocal microscope observation.

Example 33

Preparation of DNA Probe Having Labeling Ratio of 0.5%

SEQ ID NOs of the EGFR gene (Chromosome 7: 55, 086, 714-55, 324, 313) obtained by a search on the gene database "e! Ensembl$^{ASIA}$" (asia.ensembl.org/index.html) were input and searched on the probe search engine "HD-FISH" (URL: www.hdfish.eu/Find#probes.php), and 610 EGFR primer pairs were found in accordance with the method described in Bienko M. Nat Methods (2013).

A 473-base cDNA (nucleic acid molecule) having an EGFR gene-related sequence was prepared by performing a reverse transcription reaction using total RNA extracted from HT-29 cells as a template along with a set of a forward primer (5'-CGGAGTCCAAGTGTCCTTTC-3' (SEQ ID NO: 10)) and a reverse primer (5'-CCTTCTATG-CAAAGGGCAAA-3' (SEQ ID NO: 11)) among EGFR-selective sequences as well as "SuperScript (registered trademark) II Reverse Transcriptase" manufactured by Invitrogen Corp. and a common commercially available PCR reagent in accordance with the protocol described in the product manual of this reverse transcriptase.

Preparation of Fluorescent Dye-Containing Polymelamine Particles Labeled with Streptavidin Fluorescent dye-containing polymelamine particles (phosphor-integrated nanoparticles) labeled with streptavidin were prepared in the same manner as in Example 7, except that the amount of SulfoRhodamine 101 (manufactured by Sigma-Aldrich) was changed from 20.3 mg to 14.4 mg and the amount of the melamine resin material NIKA-LAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.
<Direct Binding of Phosphor-Integrated Nanoparticles and cDNA (5'-End Labeling)>

For 2 μg of the above-prepared DNA, using a kit "5' EndTag™ Nucleic Acid Labeling System (catalog No. MB-9001)" manufactured by Vector Laboratories, Inc. in accordance with its protocol, the 5'-end of the nucleic acid molecule was converted from phosphoric acid to thiophosphoric acid as described below.

The following materials were mixed in a centrifuge tube and incubated at 37° C. for 30 minutes.

nucleic acid molecule of the cDNA: 2 μg (/8 μL of ultrapure water)
Universal reaction buffer: 1 μL
alkaline phosphatase: 1 μL In addition, the resulting mixture was further mixed with the following materials and incubated at 37° C. for 30 minutes.

Universal reaction buffer: 2 μL
ATPγS: 1 μL
T4 polynucleotide kinase: 2 μL

Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-labeled cDNA (probe reagent A8) (final concentration: 1 μg/250 μL).
<Other Observation, Etc.>

Verification of the DNA probe, storage of the DNA probe, FISH, bright-field observation, confocal fluorescence microscope observation, fluorescence microscope observation and the like were performed in the same manner as in Comparative Example 4.

In the verification of the DNA probe, since only the 5'-end was labeled, the binding molar ratio was found to be about 1:1. Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.
(Results)

In the confocal microscope observation and fluorescence microscope observation, only those cells showing 2 bright spots were observed, and the EGFR gene was properly detected even in the fluorescence microscope observation where the detection sensitivity is lower than that of the confocal microscope observation.

Example 34

Preparation of DNA Probe Having Biotin Labeling Ratio of 5%

On the probe search engine "HD-FISH" (URL: www.h-dfish.eu/Find#probes.php), a unique sequence was searched by designating a specific region (from the 55,086,714th base to the 55,324,313th base) of human 7th chromosome, and a unique sequence following the sequence of the 55,091,671st to the 55,091,880th bases that exists in the specific region was searched and obtained. By requesting the synthesis of a nucleic acid based on the thus obtained sequence data, a 20-base DNA (nucleic acid molecule) having a HER2 gene-related sequence (5'-AGCTGGCCAGTTTGAATTTG-3' (SEQ ID NO: 12)) was prepared.

Using 4 μg of the thus prepared DNA, a DNA labeled with biotin at the 5'-end was obtained in the same manner as in Example 12.

Preparation of Fluorescent Dye-Containing Polymelamine Particles Labeled with Streptavidin Fluorescent dye-containing polymelamine particles labeled with streptavidin were prepared in the same manner as in Example 7, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.
(Preparation of Streptavidin/Binding of Particles and Streptavidin)

Meanwhile, streptavidin capable of binding to the phosphor-integrated nanoparticles was prepared and binding of the phosphor-integrated nanoparticles and the thus prepared streptavidin was performed in the same manner as in Example 3, thereby obtaining phosphor-integrated nanoparticles bound with streptavidin.
<Preparation of DNA Probe in which Phosphor-Integrated Nanoparticles (158 nm, Melamine Particles) and DNA are Bound>

The biotin-labeled DNA obtained above in an amount of 25 μL (concentration: 1 μg/250 μL) and a solution containing the phosphor-integrated nanoparticles modified with streptavidin were mixed to perform binding reaction at room temperature for 30 minutes, thereby obtaining a DNA probe for EGFR detection (probe reagent A9).
<Other Observation, Etc.>

Verification of the DNA probe, storage of the DNA probe, FISH, bright-field observation, confocal fluorescence microscope observation, fluorescence microscope observation and the like were performed in the same manner as in Comparative Example 4.

As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.

Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.

(Results)

In the confocal microscope observation and fluorescence microscope observation, only those cells showing 2 bright spots were observed, and the EGFR gene was properly detected even in the fluorescence microscope observation where the detection sensitivity is lower than that of the confocal microscope observation.

Example 35

Preparation of DNA Probe Having Labeling Ratio of 0.5%

SEQ ID NO of the RET gene (Chromosome 10: 43,584,007-43,585,055) obtained by a search on the gene database "e! Ensembl$^{ASIA}$" (http://asia.ensembl.org/index.html) was input and searched on the probe search engine "HD-FISH" (URL: http://www.hdfish.eu/Find#probes.php), and 146 RET primer pairs were found in accordance with the method described in Bienko M. Nat Methods (2013).

A 1,048-base cDNA (nucleic acid molecule) having a RET gene-related sequence was prepared by performing a reverse transcription reaction using total RNA extracted from HT-29 cells as a template along with a set of a forward primer (5'-TTCTGTGAGCATTTGCTTGG-3' (SEQ ID NO: 13)) and a reverse primer (5'-CTCTTGACAATGTC-CCCTGG-3' (SEQ ID NO: 14)) among the thus searched RET-selective sequences as well as "SuperScript (registered trademark) II Reverse Transcriptase" manufactured by Invitrogen Corp. and a common commercially available PCR reagent in accordance with the protocol described in the product manual of this reverse transcriptase.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.

<Biotin Labeling of 5'-End>

Using 40 µg of the thus prepared cDNA, a cDNA labeled with biotin at the 5'-end was obtained in the same manner as in Example 12.

<Preparation of DNA Probe in which Phosphor-Integrated Nanoparticles and cDNA are Bound>

The biotin-labeled cDNA obtained above in an amount of 25 µL (concentration: 1 µg/250 µL) and a solution containing the phosphor-integrated nanoparticles modified with streptavidin were mixed to perform binding reaction at room temperature for 30 minutes, thereby obtaining a DNA probe for RET detection (probe reagent A10).

<Other Observation, Etc.>

As for the verification of the binding molar ratio of the cDNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the cDNA.

Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.

(Results)

In the confocal microscope observation and fluorescence microscope observation, only those cells showing 2 bright spots were observed, and the RET gene was properly detected even in the fluorescence microscope observation where the detection sensitivity is lower than that of the confocal microscope observation.

Example 36

Preparation of DNA Probe Having Labeling Ratio of 0.49%

SEQ ID NOs of the met proto-oncogene MET (MET) (Chromosome 7: 116, 312, 444-116, 438, 440) obtained by a search on the gene database "e! Ensembl$^{ASIA}$" (asia.ensembl.org/index.html) were input and searched on the probe search engine "HD-FISH" (URL: www.hdfish.eu/Find#probes.php), and 295 primer pairs of the met proto-oncogene MET (MET) were found in accordance with the method described in Bienko M. Nat Methods (2013).

A 205-base cDNA (nucleic acid molecule) having a MET gene-related sequence was prepared by performing a reverse transcription reaction using total RNA extracted from HT-29 cells as a template along with a set of a forward primer (5'-TCACAGCAGCAATTCCCATA-3' (SEQ ID NO: 15)) and a reverse primer (5'-CCAGCATTTCAGAAGAG-GTTTT-3' (SEQ ID NO: 16)) among MET-selective sequences as well as "SuperScript (registered trademark) II Reverse Transcriptase" manufactured by Invitrogen Corp. and a common commercially available PCR reagent in accordance with the protocol described in the product manual of this reverse transcriptase.

<Preparation of Fluorescent Dye-Containing Polymelamine Particles Labeled with Streptavidin>

Fluorescent dye-containing polymelamine particles labeled with streptavidin were prepared in the same manner as in Example 3, except that the amount of SulfoRhodamine 101 (manufactured by Sigma-Aldrich) was changed from 20.3 mg to 14.4 mg and the amount of the melamine resin material NIKALAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 3. Washing and the like were also performed in the same manner as in Example 3.

<Direct Binding of Phosphor-Integrated Nanoparticles and Nucleic Acid Molecule (5'-End Labeling)>

A probe having thiophosphoric acid at the 5'-end which was prepared from 2 μg of the above-prepared nucleic acid molecule of cDNA in the same manner as in Example 34 was allowed to react with a solution containing the fluorescent dye-containing phosphor-integrated nanoparticles having terminal maleimide, thereby preparing a probe directly bound with the phosphor-integrated nanoparticles at the 5'-end.

The following materials were mixed in a centrifuge tube and incubated at 37° C. for 30 minutes.
nucleic acid molecule of the cDNA: 2 μg (/8 μL of ultrapure water)
universal reaction buffer: 1 μL
alkaline phosphatase: 1 μL In addition, the resulting mixture was further mixed with the following materials and incubated at 37° C. for 30 minutes.
Universal reaction buffer: 2 μL
ATPγS: 1 μL
T4 polynucleotide kinase: 2 μL Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 μL of 3 M sodium acetate solution (pH 5.2) and 150 μL of 100% ethanol were added, and the resultant was left to stand at −20° C. for at least one hour and subsequently centrifuged at 4° C. and 16,000 rpm for 10 minutes to form precipitates. Further, 500 μL of 70% ethanol was added and the resultant was centrifuged at 4° C. and 16,000 rpm for 1 minute, followed by removal of the resulting supernatant. Then, 5 to 10 μL of distilled water was added to the thus formed precipitates and the precipitates were completely dissolved, thereby obtaining a solution of a phosphor-integrated nanoparticle-labeled cDNA (probe reagent A11) (final concentration: 1 μg/250 μL).

<Other Observation, Etc.>

Verification of the DNA probe, storage of the DNA probe, FISH, bright-field observation, confocal fluorescence microscope observation, fluorescence microscope observation and the like were performed in the same manner as in Comparative Example 4.

In the verification of the DNA probe, since only the 5'-end was labeled, the binding molar ratio of the cDNA and the phosphor-integrated nanoparticles was found to be about 1:1. Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.

(Results)

In the confocal microscope observation and fluorescence microscope observation, only those cells showing 2 bright spots were observed, and the MET gene was properly detected even in the fluorescence microscope observation where the detection sensitivity is lower than that of the confocal microscope observation.

Example 37

Preparation of DNA Probe Having Labeling Ratio of 0.46%

SEQ ID NOs of the FGFR2 gene (Chromosome 7: 55, 086, 714-55, 324, 313) obtained by a search on the gene database "e! Ensembl$^{ASIA}$" (asia.ensembl.org/index.html) were input to the probe search engine "HD-FISH" (URL: www.hdfish.eu/Find#probes.php), and 280 FGFR2 primer pairs were found in accordance with the method described in Bienko M. Nat Methods (2013).

A 217-base cDNA (nucleic acid molecule) having a FGFR2 gene-related sequence was prepared by performing a reverse transcription reaction using total RNA extracted from HT-29 cells as a template along with a set of a forward primer (5'-ATGAGTCACTGCACACAGCC-3' (SEQ ID NO: 17)) and a reverse primer (5'-TGAGTGAGATGTG-GTCCAGG-3' (SEQ ID NO: 18)) among FGFR2-selective sequences as well as "SuperScript (registered trademark) II Reverse Transcriptase" manufactured by Invitrogen Corp. and a common commercially available PCR reagent in accordance with the protocol described in the product manual of this reverse transcriptase.

<Preparation of Fluorescent Dye-Containing Polymelamine Particles Labeled with Streptavidin>

Fluorescent dye-containing polymelamine particles labeled with streptavidin were prepared in the same manner as in Example 7. As a result of SEM observation of 1,000 of the thus obtained nanoparticles, their average particle size was found to be 280 nm.

Further, a mixture containing fluorescent dye-containing phosphor-integrated nanoparticles having terminal maleimide was obtained in the same manner as in Example 3. Washing and the like were also performed in the same manner as in Example 3.

<Biotin Labeling of 5'-End>

Using 2 μg of the thus prepared nucleic acid molecule of cDNA, a nucleic acid molecule labeled with biotin at the 5'-end was obtained and a DNA probe (probe reagent A12) was subsequently obtained in the same manner as in Example 12.

<Other Observation, Etc.>

Verification of the DNA probe, storage of the DNA probe, FISH, bright-field observation, confocal fluorescence microscope observation, fluorescence microscope observation and the like were performed in the same manner as in Comparative Example 3. In the verification of the DNA probe, the binding molar ratio was determined to be about 1:1 by a HABA-avidin method. Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 30.

(Results)

In the confocal microscope observation and fluorescence microscope observation, only those cells showing 2 bright spots were observed, and the FGFR2 gene was properly detected even in the fluorescence microscope observation where the detection sensitivity is lower than that of the confocal microscope observation.

Example 38

Preparation of DNA Probe Having Biotin Labeling Ratio of 0.21%

A 473-base cDNA (nucleic acid molecule) having an EGFR gene-related sequence was prepared and nick translation was performed in the same manner as in Example 31, except that the nick translation was performed without adding Biotin-d-UTP and the thus obtained DNA was biotinylated at the 5'-end in the same manner as in Example 12.
<Preparation of Fluorescent Dye-Containing Polymelamine Particles Labeled with Streptavidin>

Fluorescent dye-containing polymelamine particles (phosphor-integrated nanoparticles) labeled with streptavidin were prepared in the same manner as in Example 7, except that the amount of SulfoRhodamine 101 (manufactured by Sigma-Aldrich) was changed from 20.3 mg to 14.4 mg and the amount of the melamine resin material NIKA-LAC MX-035 (manufactured by Nippon Carbide Industries Co., Inc.) was changed from 0.81 g to 0.21 g. As a result of SEM observation of 1,000 of the thus obtained nanoparticles, their average particle size was found to be 158 nm.

Further, a mixture containing fluorescent dye-containing phosphor-integrated nanoparticles having terminal maleimide was obtained in the same manner as in Example 7. Washing and the like were also performed in the same manner as in Example 7.
<Direct Binding of Phosphor-Integrated Nanoparticles and DNA (5'-End Labeling)>

For 2 µg of the above-prepared DNA, using a kit "5' EndTag™ Nucleic Acid Labeling System (catalog No. MB-9001)" manufactured by Vector Laboratories, Inc. in accordance with its protocol, the 5'-end of the nucleic acid molecule was converted from phosphoric acid to thiophosphoric acid as described below.

The following materials were mixed in a centrifuge tube and incubated at 37° C. for 30 minutes.
  nucleic acid molecule of the cDNA: 2 µg (/8 µL of ultrapure water)
  Universal reaction buffer: 1 µL
  alkaline phosphatase: 1 µL
In addition, the resulting mixture was further mixed with the following materials and incubated at 37° C. for 30 minutes.

Universal reaction buffer: 2 µL
ATPγS: 1 µL
T4 polynucleotide kinase: 2 µL

Next, the resultant was allowed to react with the above-obtained mixture containing fluorescent dye-containing phosphor-integrated nanoparticles having terminal maleimide, thereby preparing a probe directly bound with the phosphor-integrated nanoparticles at the 5'-end.

The thus obtained reaction solution of this probe was purified using a micro-spin column for nucleic acid purification ("MicroSpin S-200HR Column" manufactured by GE Healthcare, product number: "#27-5120-01").

To this solution, about 5.56 µL of 3 M sodium acetate solution (pH 5.2) and 150 µL of 100% ethanol were added, and the resultant was left to stand at −20° C. for at least one hour and subsequently centrifuged at 4° C. and 16,000 rpm for 10 minutes to form precipitates. Further, 500 µL of 70% ethanol was added and the resultant was centrifuged at 4° C. and 16,000 rpm for 1 minute, followed by removal of the resulting supernatant. Then, 5 to 10 µL of distilled water was added to the thus formed precipitates and the precipitates were completely dissolved, thereby obtaining a solution of a phosphor-integrated nanoparticle-labeled DNA (probe reagent A8) (final concentration: 1 µg/250 µL).

[Other Observation, Etc.]

Verification of the DNA probe, storage of the DNA probe, FISH, bright-field observation, confocal fluorescence microscope observation, fluorescence microscope observation and the like were performed in the same manner as in Example 31.

In the verification of the DNA probe, since only the 5'-end was labeled, the binding molar ratio was determined to be 1:1. Further, using a tissue array of healthy individuals ("FDA normal organ tissue microarray of human" manufactured by US Biomax, Inc., product number: FDA999b) as a specimen slide, confocal fluorescence microscope observation, fluorescence microscope observation and the like were performed in the same manner as in Example 31.

<Results and Discussion>

In the confocal microscope observation and fluorescence microscope observation, only those cells showing 2 bright spots were observed, and the EGFR gene was properly detected even in the fluorescence microscope observation where the detection sensitivity is lower than that of the confocal microscope observation.

TABLE 5

| | DNA clone | | | Substrate used in nick translation (uL) | | | DNA | Labeling |
| --- | --- | --- | --- | --- | --- | --- | --- | --- |
| | Number of bases | | Probe reagent | Biotin-d-UTP | dTTP | dNTP | clone:label (molar ratio) | ratio (%) |
| Example 30 | 300 | HER2 | A2 | 0.2 | 1.5 | 5 | 1:5 | 1.67 |
| Example 31 | 473 | EFGR | A7 | 1.5 | 0.5 | 5 | 1:40 | 8.46 |
| Example 32 | 473 | EFGR | A8 | 1.5 | 0.5 | 5 | 1:1 | 0.21 |
| Example 33 | 217 | EGFR | A8 | | | | 1:1 | 0.5 |
| Example 34 | 20 | EGFR | A9 | | | | 1:1 | 5 |
| Example 35 | 1,048 | RET | A10 | | | | 1:1 | 0.5 |
| Example 36 | 205 | MET | A11 | | | | 1:1 | 0.49 |
| Example 37 | 217 | FGFR2 | A12 | | | | 1:1 | 0.46 |

TABLE 5-continued

| | | Phosphor | | | |
|---|---|---|---|---|---|
| | | Base material | Particle size (nm) | Confocal microscope | Fluorescence microscope |
| Example 30 | PID | melamine resin | 158 | Bright spots were observable immediately after staining. | Bright spots were observable immediately after staining. |
| Example 31 | PID | melamine resin | 40 | Bright spots were observable immediately after staining. | Bright spots were observable immediately after staining. |
| Example 32 | PID | melamine resin | 158 | Bright spots were observable immediately after staining. | Bright spots were observable immediately after staining. |
| Example 33 | PID | melamine resin | 158 | Bright spots were observable. | Bright spots were observable. |
| Example 34 | PID | melamine resin | 158 | Bright spots were observable. | Bright spots were observable. |
| Example 35 | PID | melamine resin | 158 | Bright spots were observable. | Bright spots were observable. |
| Example 36 | PID | melamine resin | 158 | Bright spots were observable. | Bright spots were observable. |
| Example 37 | PID | melamine resin | 280 | Bright spots were observable. | Bright spots were observable. |

Example 38

Verification of the DNA probe, storage of the DNA probe, FISH, bright-field observation, confocal fluorescence microscope observation, fluorescence microscope observation and the like were performed in the same manner as in Example 3 except that, in FISH, the final concentration of the probe reagent F prepared in Example 3 was changed to 5 µg/µL.
(Results)
Bright spots were observed under a confocal fluorescence microscope and a fluorescence microscope, and the number of bright spots found in the fluorescence microscope observation was 77 (Table 6).

Example 39

Verification of the DNA probe, storage of the DNA probe, FISH, bright-field observation, confocal fluorescence microscope observation, fluorescence microscope observation and the like were performed in the same manner as in Example 3 except that, in FISH, the final concentration of the probe reagent F prepared in Example 3 was changed to 1 µg/µL.
(Results)
Bright spots were observed under a confocal fluorescence microscope and a fluorescence microscope, and the number of bright spots found in the fluorescence microscope observation was 74 (Table 6).

Example 40

Verification of the DNA probe, storage of the DNA probe, FISH, bright-field observation, confocal fluorescence microscope observation, fluorescence microscope observation and the like were performed in the same manner as in Example 3 except that, in FISH, the final concentration of the probe reagent F prepared in Example 3 was changed to 0.2 µg/µL.
(Results)
Bright spots were observed under a confocal fluorescence microscope and a fluorescence microscope, and the number of bright spots found in the fluorescence microscope observation was 62 (Table 6).

Example 41

A probe was prepared in accordance with the method (PCR) described in a document (Bienko M., Nat Method 2013, 122). Specifically, by accessing the database described in the document (www.hdfish.eu.), primer sequences capable of hybridizing to HER2 were displayed. PCR was performed in accordance with the document using a forward primer (5'-biotin-ACGCCTGATGGGTTAATGAG-3' (SEQ ID NO: 19)) and a reverse primer (5'-aagtagaggcaggga-gagcc-3' (SEQ ID NO: 20)), and a 217-base DNA fragment was recovered.

To the thus obtained DNA fragment labeled with biotin at the 5'-end, the SulfoRhodamine 101-containing melamine resin particles (phosphor-integrated nanoparticles) labeled with streptavidin, which were produced in Example 17, were bound in the same manner as in Example 17, thereby obtaining a DNA probe for HER2 detection (probe reagent X) bound with the phosphor-integrated nanoparticles at the 5'-end.
<Other Observation, Etc.>
FISH, storage of the DNA probe, bright-field observation, confocal fluorescence microscope observation, fluorescence microscope observation and the like were performed in the same manner as in Example 38, except that the DNA probe (probe reagent X) was verified in the same manner as in Comparative Example 4 and the final concentration of the probe reagent X in FISH was changed to 1.0 µg/µL.

As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.
(Results)
Bright spots were observed under a confocal fluorescence microscope and a fluorescence microscope, and the number of bright spots found in the fluorescence microscope observation was 78 (Table 6).

Example 42

Storage of the DNA probe, FISH, bright-field observation, confocal fluorescence microscope observation, fluorescence microscope observation and the like were performed in the same manner as in Example 41, except that, in FISH, the final concentration of the probe reagent X prepared in Example 41 was changed to 0.2 µg/µL.

(Results)

Bright spots were observed under a confocal fluorescence microscope and a fluorescence microscope, and the number of bright spots found in the fluorescence microscope observation was 77 (Table 6).

Example 43

Storage of the DNA probe, FISH, bright-field observation, confocal fluorescence microscope observation, fluorescence microscope observation and the like were performed in the same manner as in Example 41, except that, in FISH, the final concentration of the probe reagent X prepared in Example 41 was changed to 0.04 µg/µL.
(Results)

Bright spots were observed under a confocal fluorescence microscope and a fluorescence microscope, and the number of bright spots found in the fluorescence microscope observation was 78 (Table 6).

Example 44

A probe was prepared in accordance with the method (PCR) described in a document (Bienko M., Nat Method 2013, 122). Specifically, by accessing the database described in the document (www.hdfish.eu.), primer sequences capable of hybridizing to HER2 were displayed. PCR was performed in accordance with the document using a forward primer (5'biotin-TGCTTCCaaccttggttttt (SEQ ID NO: 21)) and a reverse primer (TGCAAGTGCaatacctgctc (SEQ ID NO: 22)), and a 3,347-base DNA fragment was recovered.

To the thus obtained DNA fragment labeled with biotin at the 5'-end, the SulfoRhodamine 101-containing melamine resin particles (phosphor-integrated nanoparticles) labeled with streptavidin, which were produced in Example 17, were bound in the same manner as in Example 17, thereby obtaining a DNA probe for HER2 detection (probe reagent Y) bound with the phosphor-integrated nanoparticles at the 5'-end.
<Other Observation, Etc.>

FISH, storage of the DNA probe, bright-field observation, confocal fluorescence microscope observation, fluorescence microscope observation and the like were performed in the same manner as in Example 38, except that the DNA probe (probe reagent Y) was verified in the same manner as in Example 1 and the final concentration of the probe reagent Y in FISH was changed to 1.0 µg/µL.

As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K. K.) where, with HABA being bound to streptavidin of the phosphor-integrated nanoparticles, HABA was substituted with biotin of the DNA.
(Results)

Bright spots were observed under a confocal fluorescence microscope and a fluorescence microscope, and the number of bright spots found in the fluorescence microscope observation was 80 (Table 6).

Example 45

Storage of the DNA probe, FISH, bright-field observation, confocal fluorescence microscope observation, fluorescence microscope observation and the like were performed in the same manner as in Example 44, except that, in FISH, the final concentration of the probe reagent Y prepared in Example 44 was changed to 0.2 µg/µL.
(Results)

Bright spots were observed under a confocal fluorescence microscope and a fluorescence microscope, and the number of bright spots found in the fluorescence microscope observation was 77 (Table 6).

Example 46

Storage of the DNA probe, FISH, bright-field observation, confocal fluorescence microscope observation, fluorescence microscope observation and the like were performed in the same manner as in Example 44, except that, in FISH, the final concentration of the probe reagent Y prepared in Example 44 was changed to 0.04 µg/µL.
(Results)

Bright spots were observed under a confocal fluorescence microscope and a fluorescence microscope, and the number of bright spots found in the fluorescence microscope observation was 79 (Table 6).

Example 47

A 20-base DNA fragment was produced and the 5'-end of this DNA fragment was subsequently labeled with biotin in the same manner as in Example 16.

Then, to the thus obtained DNA fragment labeled with biotin at the 5'-end, the SulfoRhodamine 101-containing melamine resin particles (phosphor-integrated nanoparticles) labeled with streptavidin, which were produced in Example 17, were bound in the same manner as in Example 17, thereby obtaining a DNA probe for HER2 detection (probe reagent Z) bound with the phosphor-integrated nanoparticles at the 5'-end.
<Other Observation, Etc.>

FISH, storage of the DNA probe, bright-field observation, confocal fluorescence microscope observation, fluorescence microscope observation and the like were performed in the same manner as in Example 38, except that the DNA probe (probe reagent Z) was verified in the same manner as in Comparative Example 4 and the final concentration of the probe reagent Z in FISH was changed to 1.0 µg/µL.

As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K.K.) where, with HABA being bound to streptavidin of the phosphor-integrated nanoparticles, HABA was substituted with biotin of the DNA.
(Results)

Bright spots were observed under a confocal fluorescence microscope and a fluorescence microscope, and the number of bright spots found in the fluorescence microscope observation was 73 (Table 6).

Example 48

Storage of the DNA probe, FISH, bright-field observation, confocal fluorescence microscope observation, fluorescence microscope observation and the like were performed in the same manner as in Example 47, except that, in FISH, the final concentration of the probe reagent Z prepared in Example 47 was changed to 0.2 µg/µL.

(Results)

Bright spots were observed under a confocal fluorescence microscope and a fluorescence microscope, and the number of bright spots found in the fluorescence microscope observation was 73 (Table 6).

Example 49

Storage of the DNA probe, FISH, bright-field observation, confocal fluorescence microscope observation, fluorescence microscope observation and the like were performed in the same manner as in Example 47, except that, in FISH, the final concentration of the probe reagent Z prepared in Example 47 was changed to 0.04 μg/μL.
(Results)

Bright spots were observed under a confocal fluorescence microscope and a fluorescence microscope, and the number of bright spots found in the fluorescence microscope observation was 73 (Table 6).

Example 50

A 20-base DNA fragment was produced and the 5'-end of this DNA fragment was subsequently labeled with biotin in the same manner as in Example 16.

Then, to the thus obtained DNA fragment labeled with biotin at the 5'-end, the SulfoRhodamine 101-containing melamine resin particles (phosphor-integrated nanoparticles) labeled with streptavidin, which were produced in Example 17, were bound in the same manner as in Example 17, thereby obtaining a DNA probe for HER2 detection (probe reagent ZZ) bound with the phosphor-integrated nanoparticles at the 5'-end.
<Other Observation, Etc.>

FISH, storage of the DNA probe, bright-field observation, confocal fluorescence microscope observation, fluorescence microscope observation and the like were performed in the same manner as in Example 38, except that the DNA probe (probe reagent ZZ) was verified in the same manner as in Example 27 and the final concentration of the probe reagent ZZ in FISH was changed to 1.0 μg/μL.

As for the verification of the binding molar ratio of the DNA and biotin, the binding molar ratio was determined to be about 1:1 by a HABA-avidin method using "Thermo Scientific Pierce Biotin Quantitation Kit" (manufactured by Thermo Fisher Scientific K.K.) where, with HABA being bound to streptavidin of the phosphor-integrated nanoparticles, HABA was substituted with biotin of the DNA.
(Results)

Bright spots were observed under a confocal fluorescence microscope and a fluorescence microscope, and the number of bright spots found in the fluorescence microscope observation was 62 (Table 6).

Example 51

Storage of the DNA probe, FISH, bright-field observation, confocal fluorescence microscope observation, fluorescence microscope observation and the like were performed in the same manner as in Example 50, except that, in FISH, the final concentration of the probe reagent ZZ prepared in Example 50 was changed to 0.2 μg/μL.
(Results)

Bright spots were observed under a confocal fluorescence microscope and a fluorescence microscope, and the number of bright spots found in the fluorescence microscope observation was 60 (Table 6).

Example 52

Storage of the DNA probe, FISH, bright-field observation, confocal fluorescence microscope observation, fluorescence microscope observation and the like were performed in the same manner as in Example 50, except that, in FISH, the final concentration of the probe reagent ZZ prepared in Example 50 was changed to 0.04 μg/μL.
(Results)

Bright spots were observed under a confocal fluorescence microscope and a fluorescence microscope, and the number of bright spots found in the fluorescence microscope observation was 48 (Table 6).

TABLE 6

| | DNA clone | | | Substrate used in nick translation (uL) | | | DNA | Labeling | Phosphor | | | Confocal microscope, Fluorescence microscope | |
|---|---|---|---|---|---|---|---|---|---|---|---|---|---|
| | Number of bases | | Probe reagent | Biotin-d-UTP | dTTP | dNTP | clone:label (molar ratio) | ratio (%) | | Base material | Particle size (nm) | Observ-ability | Number of bright spots |
| Example 38 | 150,000 | HER2 | F* | 0.2 | 1.5 | 5 | 1:2,000 | 1.33 | PID | melamine resin | 280 | observable | 77 |
| Example 39 | 150,000 | HER2 | F* | 0.2 | 1.5 | 5 | 1:2,000 | 1.33 | PID | melamine resin | 280 | observable | 74 |
| Example 40 | 150,000 | HER2 | F* | 0.2 | 1.5 | 5 | 1:2,000 | 1.33 | PID | melamine resin | 280 | observable | 62 |
| Example 41 | 217 | HER2 | X* | | | | 1:1 | 0.46 | PID | melamine resin | 158 | observable | 78 |
| Example 42 | 217 | HER2 | X* | | | | 1:1 | 0.46 | PID | melamine resin | 158 | observable | 77 |
| Example 43 | 217 | HER2 | X* | | | | 1:1 | 0.46 | PID | melamine resin | 158 | observable | 78 |
| Example 44 | 3,347 | HER2 | Y* | | | | 1:1 | 0.03 | PID | melamine resin | 158 | observable | 80 |
| Example 45 | 3,347 | HER2 | Y* | | | | 1:1 | 0.03 | PID | melamine resin | 158 | observable | 77 |
| Example 46 | 3,347 | HER2 | Y* | | | | 1:1 | 0.03 | PID | melamine resin | 158 | observable | 79 |
| Example 47 | 20 | HER2 | Z* | | | | 1:1 | 1.66 | PID | melamine resin | 158 | observable | 73 |

TABLE 6-continued

| | DNA clone | | Substrate used in nick translation (uL) | | | DNA clone:label (molar ratio) | Labeling ratio (%) | Phosphor | | Confocal microscope, Fluorescence microscope | |
| | Number of bases | Probe reagent | Biotin-d-UTP | dTTP | dNTP | | | Base material | Particle size (nm) | Observ-ability | Number of bright spots |
|---|---|---|---|---|---|---|---|---|---|---|---|
| Example 48 | 60 | HER2 | Z* | | | 1:1 | 1.66 | PID | melamine resin | 158 | observable | 73 |
| Example 49 | 60 | HER2 | Z* | | | 1:1 | 1.66 | PID | melamine resin | 158 | observable | 73 |
| Example 50 | 20 | HER2 | ZZ* | | | 1:1 | 2.5 | PID | melamine resin | 158 | observable | 62 |
| Example 51 | 40 | HER2 | ZZ* | | | 1:1 | 2.5 | PID | melamine resin | 158 | observable | 60 |
| Example 52 | 40 | HER2 | ZZ* | | | 1:1 | 2.5 | PID | melamine resin | 158 | observable | 49 |

*Each alphabet represents the same probe; however, the probe concentration was different among Examples.

In the above, embodiments and examples of the present invention were described in detail; however, in the present invention, design modifications can be made as long as they do not deviate from the gist of the present invention described in claims.

The invention claimed is:

1. A probe reagent for in situ hybridization, comprising:
a plurality of phosphor-integrated nanoparticles containing phosphors integrated therein and a matrix material, wherein said matrix material comprises a resin, and said resin is a melamine resin; and
a nucleic acid molecule having a prescribed nucleic acid sequence,
said plurality of phosphor-integrated nanoparticles and said nucleic acid molecule being bound with each other, and at least one of said plurality of phosphor-integrated nanoparticles is bound to a 3' or 5' terminal end of said nucleic acid molecule.

2. The probe reagent according to claim 1, wherein said phosphor-integrated nanoparticles have an average particle size of 300 nm or smaller.

3. The probe reagent according to claim 1, wherein said nucleic acid molecule and said phosphor-integrated nanoparticles are bound at a molar ratio of 1:1 to 1:5,000.

4. The probe reagent according to claim 1, wherein said nucleic acid molecule and said phosphor-integrated nanoparticles are bound at a molar ratio of 1:1 to 1:40.

5. The probe reagent for in situ hybridization according to claim 1, which is obtained by binding said phosphor-integrated nanoparticles containing phosphors integrated therein to said nucleic acid molecule having a prescribed nucleic acid sequence of 5,000 or less bases.

6. The probe reagent for in situ hybridization according to claim 5, which is obtained by binding said phosphor-integrated nanoparticles containing phosphors integrated therein to said nucleic acid molecule having a prescribed nucleic acid sequence of 5,000 or less bases in accordance with a method that utilizes nucleic acid terminal labeling or nick translation.

7. The probe reagent according to claim 1, wherein a labeling ratio (%) of said phosphors with respect to said nucleic acid molecule is 13.33% or less.

8. The probe reagent according to claim 1, wherein
said phosphors integrated are low-molecular-weight fluorescent dyes or quantum dots.

9. The probe reagent according to claim 1, wherein
a first biomolecule is linked to said nucleic acid molecule,
a second biomolecule is linked to said phosphor-integrated nanoparticles, and
said nucleic acid molecule and said phosphor-integrated nanoparticles are bound via specific bonds formed by said first and second biomolecules.

10. The probe reagent according to claim 9, wherein said first and second biomolecules are each streptavidin or biotin.

11. The probe reagent according to claim 1, wherein said phosphor-integrated nanoparticles are directly bound to a base of said nucleic acid molecule.

12. The probe reagent according to claim 11, wherein said phosphor-integrated nanoparticles are covalently-bound to the base of said nucleic acid molecule.

13. The probe reagent according to claim 1, wherein the phosphors are dispersed inside the nanoparticles or bound to surfaces of the nanoparticles.

14. The probe reagent according to claim 1, wherein the nucleic acid molecule has a nucleic acid sequence of 5,000 or less bases.

15. A probe reagent for in situ hybridization, comprising:
a plurality of fluorescent nanoparticles containing phosphors integrated therein and a matrix material, wherein said matrix material comprises a resin, and said resin is a melamine resin; and
a nucleic acid molecule having a prescribed nucleic acid sequence,
wherein the plurality of fluorescent nanoparticles is bound to the nucleic acid molecule, at least one of said plurality of fluorescent nanoparticles is bound to a 3' or 5' terminal end of said nucleic acid molecule, and 20,000 mol or more of the plurality of fluorescent nanoparticles are bound per 1 mol of a nucleic acid molecule.

16. A probe reagent kit for FISH, separately comprising:
a nucleic acid molecule which has a sequence of less than 150,000 bases that is complementary to a sequence of a specific region on a chromosome and to which a first biomolecule is linked; and
a plurality of phosphor-integrated nanoparticles to which a second biomolecule capable of specifically binding to said first biomolecule is linked;
wherein said plurality phosphor-integrated nanoparticles contain phosphors integrated therein and a matrix material, wherein said matrix material comprises a resin, and said resin is a melamine resin, and
said plurality of phosphor-integrated nanoparticles and said nucleic acid molecule are configured to be bound with each other, and at least one of said plurality of phosphor-integrated nanoparticles is configured to be bound to a 3' or 5' terminal end of said nucleic acid molecule.

17. A probe reagent kit for FISH, separately comprising:
a nucleic acid molecule which has a sequence of 5,000 or less bases that is complementary to a sequence of a specific region on a chromosome and to which a first biomolecule is linked to a terminal(s) and/or 1 to 50 spots other than said terminals; and
a plurality of phosphor-integrated nanoparticles to which a second biomolecule capable of specifically binding to said first biomolecule is linked;
wherein said plurality phosphor-integrated nanoparticles contain phosphors integrated therein and a matrix material, wherein said matrix material comprises a resin, and said resin is a melamine resin, and
said plurality of phosphor-integrated nanoparticles and said nucleic acid molecule are configured to be bound with each other, and at least one of said plurality of phosphor-integrated nanoparticles is configured to be bound to a 3' or 5' terminal end of said nucleic acid molecule.

18. A method for FISH using the probe reagent according to claim 1.

* * * * *

```
                        SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Forward Primer for amplifying a reagion of HER2
      gene

<400> SEQUENCE: 1
cgggagatcc ctgacctgct ggaa                                             24

<210> SEQ ID NO 2
<211> LENGTH: 24
<212> TYPE: DNA
<213> ORGANISM: Artificial Sequence
<220> FEATURE:
<223> OTHER INFORMATION: Reverse Primer for amplifying a reagion of HER2
      gene

<400> SEQUENCE: 2
ctgctggggt accagatact cctc                                             24

<210> SEQ ID NO 3
<211> LENGTH: 24
<212> TYPE: DNA
<213> ORGANISM: Artificial Sequence
<220> FEATURE:
<223> OTHER INFORMATION: Forward Primer for amplifying a reagion of HER2
      gene

<400> SEQUENCE: 3
cgggagatcc ctgacctgct ggaa                                             24

<210> SEQ ID NO 4
<211> LENGTH: 24
<212> TYPE: DNA
<213> ORGANISM: Artificial Sequence
<220> FEATURE:
<223> OTHER INFORMATION: Reverse Primer for amplifying a reagion of HER2
``` gene

<400> SEQUENCE: 4
ctgctggggt accagatact cctc                                          24

<210> SEQ ID NO 5
<211> LENGTH: 20
<212> TYPE: DNA
<213> ORGANISM: Artificial Sequence
<220> FEATURE:
<223> OTHER INFORMATION: DNA sequence of a reagion of HER2 gene

<400> SEQUENCE: 5
acgcctgatg ggttaatgag                                               20

<210> SEQ ID NO 6
<211> LENGTH: 20
<212> TYPE: DNA
<213> ORGANISM: Artificial Sequence
<220> FEATURE:
<223> OTHER INFORMATION: Forward Primer for amplifying a reagion of HER2
      gene

<400> SEQUENCE: 6
acgcctgatg ggttaatgag                                               20

<210> SEQ ID NO 7
<211> LENGTH: 20
<212> TYPE: DNA
<213> ORGANISM: Artificial Sequence
<220> FEATURE:
<223> OTHER INFORMATION: Reverse Primer for amplifying a reagion of HER2
      gene

<400> SEQUENCE: 7
aagtagaggc agggagagcc                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse Primer for amplifying a reagion of EGFR
      gene

<400> SEQUENCE: 8
tctcagcaac atgtcgatgg                                               20

<210> SEQ ID NO 9
<211> LENGTH: 20
<212> TYPE: DNA
<213> ORGANISM: Artificial Sequence
<220> FEATURE:
<223> OTHER INFORMATION: Forward Primer for amplifying a reagion of EGFR
      gene

<400> SEQUENCE: 9
tcgcacttct tacacttgcg                                               20

<210> SEQ ID NO 10
<211> LENGTH: 20
<212> TYPE: DNA
<213> ORGANISM: Artificial Sequence
<220> FEATURE:
<223> OTHER INFORMATION: Reverse Primer for amplifying a reagion of EGFR
      gene

```
<400> SEQUENCE: 10
cggagtccaa gtgtcctttc                                                 20

<210> SEQ ID NO 11
<211> LENGTH: 20
<212> TYPE: DNA
<213> ORGANISM: Unknown
<220> FEATURE:
<223> OTHER INFORMATION: DNA sequence from EGFR gene

<400> SEQUENCE: 11
ccttctatgc aaagggcaaa                                                 20

<210> SEQ ID NO 12
<211> LENGTH: 20
<212> TYPE: DNA
<213> ORGANISM: Artificial Sequence
<220> FEATURE:
<223> OTHER INFORMATION: Forward Primer for amplifying a reagion of RET
      gene

<400> SEQUENCE: 12
agctggccag tttgaatttg                                                 20

<210> SEQ ID NO 13
<211> LENGTH: 20
<212> TYPE: DNA
<213> ORGANISM: Artificial Sequence
<220> FEATURE:
<223> OTHER INFORMATION: Forward Primer for amplifying a reagion of RET
      gene

<400> SEQUENCE: 13
ttctgtgagc atttgcttgg                                                 20

<210> SEQ ID NO 14
<211> LENGTH: 20
<212> TYPE: DNA
<213> ORGANISM: Artificial Sequence
<220> FEATURE:
<223> OTHER INFORMATION: Reverse Primer for amplifying a reagion of RET
      gene

<400> SEQUENCE: 14
ctcttgacaa tgtcccctgg                                                 20

<210> SEQ ID NO 15
<211> LENGTH: 20
<212> TYPE: DNA
<213> ORGANISM: Artificial Sequence
<220> FEATURE:
<223> OTHER INFORMATION: Forward Primer for amplifying a reagion of MET
      gene

<400> SEQUENCE: 15
tcacagcagc aattcccata                                                 20

<210> SEQ ID NO 16
<211> LENGTH: 22
<212> TYPE: DNA
<213> ORGANISM: Artificial Sequence
<220> FEATURE:
<223> OTHER INFORMATION: Reverse Primer for amplifying a reagion of MET
      gene

<400> SEQUENCE: 16
```

```
ccagcatttc agaagaggtt tt                                              22

<210> SEQ ID NO 17
<211> LENGTH: 20
<212> TYPE: DNA
<213> ORGANISM: Artificial Sequence
<220> FEATURE:
<223> OTHER INFORMATION: Forward Primer for amplifying a reagion of
      FGFR2 gene

<400> SEQUENCE: 17
atgagtcact gcacacagcc                                                 20

<210> SEQ ID NO 18
<211> LENGTH: 20
<212> TYPE: DNA
<213> ORGANISM: Artificial Sequence
<220> FEATURE:
<223> OTHER INFORMATION: Reverse Primer for amplifying a reagion of
      FGFR2 gene

<400> SEQUENCE: 18
tgagtgagat gtggtccagg                                                 20

<210> SEQ ID NO 19
<211> LENGTH: 20
<212> TYPE: DNA
<213> ORGANISM: Artificial Sequence
<220> FEATURE:
<223> OTHER INFORMATION: Forward Primer for amplifying a reagion of HER2
      gene

<400> SEQUENCE: 19
acgcctgatg ggttaatgag                                                 20

<210> SEQ ID NO 20
<211> LENGTH: 20
<212> TYPE: DNA
<213> ORGANISM: Artificial Sequence
<220> FEATURE:
<223> OTHER INFORMATION: Reverse Primer for amplifying a reagion of HER2
      gene

<400> SEQUENCE: 20
aagtagaggc agggagagcc                                                 20

<210> SEQ ID NO 21
<211> LENGTH: 20
<212> TYPE: DNA
<213> ORGANISM: Artificial Sequence
<220> FEATURE:
<223> OTHER INFORMATION: Forward Primer for amplifying a reagion of HER2
      gene
<220> FEATURE:
<221> NAME/KEY: misc_feature
<222> LOCATION: (1)..(1)
<223> OTHER INFORMATION: Biotilated-thymine

<400> SEQUENCE: 21
tgcttccaac cttggttttt                                                 20

<210> SEQ ID NO 22
<211> LENGTH: 20
<212> TYPE: DNA
<213> ORGANISM: Artificial Sequence
<220> FEATURE:
<223> OTHER INFORMATION: Reverse Primer for amplifying a reagion of HER2
      gene
```

<400> SEQUENCE: 22
tgcaagtgca atacctgctc                                                                                       20